United States Patent
Holley et al.

(10) Patent No.: US 11,957,835 B2
(45) Date of Patent: Apr. 16, 2024

(54) EXCHANGER ASSEMBLY FOR RESPIRATORY TREATMENT

(71) Applicant: ResMed Pty Ltd, Bella Vista (AU)

(72) Inventors: Liam Holley, Sydney (AU); Paul Jan Klasek, Bonnyrigg Heights (AU); Robert Henry Frater, Lindfield (AU); Quangang Yang, Kellyville (AU); Pallavi Gosain, Merrylands (AU)

(73) Assignee: ResMed Pty Ltd (AU)

( * ) Notice: Subject to any disclaimer, the term of this patent is extended or adjusted under 35 U.S.C. 154(b) by 1079 days.

(21) Appl. No.: 16/785,009

(22) Filed: Feb. 7, 2020

(65) Prior Publication Data

US 2020/0246564 A1 Aug. 6, 2020

Related U.S. Application Data

(63) Continuation of application No. 14/356,713, filed as application No. PCT/AU2012/001382 on Nov. 9, 2012, now Pat. No. 10,589,042.

(Continued)

(51) Int. Cl.
*A61M 16/08* (2006.01)
*A61M 16/00* (2006.01)
(Continued)

(52) U.S. Cl.
CPC ...... *A61M 16/0003* (2014.02); *A61M 16/024* (2017.08); *A61M 16/06* (2013.01);
(Continued)

(58) Field of Classification Search
CPC .............. A61M 16/08; A61M 16/0833; A61M 16/0841; A61M 16/085; A61M 16/10;
(Continued)

(56) References Cited

U.S. PATENT DOCUMENTS

| 3,375,839 A | 4/1968 | Crenshaw |
| 3,460,558 A | 8/1969 | Johannisson |

(Continued)

FOREIGN PATENT DOCUMENTS

| CN | 2511321 Y | 9/2002 |
| CN | 1664481 A | 9/2005 |

(Continued)

OTHER PUBLICATIONS

Office Action from corresponding JP Application No. P2021-175373 dated Sep. 16, 2022.

(Continued)

*Primary Examiner* — Annette Dixon
(74) *Attorney, Agent, or Firm* — Botos Churchill IP Law LLP

(57) ABSTRACT

An exchanger conduit permits temperature and/or humidity conditioning of a gas for a patient respiratory interface. In an example embodiment, a conduit has a first channel and a second channel where the first channel is configured to conduct an inspiratory gas and the second channel configured to conduct an expiratory gas. An exchanger is positioned along the first channel and the second channel to separate the first channel and the second channel. The exchanger is configured to transfer a component (e.g., temperature or humidity) of the gas of the second channel to the gas of the first channel. In some embodiments, an optional flow resistor may be implemented to permit venting at pressures above atmospheric pressure so as to allow pressure stenting of a patient respiratory system without a substantial direct flow from a flow generator of respiratory treatment apparatus to the patient during patient expiration.

32 Claims, 40 Drawing Sheets

Related U.S. Application Data

(60) Provisional application No. 61/558,648, filed on Nov. 11, 2011.

(51) Int. Cl.
| | | |
|---|---|---|
| *A61M 16/06* | (2006.01) | |
| *A61M 16/10* | (2006.01) | |
| *A61M 16/16* | (2006.01) | |
| *A61M 16/20* | (2006.01) | |
| *A61M 16/14* | (2006.01) | |

(52) U.S. Cl.
CPC ...... *A61M 16/1045* (2013.01); *A61M 16/161* (2014.02); *A61M 16/20* (2013.01); *A61M 16/206* (2014.02); *A61M 16/208* (2013.01); *A61M 2016/0036* (2013.01); *A61M 16/145* (2014.02); *A61M 2205/3368* (2013.01); *A61M 2205/8206* (2013.01)

(58) Field of Classification Search
CPC .......... A61M 16/1045; A61M 16/1055; A61M 16/106; A61M 16/1075; A61M 16/109; A61M 16/147; A61M 16/16; A61M 16/161; A61M 16/162; A61M 16/164; A61M 16/22; A61M 2016/0039; A61M 2205/3368; A61M 2230/43; A61M 2230/432; A62B 18/025; A62B 9/003; B63C 11/24; B63C 11/34; Y10S 128/911
See application file for complete search history.

(56) References Cited

U.S. PATENT DOCUMENTS

| | | | |
|---|---|---|---|
| 3,556,122 A | 1/1971 | Laerdal | |
| 3,747,127 A | 7/1973 | Taub | |
| 3,802,427 A * | 4/1974 | Banjavich | B63C 11/24 128/201.27 |
| 3,895,675 A | 7/1975 | Rein et al. | |
| 3,978,878 A | 9/1976 | Rudolph | |
| 4,030,564 A | 6/1977 | Itagaki | |
| 4,048,993 A | 9/1977 | Dobritz | |
| 4,226,233 A | 10/1980 | Kritzer | |
| 4,428,392 A | 1/1984 | Jones et al. | |
| 4,456,016 A | 6/1984 | Nowacki et al. | |
| 4,538,620 A | 9/1985 | Nowacki et al. | |
| 4,620,537 A * | 11/1986 | Brown | A62B 9/003 128/201.13 |
| 4,811,730 A | 3/1989 | Milano | |
| 4,829,997 A | 5/1989 | Douwens et al. | |
| 4,886,057 A | 12/1989 | Nave | |
| 4,944,310 A | 7/1990 | Sullivan | |
| 5,146,914 A | 9/1992 | Sturrock | |
| 5,295,478 A | 3/1994 | Baldwin | |
| 5,349,946 A * | 9/1994 | McComb | A61M 16/147 128/203.12 |
| 5,398,673 A | 3/1995 | Lambert | |
| 5,469,842 A | 11/1995 | Flynn | |
| 5,482,031 A | 1/1996 | Lambert | |
| 5,765,557 A | 6/1998 | Warters | |
| 5,769,071 A * | 6/1998 | Turnbull | A61M 16/16 128/205.23 |
| 5,937,856 A | 8/1999 | Jonasson et al. | |
| 5,992,413 A * | 11/1999 | Martin, Jr. | A61M 16/085 128/205.28 |
| 6,253,764 B1 | 7/2001 | Calluaud | |
| 6,397,842 B1 * | 6/2002 | Lee | A61M 16/1045 55/497 |
| 6,807,964 B1 | 10/2004 | Ruddy | |
| 6,941,945 B2 | 9/2005 | Flodin | |
| 2002/0002976 A1 | 1/2002 | Smith et al. | |
| 2004/0094157 A1 | 5/2004 | Dantanarayana et al. | |
| 2005/0223795 A1 | 10/2005 | Gerder et al. | |
| 2008/0142013 A1 | 6/2008 | Hallett et al. | |
| 2008/0257358 A1 | 10/2008 | Stern et al. | |
| 2008/0283053 A1 | 11/2008 | Zucchi et al. | |
| 2009/0007917 A1 | 1/2009 | Hustveit | |
| 2009/0065729 A1 | 3/2009 | Worboys et al. | |
| 2009/0235936 A1 | 9/2009 | Blom | |
| 2010/0024824 A1 | 2/2010 | Chalvignac | |
| 2010/0108063 A1 | 5/2010 | Koch et al. | |
| 2010/0269827 A1 | 10/2010 | Rapoport | |
| 2011/0265799 A1 | 11/2011 | Lisogurski | |

FOREIGN PATENT DOCUMENTS

| | | |
|---|---|---|
| CN | 101310787 A | 11/2008 |
| CN | 101394888 A | 3/2009 |
| CN | 202-113452 U | 1/2012 |
| DE | 2406679 A1 | 8/1975 |
| DE | 3240897 A1 | 5/1984 |
| DE | 29613610 U1 | 12/1997 |
| DE | 20000369 U1 | 6/2001 |
| EP | 0112979 A2 | 7/1984 |
| EP | 0615764 A1 | 9/1994 |
| EP | 1994952 A1 | 11/2008 |
| FR | 2535613 A1 | 5/1984 |
| GB | 580146 A | 8/1946 |
| GB | 783434 A | 9/1957 |
| GB | 826280 A | 12/1959 |
| GB | 2053695 A | 2/1981 |
| GB | 2382639 A | 6/2003 |
| GB | 2433701 A | 7/2007 |
| GB | 2465358 A | 5/2010 |
| JP | S525999 Y2 | 2/1977 |
| JP | S56020467 | 2/1981 |
| JP | H10287403 A | 10/1998 |
| JP | 2000042109 A | 2/2000 |
| JP | 2001299916 A | 10/2001 |
| JP | 2008284370 A | 11/2008 |
| JP | 2008540056 A | 11/2008 |
| JP | 2009521982 A | 6/2009 |
| WO | WO-8904684 A1 * | 6/1989 |
| WO | 9206728 A1 | 4/1992 |
| WO | 9616689 A1 | 6/1996 |
| WO | 0038772 A1 | 7/2000 |
| WO | 20020051486 A1 | 7/2002 |
| WO | 2005097244 A1 | 10/2005 |
| WO | 2007075090 A1 | 7/2007 |
| WO | 2007030162 A3 | 11/2007 |
| WO | 2008028228 A1 | 3/2008 |
| WO | 2008114079 A1 | 9/2008 |
| WO | 2010116846 A1 | 10/2010 |
| WO | 2011035373 A1 | 3/2011 |
| WO | 2012048364 A1 | 4/2012 |

OTHER PUBLICATIONS

Extended European Search Report issued in European Patent Application No. 22179846.5 dated Nov. 10, 2022, 17 pages.
Office Action for Chinese Patent Application No. 201710862037.9, dated May 17, 2021.
Office Action for Japanese Patent Application No. 2020-113699, dated May 28, 2021.
Chinese Office Action issued in corresponding CN application No. 2017108620379 dated Aug. 28, 2019.
Chinese Office Action dated Jun. 10, 2020 for CN Patent Application No. 201710862037.9.
Chinese Office Action dated Nov. 10, 2020 for CN Patent Application No. 201710862037.9.
Office Action issued in corresponding Japanese Patent Application No. 2021-175373, dated Jun. 16, 2023, 6 pages.
Office Action issued in Japanese Patent Application No. 2021-175373, dated Mar. 3, 2023, 6 pages.

* cited by examiner

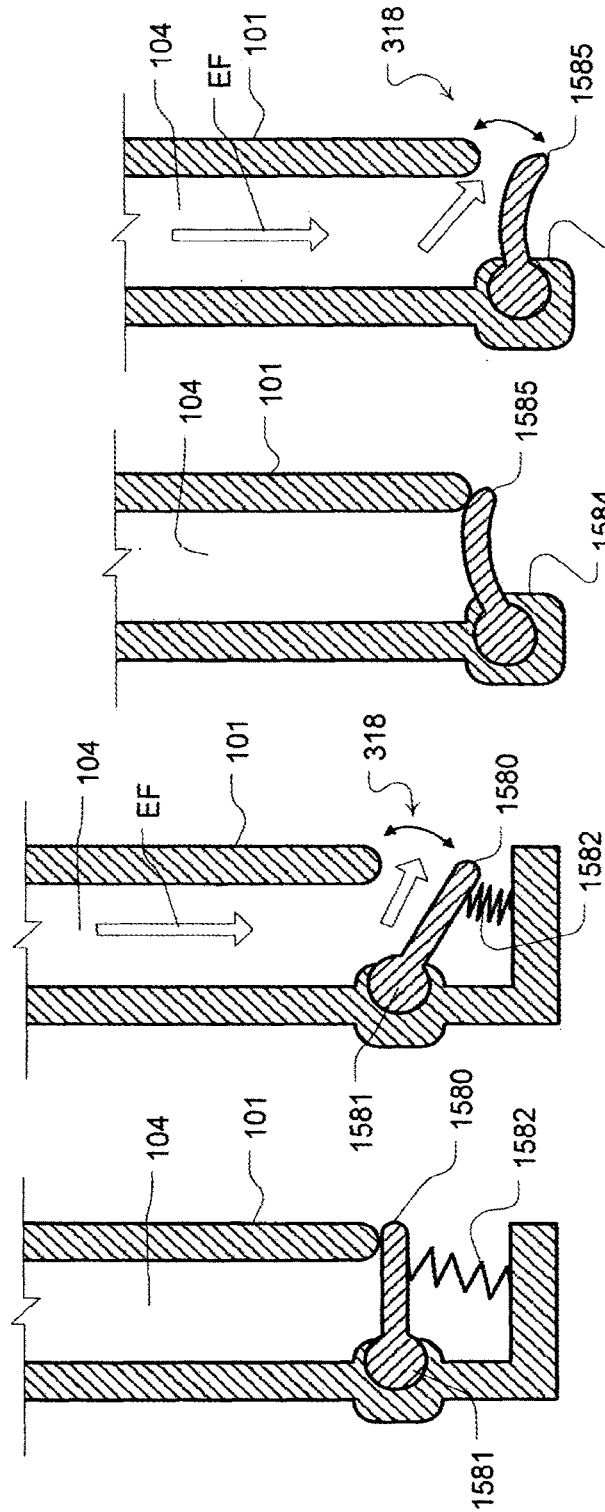

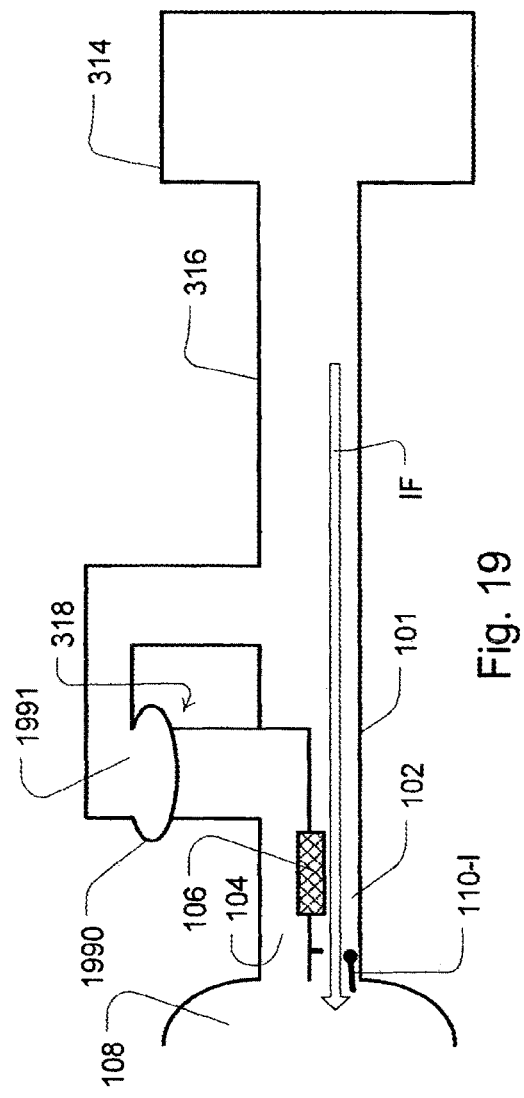
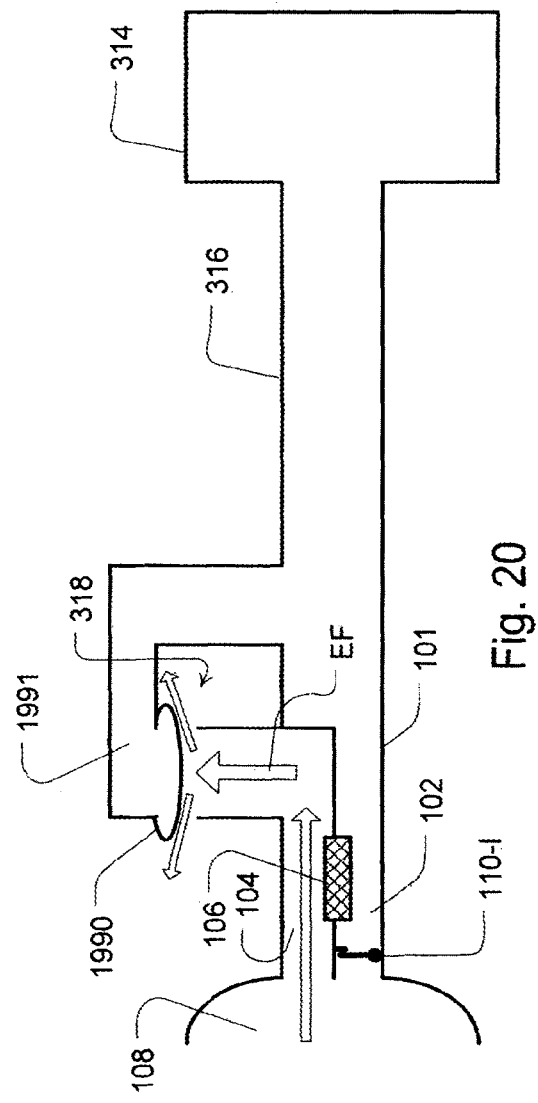

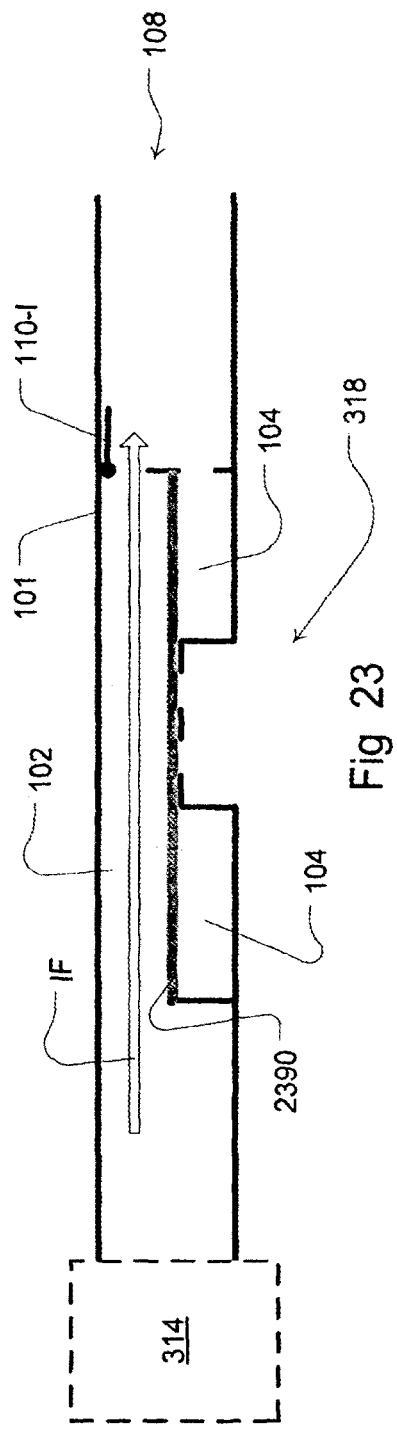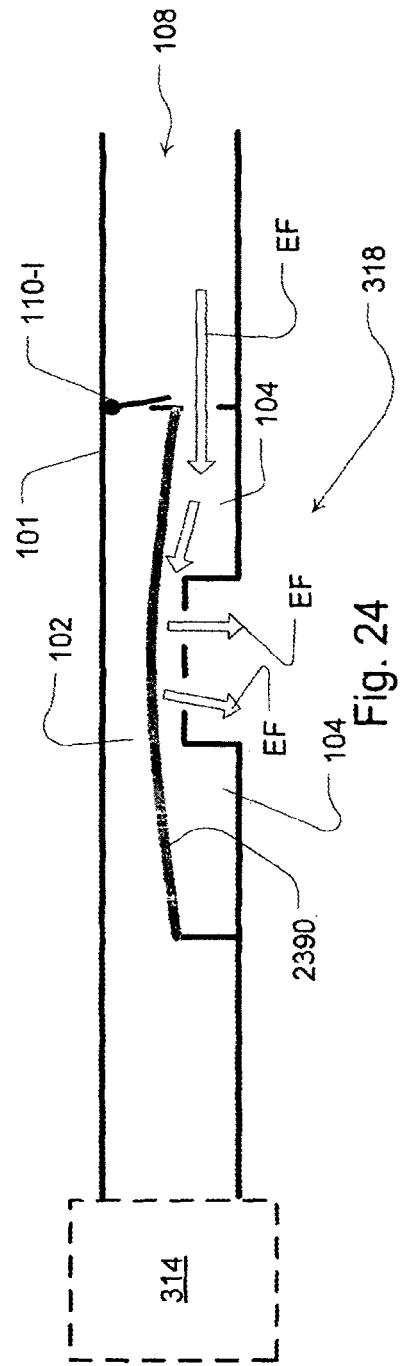

EXCHANGER ASSEMBLY FOR RESPIRATORY TREATMENT

CROSS REFERENCE TO RELATED APPLICATIONS

This application is a continuation of U.S. patent application Ser. No. 14/356,713 filed May 7, 2014, which is a national phase entry under 35 U.S.C. § 371 of International Application No. PCT/AU2012/001382 filed Nov. 9, 2012, published in English, which claims priority from U.S. Provisional Patent Application No. 61/558,648 filed Nov. 11, 2011, all of which are incorporated herein by reference.

FIELD OF THE TECHNOLOGY

The present technology relates to conduits for a respiratory treatment such as a conduit having a heat and/or humidity exchanger for a mask assembly that may be implemented for a respiratory pressure treatment including, for example, Non-invasive Positive Pressure Ventilation (NPPV) and continuous positive airway pressure (CPAP) therapy of sleep disordered breathing (SDB) conditions such as obstructive sleep apnea (OSA).

BACKGROUND OF THE TECHNOLOGY

Treatment of sleep disordered breathing (SDB), such as obstructive sleep apnea (OSA), by a respiratory treatment apparatus such as a continuous positive airway pressure (CPAP) flow generator system involves a delivery of air (or other breathable gas) at pressures above atmospheric pressure to the airways of a patient via a conduit and/or a mask. Typically, the mask fits over the mouth and/or nose of the patient, or may be an under-nose style mask such as a nasal pillows or nasal cushion style mask. Pressurized air flows to the mask and to the airways of the patient via the nose and/or mouth. A washout vent in the mask or conduit may be implemented to discharge the exhaled gas from the mask to atmosphere.

Respiratory treatment apparatus may include a flow generator, an air filter, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors may measure, amongst other things, motor speed, gas volumetric flow rate and outlet pressure, such as with a pressure transducer, flow sensor or the like. The controller may also include data storage capacity with or without integrated data retrieval/transfer and display functions. Positive airway pressure may be delivered in many forms.

As previously mentioned, a CPAP treatment may maintain a treatment pressure across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly replicate changes in the patient's breathing cycle. A pressure setting during expiration lower than inspiration may generally be referred to as expiratory pressure relief. As described by Sullivan in U.S. Pat. No. 4,944,310, positive airway pressure treatments typically provide gas under pressures to the patient in the range of 4 to 15 cmH$_2$O from the device and may involve flow rates of at about 120 liters/minute. Some of the air may escape via an end restriction or vent and not be delivered to the patient. These pressure settings may also be adjusted based on the detection of conditions of the patient's airway or respiration. For example, treatment pressure may be increased in the detection of partial obstruction, apnea or snoring. In some cases, positive airway pressure may be adapted to provide ventilation support. For example, a patient's ventilatory needs may be supported on a breath-by-breath basis by automatically calculating a target ventilation and adjusting the pressure support generated by an apparatus, such as a bi-level pressure treatment apparatus, so as to achieve the target ventilation.

Respiratory treatment apparatus are sometimes provided with accessory components for comfort conditioning of the flow or pressurized air supplied by the flow generator. For example, the supplied air may be applied to a humidifier to humidify and warm the treatment gas prior to its delivery to a patient. Similarly, various heating elements can be connected with a delivery conduit to help in maintaining a particular temperature of the supplied gas as it is conducted to the patient from a supply unit or humidifier.

There may be a desire to improve efficiency of heating and/or humidification and/or pressurised delivery of a breathable gas for respiratory treatments.

SUMMARY OF THE TECHNOLOGY

One aspect of the present technology relates to an exchanger configured to exchange a component of an inspiratory gas with a component of an expiratory gas.

Another aspect of the technology relates to a conduit configured with a heat and/or humidity exchanger.

A still further aspect of the technology relates to a conduit with an expiratory flow resistor.

Further aspects of the present technology relate to a respiratory treatment apparatus configured to deliver a respiratory treatment with such a conduit, expiratory flow resistor and/or exchanger.

Some such embodiments of the present technology involve conduits configured for dynamic expiratory venting.

Some embodiments of the present technology include an exchanger conduit to condition a breathable gas for a patient interface that delivers a respiratory treatment. The exchanger conduit may include a conduit having a first channel and a second channel. The first channel may be configured to conduct an inspiratory gas and the second channel may be configured to conduct an expiratory gas. The exchanger may be configured along the first channel and the second channel to separate the first channel and the second channel. The exchanger may also be configured to transfer a component of the gas of the second channel to the gas of the first channel.

In some such cases, the exchanger may include a temperature conducting material whereby the component of the gas transferred from the gas of the first channel to the gas of the second channel is temperature. In some such cases, the exchanger may include a moisture conducting material whereby the component of the gas transferred from the gas of the first channel to the gas of the second channel is moisture. In some such cases, the exchanger may include a hydrophilic material, a carbon dioxide rejecting material and/or a cellulose material. In some embodiments, the exchanger may include a folded surface that divides the first channel and the second channel. In some cases, the first channel and the second channel each include a plurality of flow pathways such that the exchanger divides the pathways with a plurality of generally parallel wall surfaces. Each such wall surface may separate a pathway of the first channel and a pathway of the second channel.

In some such embodiments, the exchanger may include a plurality of heat conducting fins. The exchanger may also include a plurality of capillary apertures. In some cases, the first channel may include an input end and an output end. The output end may be adapted for interfacing with a patient respiratory system. Optionally, in some such cases, the exchanger conduit may also include a valve. The valve may be configured at the first channel to permit gas flow through the first channel from the input end to the output end but not from the output end to the input end. In some cases, the output end may include a respiratory mask and/or a coupler for a respiratory mask.

In some such embodiments, the input end may include a coupler for an output conduit of a respiratory treatment apparatus. Optionally, the second channel may include an input end and an output end. The input end may be adapted for interfacing with a patient respiratory system and the output end may be adapted for interfacing with an expiratory vent to atmosphere. The second channel may include a valve to permit expiratory gas to vent to atmosphere through the expiratory vent and prevent a flow of air into the second channel from atmosphere through the vent. In some cases, the expiratory vent may include a flexible barrier. The flexible barrier may be preloaded with a tension to be operable to selectively open the vent to maintain pressure in the second channel below a pressure threshold that is greater than atmospheric pressure. In some such cases, the expiratory vent may include a pair of tensioning bars, through which the flexible barrier is tensioned.

In some cases of the exchanger conduit, the first channel may also include an input aperture with a coupler for an oxygen source. Optionally, in some cases, the exchanger may also include first and second sets of fins coupled together for temperature exchange. The first set of fins may extend within the first channel and the second set of fins may extend within the second channel. The first and second set of fins may be connected by a transverse portion having a capillary surface extending longitudinally along the first and second channels between the first and second sets of fins.

In some embodiments of the exchanger conduit, a fluid supply aperture may be included. The fluid supply aperture may include a fluid channel to supply a fluid to a material of the exchanger. In some embodiments, a conduit to the first channel may include a flexible chamber configured to prevent flow of an expiratory gas in the first channel. Optionally, a conduit to the second channel may include a flexible chamber configured to prevent flow of an inspiratory gas in the second channel.

In some embodiments, the exchanger may include a flexible divider. The flexible divider may have a fixed end. The flexible divider may also have a lip end. In some cases, the exchanger conduit may include a venting portion. The flexible divider may be configured to move to selectively block and open an aperture of the venting portion of the conduit. The venting portion may include a set of oblique apertures. The conduit may also include a ribbed divider support. The conduit may also include a divider seat configured for sealing with a peripheral edge of the divider.

In some embodiments, the exchanger may include an adjustment mechanism to selectively increase or decrease an efficiency of the transfer of the component of the gas of the second channel to the gas of the first channel. The adjustment mechanism may be configured to increase and/or decrease a flow contact surface area of the exchanger. In some cases, a processor and a sensor may be included. The processor may be configured to control the adjustment mechanism to adjust the efficiency of the exchanger in response to a signal from the sensor. The sensor may be temperature sensor or a humidity sensor.

Some embodiments of the present technology involve an expiratory flow resistor to permit a stenting pressure above atmospheric pressure in a respiratory conduit. The flow resistor may include a respiratory conduit having an expiratory flow channel. It may further include an aperture of the conduit to release a flow of the expiratory flow channel to atmosphere. It may also include a cover component. The cover component may be configured to selectively block the aperture and the cover component may be loaded with a tension to block the aperture unless a pressure of the expiratory flow channel exceeds a pressure threshold that is above atmospheric pressure.

In some such cases of the expiratory flow resistor, the cover component may be coupled to a spring and pivot, whereby the spring provides the tension to the cover component. Optionally, the cover component may be flexible and a wall abutment of the conduit may ply the flexible cover against the aperture to provide the tension to the cover component. In some cases, the cover component may include a balloon membrane wherein the conduit further include a pressurization chamber coupled to a flow generator to pressurize the membrane to expand to close the aperture.

In some cases of the expiratory flow resistor, the cover component may include a flexible membrane. Optionally, pressure of the expiratory channel may expand the membrane to open the aperture. In some embodiments, the cover member may include a flexible membrane, and the conduit may further include a set of bars through which the membrane is inserted to provide the tension to the membrane.

In some embodiments of the expiratory flow resistor, the conduit may include a holder ridge and the cover component may be further configured with the holder ridge to prevent flow into the expiratory channel unless a pressure condition in the expiratory channel falls below atmospheric pressure. In some cases, the cover member may also include a flexible membrane and a plug. The plug may be configured to selectively enter the aperture to block the aperture.

In some embodiments of the expiratory flow resistor, the conduit may also include an inspiratory channel that may be separated by the expiratory channel by the cover component. In some such cases, the inspiratory channel may be adapted to be coupled with an output of a flow generator of a respiratory treatment apparatus and an input of a patient interface. In some cases, the inspiratory flow channel may include a one-way valve to permit a flow generator to hold pressure in the inspiratory flow channel against the cover component without delivering flow to a patient interface through the inspiratory flow channel during patient expiration.

Some embodiments of the present technology may involve a conduit for a breathable gas for a patient interface that delivers a respiratory treatment. The conduit may have a first channel and a second channel. The first channel may be configured to conduct an inspiratory gas and the second channel may be configured to conduct an expiratory gas. The conduit may also include a flexible channel divider along the first channel and the second channel to dynamically create the first channel and the second channel in response to an inspiratory flow and an expiratory flow or a component of pressure resulting from an inspiratory flow or an expiratory flow such as a change in static pressure resulting from a change in lung volume or a dynamic pressure resulting from an inspiratory or expiratory flow velocity.

In some such cases, the flexible channel divider may include an exchanger to transfer a component of a gas of the first channel to the second channel. The component may be temperature and/or humidity. Optionally, the flexible divider may have a fixed end. The flexible divider may also have a lip end. In some cases, the conduit may include a venting portion such that the flexible divider is configured to move to selectively block and open an aperture of the venting portion of the conduit. The venting portion may include a set of oblique apertures, a ribbed divider support, and/or a divider seat configured for sealing with a peripheral edge of the divider. Optionally, in some cases, the conduit may also include a continuous vent aperture.

In some cases, the venting portion may include a set of apertures configured at an acute angle with respect to an expiratory flow path of the second channel. Optionally, the conduit may also include a conduit bend, and the flexible channel divider may extend across the conduit bend. In some cases, a length of the flexible channel divider may be a length greater than one and one quarter times a width of the conduit. The flexible divider may be configured in the conduit to provide the flexible divider with an expiratory activation side and a gas supply activation side, wherein the expiratory activation side has a surface area exceeding a surface area of the gas supply activation side. The flexible divider may also include a lift at a lip end of the divider and the lift may extend into a channel of the conduit. Optionally, the flexible divider may have a non-planar surface, such as a convex surface or a concave surface. The flexible divider may also include one or more protuberants configured to seal at least a part of the venting portion. Optionally, the conduit may include a secondary vent and a vent cover, and the flexible divider may be linked to the vent cover for selectively sealing the secondary vent. In some cases, the flexible channel divider of the conduit may include a duckbill opening. The duckbill opening may be configured to selectively block and unblock peripheral apertures of a venting portion of the conduit. In some cases, the conduit may also include a discrete venting chamber, and the flexible channel divider may have a pivot portion within the venting chamber. Such a flexible channel divider may selectively open the venting chamber to one of a venting portion for release of expiratory gas and a pressure release portion for equalizing gas of a gas supply with atmosphere.

In some cases, the conduit may include a bypass channel configured to permit a sensing of a gas characteristic to bypass the flexible channel divider. Optionally, the conduit may be coupled in gas communication with a sensor. The sensor may be configured to sense a gas characteristic attributable to the bypass channel. The sensor may be coupled with a processor. The processor may be configured to estimate a gas characteristic of an opposing side of the flexible channel divider from the sensed characteristic. The estimated characteristic may be patient expiratory flow and/or therapy pressure at a patient interface.

In some cases, the conduit may include an exchanger in series with the flexible channel divider. The conduit may also include a heat moisture exchange material in a bi-directional flow channel in series with the flexible channel divider. Optionally, the conduit may further include a set of divider supports extending from a conduit surface and positioned to support the divider during an inspiratory flow. In some cases, the conduit may further include a set of divider supports extending from a conduit surface and positioned to support the divider during an expiratory flow. The set of divider supports may be formed by parallel ribs longitudinally arranged along the flow path of the conduit.

In some cases, the flexible channel divider may be configured to create an inspiratory channel between a first side of the conduit and a first side of the divider and an expiratory channel between the opposing side of the conduit and the opposing side of the divider when the divider traverses between the opposing sides of the conduit.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

FIGS. 15 and 16 illustrate an example expiratory vent resistor that may be implemented in some conduit embodiments of the present technology;

FIGS. 17 and 18 illustrate a further flexible expiratory flow resistor that may be implemented in some conduit embodiments of the present technology;

FIGS. 19 and 20 illustrate a further flexible expiratory flow resistor that may be implemented in some conduit embodiments of the present technology;

FIGS. 23 and 24 illustrate operation of another flexible expiratory flow resistor that may be implemented in some conduit embodiments of the present technology;

DETAILED DESCRIPTION

Figure 1:
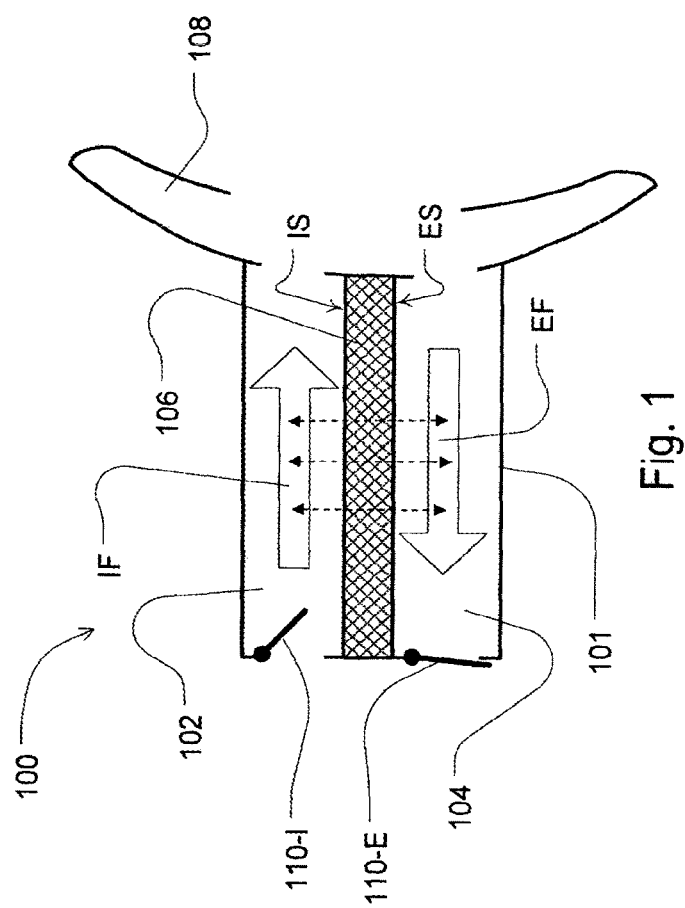
FIG. 1 is a diagram of a conduit apparatus with an exchanger of the present technology.

As illustrated in FIG. 1, some embodiments of the present technology may implement an exchanger, such as in a conduit for air or breathable gas that is directed to a respiratory system of a patient. The exchanger apparatus 100 may be coupled to or integrated with a patient interface 108, such as a respiratory nasal mask, nose and mouth mask, full face mask, endotracheal tube, cannula, nasal prongs, nasal pillows, etc. The exchanger 106 may be a component of a conduit assembly such as conduit 101. The conduit may be coupled with an output of a flow generator, such as a respiratory treatment apparatus, as discussed in other embodiments herein so that the conduit may direct a respiratory treatment to the patient. However, the conduit may more simply lead to atmosphere such that the conduit may more simply be used to condition ambient air for a user. In this regard, the exchanger may be implemented to condition the inspiratory flow with the expiratory flow or vice versa and may optionally do so without powered heating coils. Typically, the exchanger 106 will separate, or form a portion of a barrier that divides or separates, an inspiratory channel 102 and an expiratory channel 104 of the conduit 101. In this regard, these channels can provide a unidirectional flow characteristic such that each channel may be implemented to generally only conduct breathable gas in one direction. In this regard, in the case of the inspiratory channel 102, an inspiratory flow IF will be directed toward a patient interface end such that the inspiratory flow may be inspired by a user of the patient interface 108. Similarly, in the case of the expiratory channel 104, an expiratory flow EF will be directed away from the patient interface end such that the expiratory flow will have been expired by a user of the patient interface 108.

In some embodiments, the unidirectional flow of the channels may be maintained by optional valves. For example, at least one one-way valve may control the flow through the channels. As illustrated in the embodiment of FIG. 1, an inspiratory one-way valve 110-I permits air flow in the direction (shown as IF) from atmosphere to enter the inspiratory channel 102 but would impede or prevent a reverse of such air flow in the inspiratory channel. Thus, the inspiratory valve 110-I would be open during patient inspiration and closed during patient expiration. Similarly, an expiratory one-way valve 110-E permits air flow in the direction (shown as EF) to atmosphere (away from patient interface 108) so as to exit the expiratory channel 104 but would impede or prevent a reverse of the illustrated flow through the expiratory channel. Thus, the expiratory valve 110-E would be open during patient expiration and closed during patient inspiration.

As a result of the configuration of the channels and the exchanger 106, the exchanger will be exposed to inspiratory flow and expiratory flow but on opposing sides of the exchanger. In this sense, it will generally have an inspiratory side IS that is not generally exposed to expired air but only fresh inspired air or gas and an expiratory side ES that is not generally exposed to fresh air before inspiration but only expired air. Thus, the exchanger may conduct or transfer a component of either the expiratory gas or inspiratory gas to the other in association with these sides. For example, the exchanger may be configured to conduct heat to serve as a heat exchanger. In such a case, warm expired air of the expiratory channel 104 that may be warmed by the patient may contact the exchanger on an expiratory side ES. Thus, the expiratory air may warm the exchanger 106. The exchanger, which may be formed or extruded of a temperature conductive material such as silver, copper, gold, aluminium or a dust or composite of any of those materials etc., may conduct that heat energy to the inspiratory side IS. The inspiratory flow IF of the inspiratory channel 102 may then contact the inspiratory side IS and absorb the warmth that may be conducted, convected or radiated by the exchanger 106 if the inspiratory flow is cooler than the exchanger. In the case of a warm environment, the temperature of the exchanger may even potentially cool an inspiratory flow that is warmer than the expiratory flow.

Thus, the patient's own respiration may be applied to condition the temperature (e.g., heat or cool) of the inspired air through the exchanger. Moreover, since the inspiratory channel and expiratory channels are divided by the exchanger, the exchange of temperature may take place in a manner that minimizes potential for rebreathing of expired carbon dioxide. In this regard, the distinct inspiratory and expiratory channels may permit the exchange without substantially increasing dead space. Dead space may be considered the gas/space in the conducting areas of a respiratory system. In devices, such as the conduits of a respiratory treatment apparatus, it may refer to the same volume/space through which a patient is breathing. In a single pathway device where both inspiratory and expiratory gas flows to/from the patient, the patient may re-breathe some of the air previously breathed out. Having a dual/separate inspiration and expiration pathways, the patient is substantially consistently breathing in 'fresh' air from the inspiration pathway while breathing out to the distinct expiration pathway.

The exchanger, serving as a heat exchanger, may also reduce the output requirements or need for some heating components that are typically employed to warm fresh inspired air. For example, the use of the exchanger may reduce the size needed for heating coils or the energy used by such heating coils to heat inspired air to a comfortable temperature.

Similarly, in some embodiments, the exchanger may be implemented to transfer a moisture component of either the expiratory gas or inspiratory gas to the other. For example, expiratory flow EF may typically include a degree of moisture that may be greater than atmospheric air. The moisture of the expiratory flow may be absorbed by a material of the exchanger, such as a hydrophilic material, a capillary material, a cellulose membrane, or a hydrogel, a polysulfone ether, a bio-compatible polymer, etc. The moisture may condense on a surface of a material of the exchanger on the expiratory side ES of the exchanger 106. The moisture may then transfer through the exchanger 106 to the inspiratory side IS. Inspiratory flow IF across the surface of the inspiratory side IS of the exchanger may then permit the moisture to evaporate into the inspiratory flow IF of the inspiratory channel. In some embodiments the exchanger may be formed by a hydrophilic material or coating on one side and a hydrophobic material or coating on the other such as to promote the absorption of liquid in one channel and the evaporation of liquid in the other. For example, the inspiratory channel side of the exchanger may have a hydrophobic material or coating and the expiratory channel side of the exchanger may have a hydrophilic material or coating. In the case of a warm environment, the humidity exchanger may even potentially cool an inspiratory flow that is warmer than the expiratory flow. In the case that liquid is transferred from one flow channel to another flow channel such as in the case where moisture is condensed in the expiratory flow channel and transferred to the inspiratory flow channel in liquid form, the exchanger may take advantage of evaporative cooling as the liquid is vaporised by the flow in either channel, for example in the inspiratory channel, to cool the inspiratory gas.

Thus, the exchanger, serving as a humidity exchanger, may be implemented to condition the humidity of the inspiratory flow from the humidity of the expiratory flow. Moreover, since the inspiratory channel and expiratory channels are divided by the exchanger, the exchange of humidity may take place in a manner that minimizes potential for rebreathing of expired carbon dioxide or without substantially increasing dead space as previously mentioned. The exchanger, serving as a moisture exchanger, may also reduce the output requirements or need for some humidification components that are typically employed to humidify inspired air. For example, the use of the exchanger may reduce the quantity of reservoir water needed for a humidifier. Similarly, it may also reduce the energy used by heating coils that heat water to humidify inspired air.

In some embodiments, one or more materials of the exchanger may be treated or chosen for particular performance characteristics. For example, as previously mentioned, the exchanger may include coatings of hydrophobic and/or hydrophilic materials. In some embodiments, a material of the exchanger may be coated to reduce carbon dioxide transfer or diffusion through the material. For example, an anti-carbonation coating may be applied to an exchanger material such as a cellulose membrane or a poly sulfone ether material. Such a barrier coating may still permit a transfer of water while impeding a transfer of carbon dioxide.

In some embodiments, the efficiency of the exchanger may be controlled, e.g., manually or automatically, to satisfy a patient's preferences. For example, in some embodiments the exchanger may be adjustable to permit greater and lesser surface area of the exchanger to be contacted by inspiratory and/or expiratory flow. In such as case, greater surface area may permit more humidity or temperature transfer and less surface area may permit less humidity or temperature transfer. For example, in embodiments utilizing fins as discussed herein, an adjustment mechanism, such as a rotary control, slider, motor or solenoid, may withdraw or extend less or more of the area of fins into the channels of the conduit. Similarly, an adjustable cover(s) may extend or retract to different degrees to provide a movable barrier or insulator on one or more portions of the exchanger to change the contact area of the exchanger that can contact the flow in one or more channels of the conduit to impede the exchanger's efficiency to varying degrees. In some cases, automated control of the adjustment mechanism may involve evaluation, such as by a processor-based controller, of signals from one or more sensors, such as a humidity and/or temperature sensor that may be located proximate to either channel of the conduit, in the setting of the portion or size of the area of the exchanger that can participate in the exchange transfer. The controller or processor, which may also be a controller of a flow generator, may be configured and adapted to implement the control methodologies. Thus, the controller may include integrated chips, a memory and/or processor control instructions or data in an information storage medium. For example, programmed instructions encompassing the control methodology may be coded on integrated chips in the circuits or memory of the device or such instructions may be loaded as software or firmware using an appropriate medium containing the instructions or data.

Figure 2:
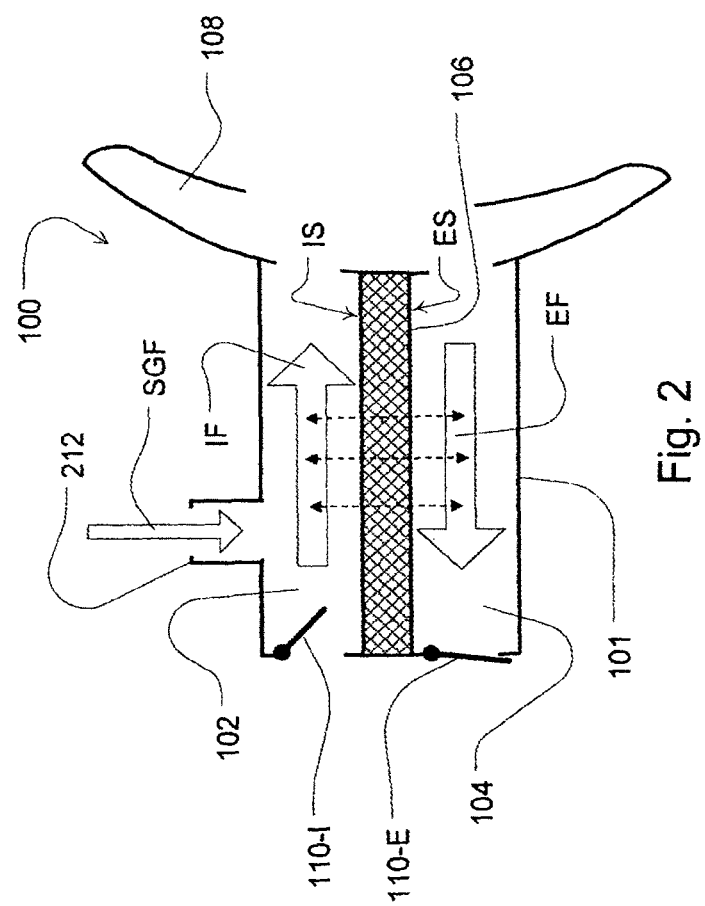
FIG. 2 is a diagram of another embodiment of the conduit apparatus of FIG. 1.

As previously mentioned, some embodiments of the exchanger apparatus 100, whether implemented for temperature or humidity exchange or both, may be configured for different respiratory purposes. For example, as illustrated in FIG. 2, the inspiratory channel 102 may include a supplemental gas source input port 212. In such an embodiment, the input port 212 may include a coupler for coupling with a supply tube of a supplemental gas source, such as an oxygen source. In such an embodiment, the expiratory flow EF may then serve to condition the inspiratory flow IF that includes the supplemental gas and air through the implementation of the exchanger 106.

Figure 3:
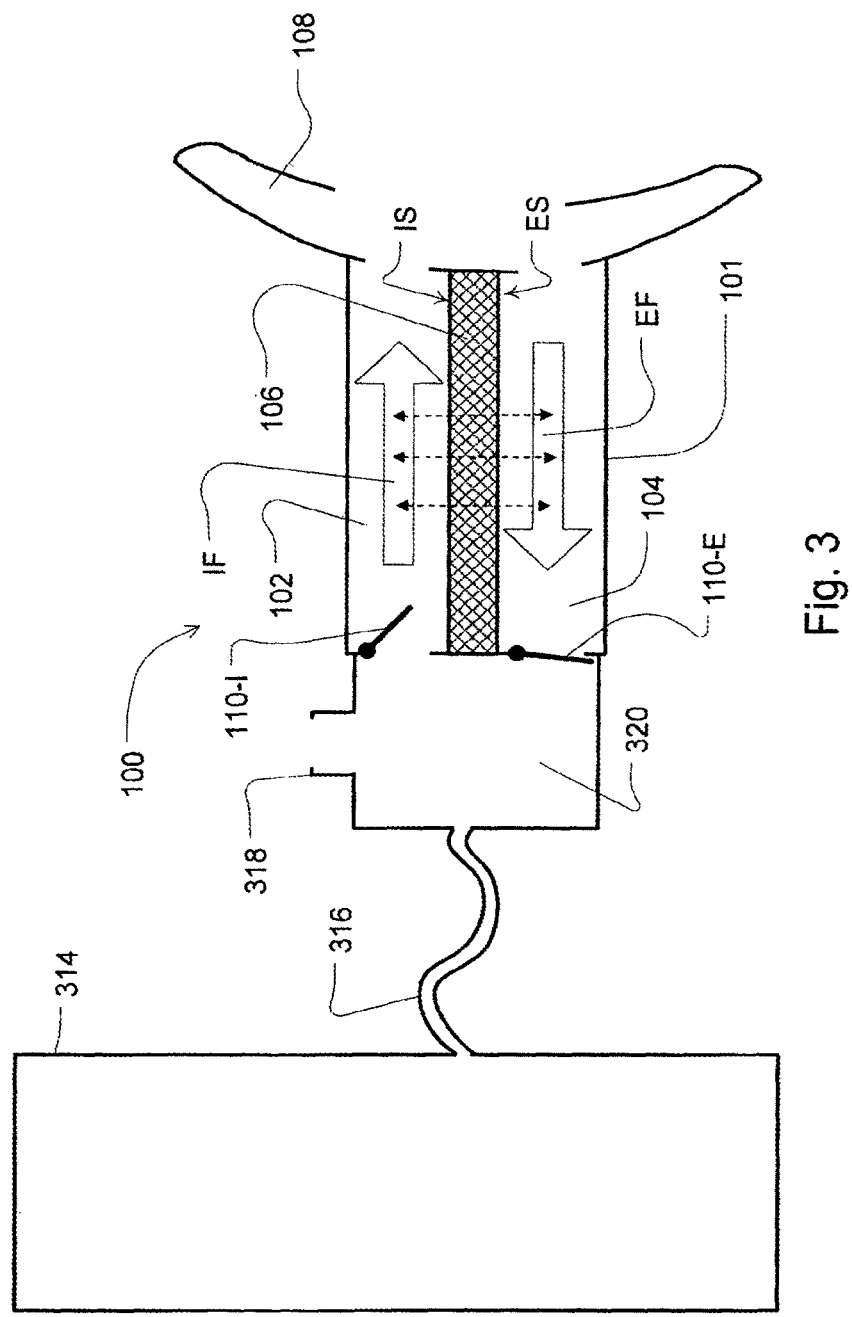
FIG. 3 is a diagram of an embodiment of the conduit apparatus having an exchanger of the present technology that is suitable for implementation with a respiratory treatment apparatus.
Figure 4:
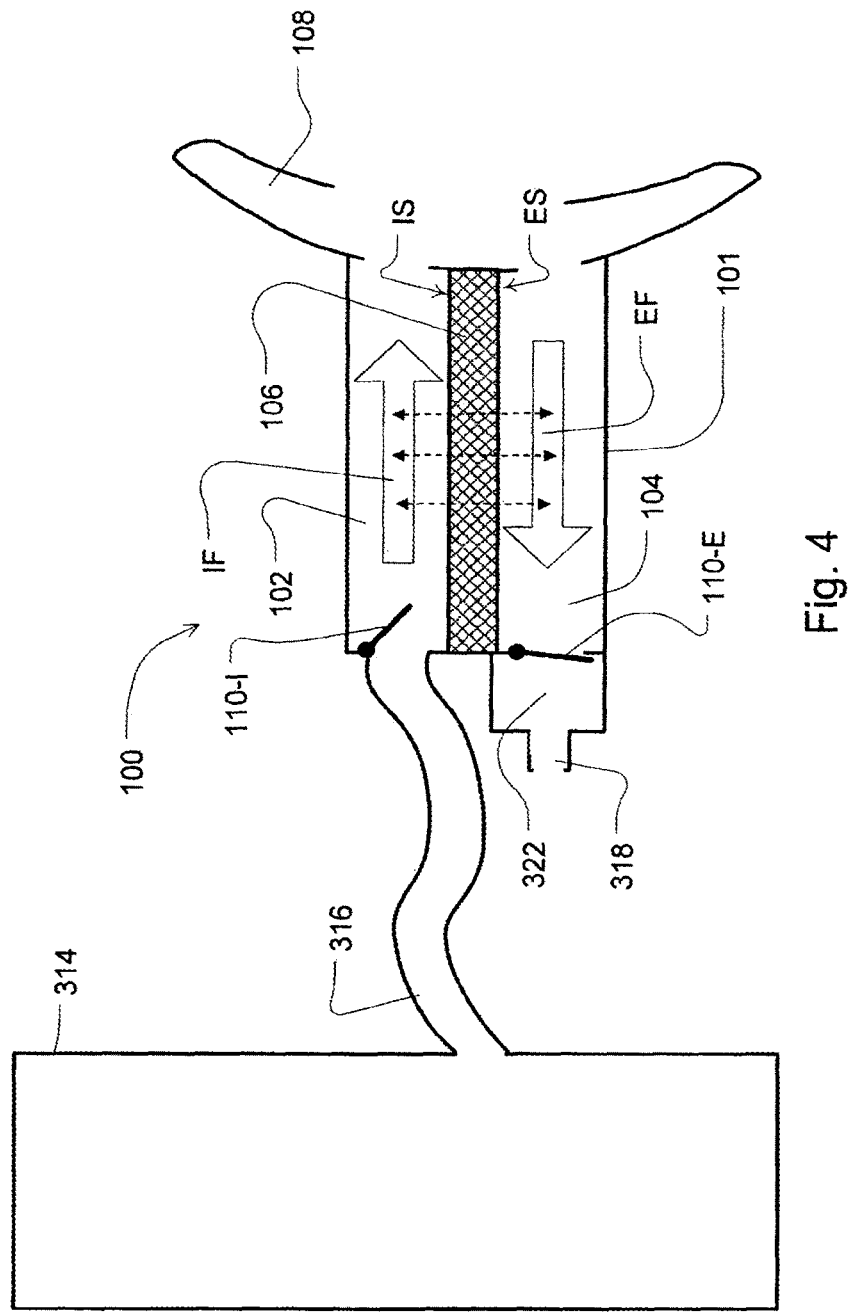
FIG. 4 is a diagram of another exchanger embodiment suitable for use with a respiratory treatment apparatus.
Figure 5:
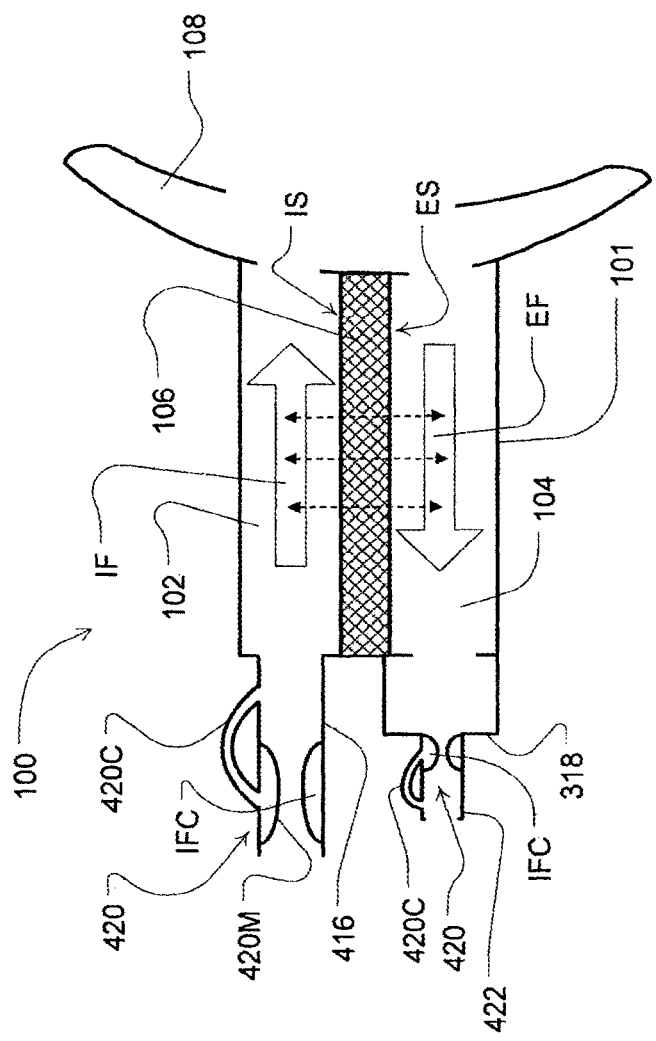
FIG. 5 is a diagram of an alternative embodiment of the embodiment of FIG. 4 with a Starling resistor.

The embodiments of FIGS. 3, 4 and 5 illustrate various implementations of the exchanger apparatus 100 and may include a respiratory treatment apparatus that includes a flow generator 314. As illustrated in the version of FIG. 3, a supply conduit 316 from an output of the flow generator (e.g., a blower output) may be coupled with a pressurized chamber 320 having a vent 318 for expiration. The supply conduit may deliver a flow of breathable gas, e.g., air, at a pressure above atmospheric pressure that is generated by the flow generator to the pressurized chamber 320. The vent 318 may serve as a washout vent or flow limiter. The pressurized flow from the flow generator may pass through the inspiratory channel 102 but not the expiratory channel 104 when the patient's inspiration opens the inspiratory valve 110-I. Patient expires through the expiratory channel 104 when the patient's expiration increases the pressure in the expiratory channel above the pressure of the chamber 320. The expired flow then proceeds through the chamber to exit the vent 318 to atmosphere. Thus, in this embodiment both air to be inspired and expiratory air traverse through chamber 320.

The embodiment of FIG. 4 is similar to that of FIG. 3. However, in this version, the chamber 322 does not directly couple with the supply conduit 316. The supply conduit 316 is coupled to an input of the inspiratory channel 102. The vent 318, via chamber 322, is coupled to the expiratory channel. Accordingly, in this embodiment, expired air from the expiratory channel is not introduced to any conduit that supplies breathable gas to the inspiratory channel 102.

The embodiment of FIG. 5 is similar to the embodiment of FIG. 4 and may be implemented without a flow generator as shown. However, in the illustrated embodiment, one or more of a Starling resistor 420, a variable or adjustable vent 422 or any of the flow resistors described in more detail herein, may replace the one-way valves. For example, as shown, a Starling resistor 420 may be implemented in a flexible portion of the supply conduit 316 to regulate flow into the inspiratory channel. Similarly, an adjustable vent 422 implemented with a Starling resistor 420 may serve in lieu of the expiratory valve 110-E. Any known variable or adjustable vent may be implemented. For example, any of the vent assemblies described in U.S. Provisional Patent Application No. 61/534,044, filed on Sep. 13, 2011, the entire disclosure of which is incorporated herein by reference, may serve as the adjustable vent 422. By operation of the resistor(s) and/or controlling an adjustable vent, flow through the channels may be regulated to direct the inspiratory flow through the inspiratory channel 102 and the expiratory flow through the expiratory channel 104. For example, pressure swings in the mask may be detected to set the adjustable vent for greater flow during expiration to permit expired air to flow through the expiratory channel to the adjustable vent during expiration. Based on the pressure swings, the adjustable vent may then be set for less or no flow during inspiration so as to permit inspiration flow from a flow generator through the inspiratory channel to the patient for inspiration.

Figure 5B:
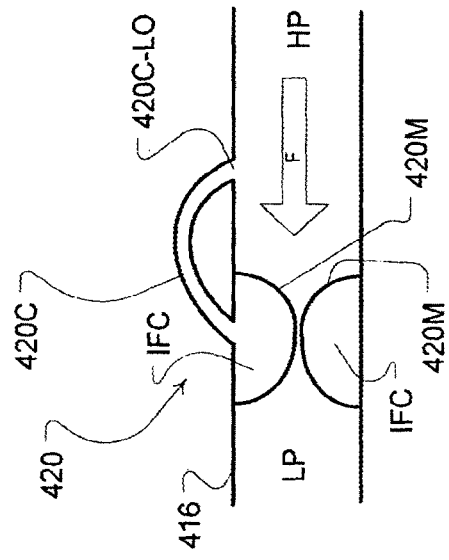
FIGS. 5A and 5B illustrate operation of a Starling resistor in a conduit that is implemented as a one-way valve shown in both open and closed configurations respectively.
Figure 5A:
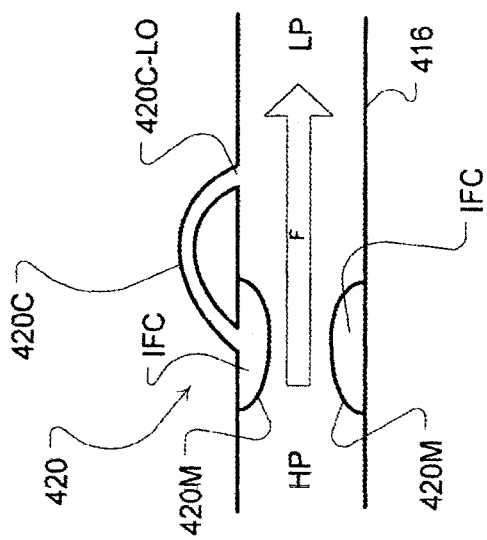

Operation of the Starling resistor 420 may be considered in conjunction with the illustrations of FIGS. 5A and 5B. In this embodiment, the Starling resistor in a conduit 416 employs a chamber link conduit 420C. The chamber link conduit 420C provides a pneumatic link to an inner flexible chamber IFC formed by the flexible membrane 420M within the conduit 416. As illustrated in FIG. 5A, when a lower pressure LP condition in the conduit exists proximate to the link opening end 420C-LO of the link conduit 420C with the higher pressure HP condition in the conduit on the opposing side of the flexible chamber IFC, the flexible chamber will contract to permit flow through the channel of the conduit. As illustrated in FIG. 5B, when a higher pressure HP condition in the conduit exists proximate to the link opening end 420C-LO of the link conduit 420C with the lower pressure LP condition in the conduit on the opposing side of the flexible chamber IFC, the flexible chamber will expand to resist or impede flow through the channel of the conduit. Accordingly, depending on the location of the link opening end 420C-LO of the link conduit 420C, the conduit with the Starling resistor may be selectively implemented to limit flow to either inspiratory flow or expiratory flow as previously described. Alternatively, the membrane chamber may be selectively activated by a pneumatic link to an output of a flow generator rather than using the link conduit 420C as illustrated in FIG. 5.

Figure 6:
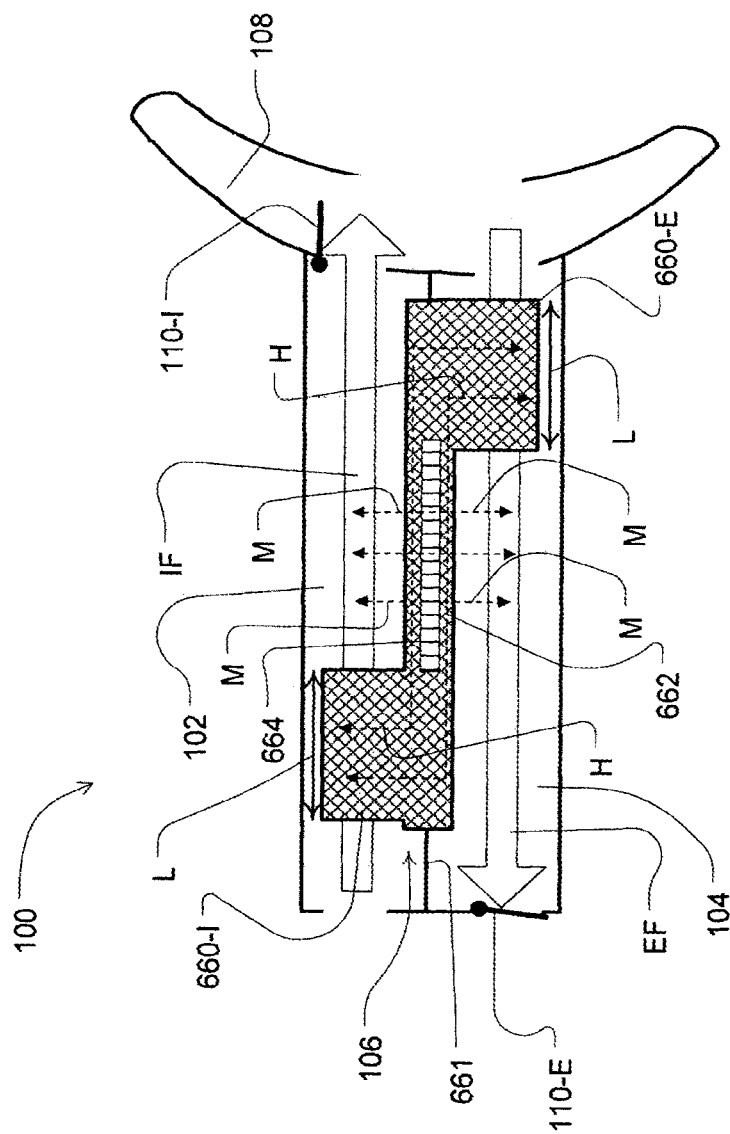
FIG. 6 is a diagram of an example heat and humidity exchanger suitable for use in some embodiments of the present technology.
Figure 8:
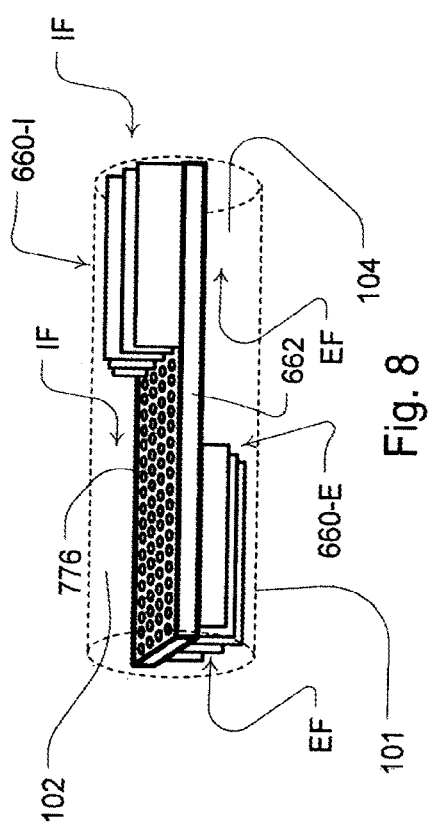
FIG. 8 is an illustration of an exchanger having conduction fins and a capillary medium for humidity transfer that may be implemented in some embodiments.

FIG. 6 illustrates a further example exchanger embodiment for both humidification (labelled as "M" in FIG. 6) and temperature (labelled as "H" in FIG. 6) exchange. In this embodiment, the exchanger includes a heat exchange portion having sets of fins that may be configured for temperature exchange. The fins may extend into the inspiratory channel 102 and/or expiratory channel 104 to increase the surface area by which the conduit flow contacts the exchanger. In this example, one or more inspiratory fins 660-I extend within the inspiratory channel and one or more expiratory fins 660-E extend within the expiratory channel 660-E. Flow passing on either side of each fin creates additional flow paths within each channel such that flow may then contact two sides of one or more of the fins permitting a greater transfer of heat energy. By using narrow width fins that have their lengths ("L") positioned substantially parallel to the flow of the channel, the flow through the channel may pass more easily along the fins to increase the surface contact area while not introducing a significant resistance to flow through the fin portion of the channel. A further example of such an exchanger is illustrated in FIG. 8.

While the fins may be located substantially directly across the channel barrier 661 between the inspiratory and expiratory channels, in this embodiment, the fins may include a transverse portion 662 that connects the inspiratory fins with the expiratory fins. As illustrated in the embodiment of the FIG. 6, the transverse portion may extend along the channel barrier and may form a portion of it, and it may be generally parallel to the flow of each channel. The transverse portion can permit the expiratory fins to be located more proximate to a patient interface 108 end of the expiratory channel and the inspiratory fins to be located less proximate to the patient interface 108 end of the inspiratory channel. Typically, the transverse portion will be formed of the same or similar heat conducting materials as the fins to permit the transfer of heat energy between the sets of expiratory and inspiratory fins.

Figure 9:
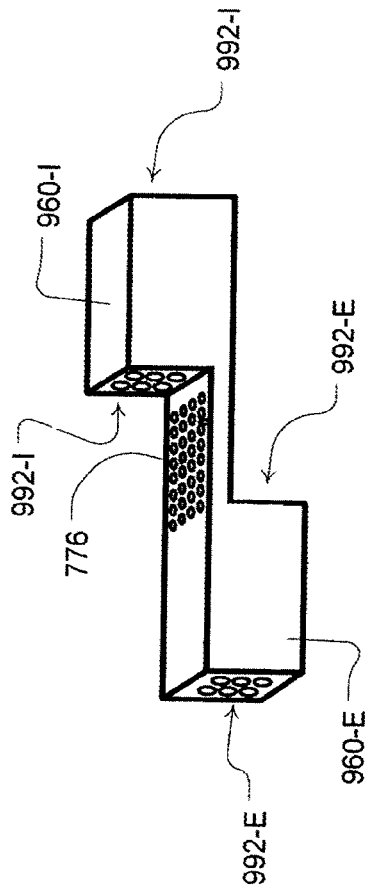
FIG. 9 is an illustration of an exchanger having multiple heat conduction channels for inspiratory and expiratory flow and a capillary medium for humidity transfer that may be implemented in some embodiments.
Figure 7:
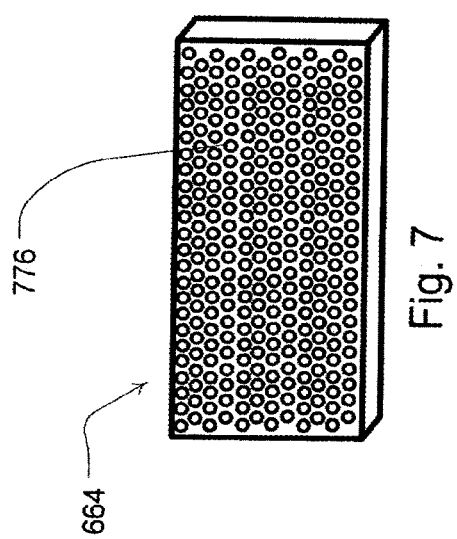
FIG. 7 is an illustration of a capillary humidity exchanger that may be implemented in some embodiments.

Optionally, the exchanger 106 also includes a humidity exchange portion 664. For example, the humidity exchange portion may be located within one or more apertures of the exchange portion. As previously described, the humidity exchange portion in some embodiments may include a capillary section configured with fine bores to permit a capillary transfer of liquid from the expiratory channel to the inspiratory channel through or between the transverse portion. An example of a capillary section 776 for a humidity exchange portion is also illustrated in FIGS. 7, 8 and 9. Optionally, the humidity exchange portion may alternatively, or also, be located between the expiratory fins and/or the inspiratory fins. In the exchanger version of FIG. 8, the capillary section 776 includes fine bores that extend through to apertures between the fins 660-I, 660-E as well as on the transverse portion 662.

In the exchanger of FIG. 9, the capillary section 776 may be limited to the transverse portion. As an alternative to fins, the exchanger may include temperature conducting blocks 960-I, 960-E. Each block may include a plurality of flow passages that may be substantially parallel to each other. The flow passages may be formed by holes through each block. In such a case, the holes of the block will be larger than the apertures of the capillary section so as not to substantially impede flow through the block. Thus, an inspiratory block 960-I may permit the inspiratory flow to traverse through its inspiratory block passages 992-I for a temperature exchange with inspiratory flow. Similarly, an expiratory block 960-E may permit the expiratory flow to traverse through its expiratory block passages 992-E for a temperature exchange with expiratory flow. The additional passages through the holes in each block of the channel can permit an increase in surface contact area with the heat conducting material of the block and thereby a more efficient transfer of heat energy. Although holes are shown through the blocks, the structure of the block may be replaced by a matrix or mesh channel having multiple pathways through a portion of the exchanger to otherwise increase the contact area of the exchanger. Moreover, although the blocks are illustrated as rectangular in FIG. 9, the blocks may be shaped to conform to the shape of any conduit with which the exchanger is implemented.

Figure 10A:
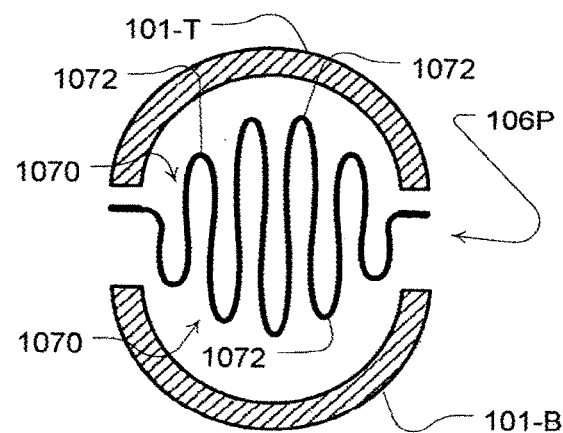
FIGS. 10A and 10B are cross sectional views of an example conduit and folded exchanger configuration with inspiratory and expiratory channels in an example embodiment of the present technology.
Figure 10B:
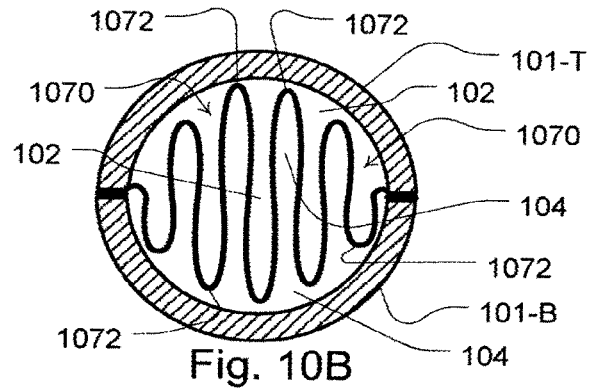
Figure 12A:
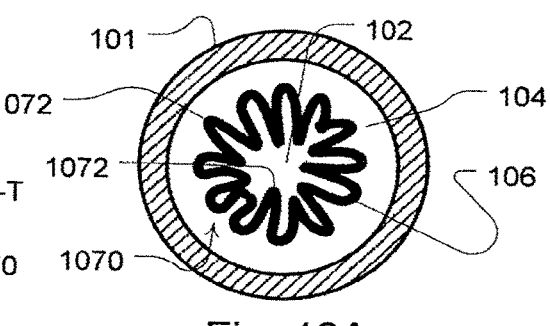
FIG. 12A is a cross sectional view of the conduit and exchanger including a pleated channel.
Figure 12:
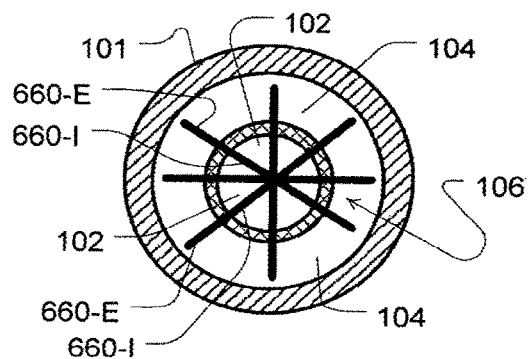
FIG. 12 is a cross sectional view of the conduit and exchanger of FIG. 11 including temperature conducting fins.
Figure 13:
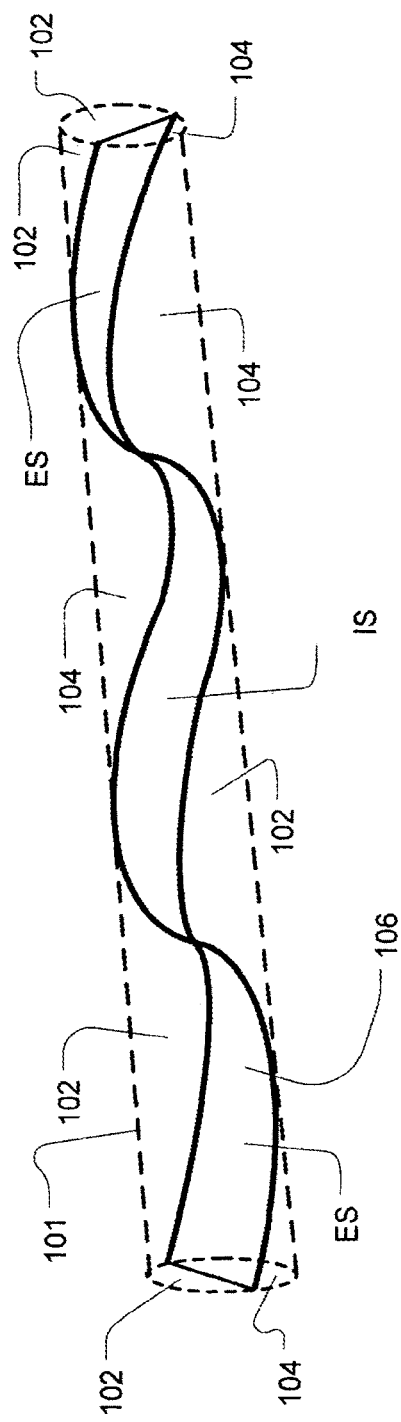
FIG. 13 illustrates a helical exchanger conduit embodiment of the technology.

To this end, some exchanger embodiments of the present technology may be implemented in conduits having a generally tubular form such as a tube. However, other conduit configurations may also be implemented. For example, the channels and exchanger may be implemented as an integrated conduit of a patient interface. In FIGS. 10A, 10B, 11, 12, 12A and 13 some example tubular exchanger conduits are illustrated. FIGS. 10A and 10B show cross-sectional views of an example of a pleated exchanger 106P. The exchanger 106 of this embodiment is implemented with a plurality of folds 1070 each with a crease 1072 that runs generally along or parallel to the flow through the channels of the conduit or parallel to the length of the conduit. As illustrated in the figures, in some embodiments, the exchanger may be inserted into a top conduit portion 101-T and a bottom conduit portion 101-B. When assembled, as illustrated in FIG. 10B, the top conduit portion and exchanger may form a first channel for conduit flow, such as the inspiratory channel 102. Similarly, the bottom conduit portion and the exchanger may form a second distinct channel for conduit flow, such as the expiratory channel 104. In this way, the folds of the exchanger 106 can provide a greater contact surface area for the exchanger along the channels.

Figure 11:
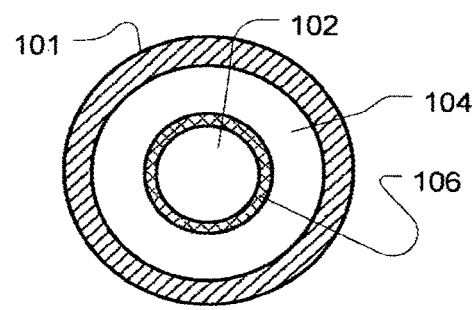
FIG. 11 is a cross sectional view of a further conduit and exchanger with inspiratory and expiratory channels in some embodiments of the present technology.

In the cross-sectional view of the embodiment of FIG. 11, the exchanger 106 is formed as a conduit with the exchanger material serving as the surface structure of the conduit. Thus, the exchanger may be formed with a tubular shape such as a tube. The tubular exchanger 106 may be positioned within a larger conduit. In such an embodiment, the flow of outer channel may substantially flow along the circumferential periphery of the exchanger to increase surface area contact. For example, the inner surface of the outer conduit 101 and the outer surface of the exchanger 106 may form the inspiratory channel 102. In such a case, the inner surface of the exchanger would then form the barrier of the expiratory channel 104. This is the example illustrated in FIG. 11. However, in some embodiments, the inner surface of the outer conduit 101 and the outer surface of the exchanger 106 may form the expiratory channel 104. In such a case, the inner surface of the exchanger would then form the barrier of the inspiratory channel 102. In such embodiments, the exchanger may also be implemented with folds and/or with fins. For example, as illustrated in the cross sectional view of the exchanger conduit of FIG. 12, a plurality of heat conducting fins may extend across the channels to form inspiratory fins 660-I and expiratory fins 660-E. By way of further example, as illustrated in the cross sectional view of the exchanger conduit of FIG. 12A, a plurality of folds of the exchanger provide a circumferential periphery of an inner channel that may be the inspiratory channel 102, as well as an inner boundary for an outer channel that may be the expiratory channel 104.

In some embodiments, the inspiratory channel and/or expiratory channel may be implemented in a less linear fashion from the linear version shown in FIG. 8. For example, the channels and the exchanger may be implemented with a spiral or helical configuration to increase surface contact area. In some such embodiments, an inner channel, such as an inspiratory channel formed by the exchanger, may spiral centrally through a more linear outer expiratory channel of a conduit. In a further example illustrated in FIG. 13, the channels may both spiral together in a helical configuration. For example, an exchanger 106 that forms a divider barrier that splits the conduit along its length, may be twisted along the conduit length to form a spiral barrier such that inspiratory channel 102 and expiratory channel 104 both spiral on opposing sides of the conduit along the conduit length. Such a spiral formation may yield an increase in exchanger surface contact area and may promote contact with the exchanger by creating flow turbulence along the exchanger.

Figure 14:
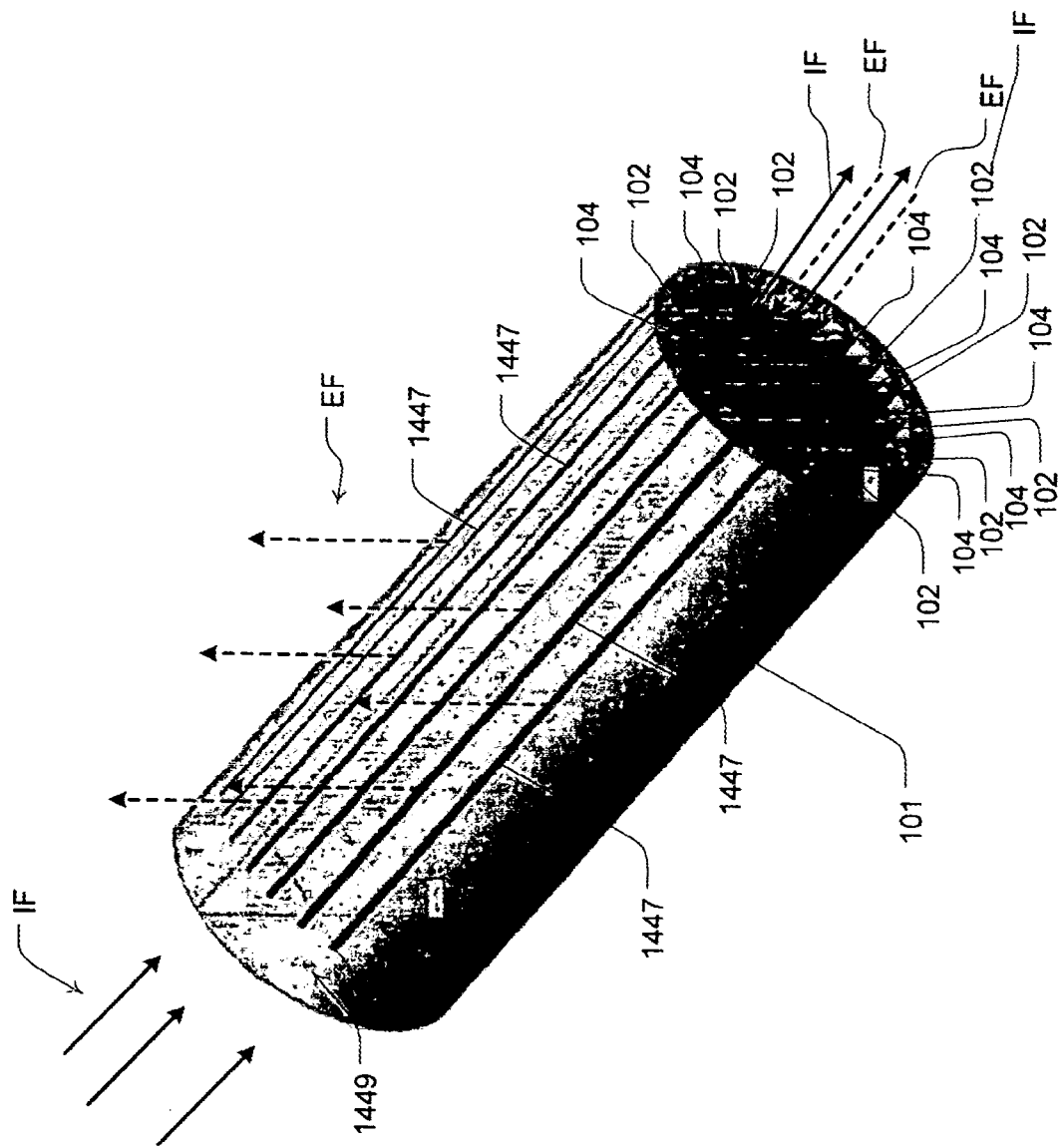
FIG. 14 shows a still further exchanger conduit embodiment having multiple flow paths.

In some embodiments, the expiratory and inspiratory fins of the exchanger may serve as channel dividers such as in the example embodiment of FIG. 14. In this embodiment, the channels may be interleaved by fins that extend substantially across the cross section of the conduit. In this version, each fin divides an inspiratory channel 102 and an expiratory channel 104 such that the inspiratory channel and expiratory channel are on opposing surface faces of each fin. Optionally, grooves 1447 that extend along length of the conduit may provide an escape vent to atmosphere for expiratory flow from the expiratory channels. Thus, each groove 1447 may be a cut through the conduit 101 to an expiratory channel 104. The expiratory channels 104 may be closed at a closed end 1449.

In some embodiments, it may be useful to supply moisture to an exchanger before or during use. For example, a fine bore liquid supply tube may extend from a reservoir, such as a bag, bottle or a container of a respiratory treatment apparatus. The tube may be configured with one end at or in a material of the exchanger to drip a liquid (e.g., water) on the exchanger. The small tube may operate by the Venturi effect to add water from the reservoir into the inspiratory flow path or the inspiratory side of the exchanger to humidify the inspiratory flow. For example, as water evaporates from the inspiratory side of the exchanger as a result of the inspiratory flow, more water from the liquid supply tube may then drip into the exchanger.

In some cases, the exchanger may include or be near a heating element, such as for warming inspired air. For example, a thermoelectric device such as a Peltier device may be included in a channel of the conduit of the exchanger. The thermoelectric device may be powered by an internal or external battery or other power source, such as the external power source of a flow generator.

Expiratory Venting

In the case of implementing distinct inspiratory and expiratory channels with a patient interface that may provide a pressure treatment, such as for providing a pressure above atmospheric pressure during expiration to stent a patient airway, it may be useful to include a device to regulate pressure within the expiratory channel particularly if the inspiratory channel to a flow generator will be closed during patient inspiration. For example, the channel may be implemented with an expiratory flow resistance component to provide a level of resistance that raises or maintains some pressure above atmospheric pressure in the expiratory channel, and as well as the patient interface, during expiration. Such a resistance/impedance component may be designed by varying constructions of the length/shape of the pathways and the size/width of the pathways. Examples may be considered in reference to the expiratory flow resistors illustrated in FIGS. 15 to 25, which might or might not be implemented with any of the expiratory channels or vents described herein and might or might not be implemented with any of the exchangers described herein. This style of venting, such as the venting described in reference to the components of FIGS. 15-18, may be particularly suited to a gas delivery system with a constant blower rotational speed, or a high impedance circuit, for example, a long and narrow tube to allow for less therapy pressure fluctuation.

In the embodiment of FIGS. 15 and 16, a rigid vent cover 1580 may be movable on a pivot 1581. A biasing member, such as a spring 1582, may be coupled to the rigid vent cover 1580. The biasing member provides a bias to the rigid vent cover 1580 such that it may be preloaded with a resistance when closed as shown in FIG. 15. The bias may provide a desired load or pressure threshold that will permit a desired level of pressure to build or be maintained in the expiratory channel 104 during patient expiration before the rigid vent cover will yield to a patient generated increase in expiratory pressure. Similarly, the size of the opening permitted by the biased vent cover may be regulated by the biasing member to maintain a level of pressure within the expiratory channel 104 during at least a portion of patient expiration even as expired flow exits the expiratory channel 104 through the vent 318 when open as illustrated in FIG. 16.

The expiratory flow resistor embodiment of FIGS. 17 and 18 operates in a similar manner to that of the embodiment of FIGS. 15 and 16. In this embodiment, a flexible flap may serve as the vent cover and might not utilize a pivot. For example, a flap holder 1584, such as an abutment of the conduit wall, can ply the flap member against the vent to bias the flexible flap 1585 with a tension into its closed position as illustrated in FIG. 17. The bias must be overcome by expiratory pressure in the expiratory channel 104 for the expired air to escape from the vent 318.

In other words, in these embodiments, the bias of the cover or flexible flap of the vent may be chosen so that the cover or flap will start to open when the pressure differential times the area of the flap or cover is greater than the compression force in the spring (or the deflection times the spring constant of the flap). Thus, in typical embodiments, this means that below this prescribed pressure differential, which may serve to provide a stenting pressure during expiration, the vent will be closed. Consequently, it will also be closed during inhalation.

Figure 51:
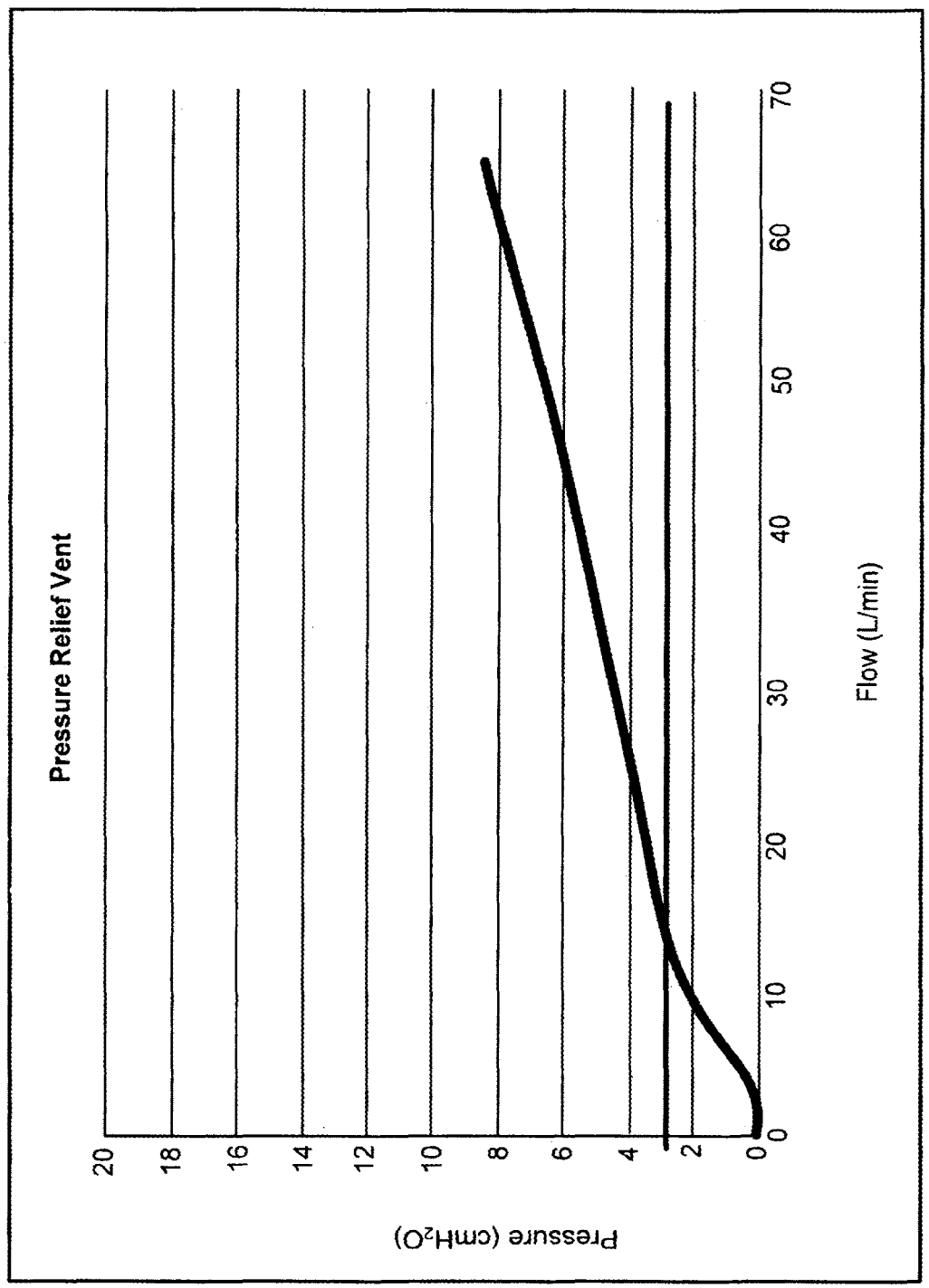
FIG. 51 is a pressure vs. flow graph illustrating example venting flow characteristics with an expiratory vent resistor such as the resistors of FIGS. 15 through 19.

In some cases, the bias may be chosen to yield venting with the pressure (P) and flow (Q) characteristics as illustrated in FIG. 51. For example, If pressure is less than 'x'; $P = K1*Q^2 + K2*Q$ If pressure is greater than 'x'; $P = m*Q + b$;

Where P is pressure, Q is flow, and 'b' may be equal to a nominal therapy pressure, and may be tuned by the amount of pretension.

It may be desirable to have 'm' as small as possible, for example by making the orifice large and coefficient of stiffness small.

The expiratory flow resistor of the embodiment of FIGS. 19 and 20 may permit another similar expiratory pressure stenting. This embodiment may permit pressure to be maintained in the expiratory channel 104 through pressure manipulation of a membrane that may be configured as, a membrane balloon 1990. Operation of a flow generator may pressurize the membrane balloon 1990 through a membrane pressurization chamber 1991 or conduit. The chamber 1991 may be coupled with the supply conduit 316 to the flow generator 314 of respiratory treatment apparatus. Pressurization of the membrane balloon 1990 permits the membrane to expand to cover or contact one or more vent apertures of the vent 318 during inspiration as illustrated in FIG. 19. During this inspiratory phase, the inspiratory one-way valve 110-I will be open and flow moves through the inspiratory channel 102 which may optionally include exchanger 106. However, when the patient expires into the patient interface 108, the inspiratory one way valve 110-I will close as illustrated in FIG. 20. When the pressure of the expiratory channel 104 exceeds the pressure in the chamber 1991, the membrane balloon 1990 will deform away from the apertures so as to open the apertures of the vent 318. Since the chamber 1991 is pressurized by the flow generator 314, control of the flow generator, in conjunction with the characteristics of the membrane balloon 1990 and chamber 1991, can permit the setting of an expiratory stenting pressure even though the flow generator does not supply pressure directly to the patient's airways during expiration.

Figure 21:
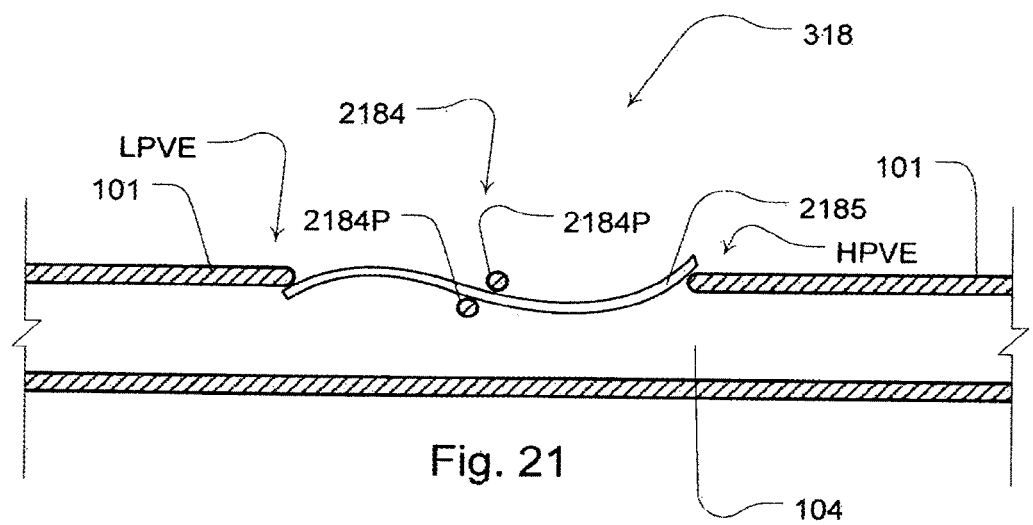
FIG. 21 illustrate a still further flexible expiratory flow resistor with tensioning posts that may be implemented in some conduit embodiments of the present technology.
Figure 22:
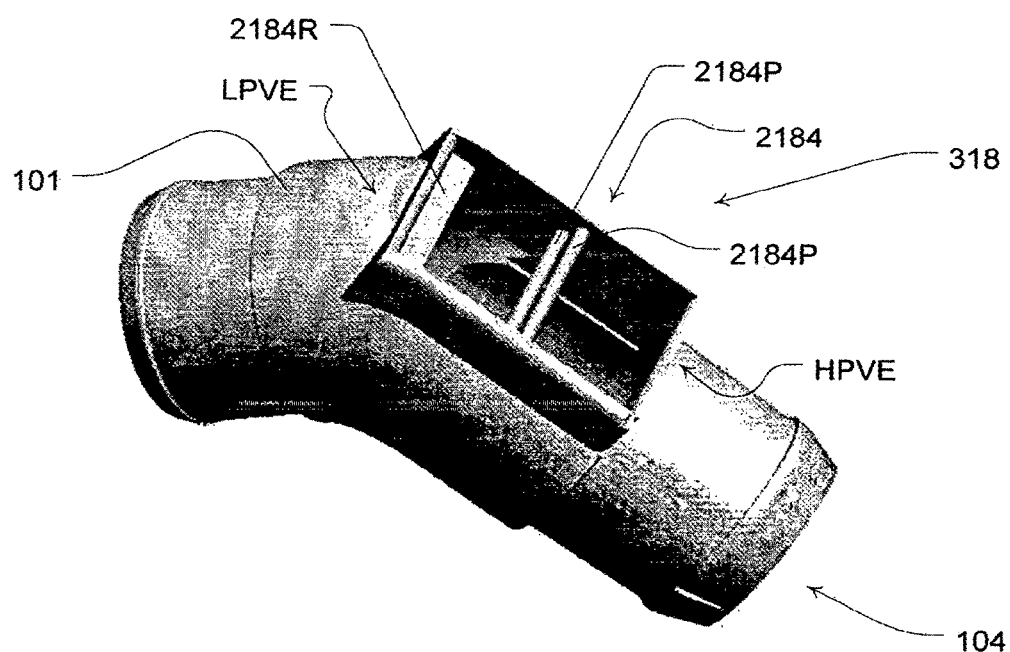
FIG. 22 illustrates an example conduit housing for the expiratory flow resistor illustrated in FIG. 21.

FIGS. 21 and 22 illustrate another membrane structure that may serve as an expiratory resistor similar to the embodiment in FIGS. 17 and 18. The flexible flap 2185 may serve as a barrier between atmospheric air and air in the airpath of the conduit 101 via an aperture of the conduit that allows coupling of therapy pressure and atmospheric pressure. The rigid flap holder 2184 in this embodiment may include one or more tensioning bars 2184P and a holder ridge 2184R that may be integrated with a wall of the conduit 101 to bias the flexible flap. The flexible flap 2185, which may be a resilient membrane under a preloaded tension due to the configuration of the tensioning structures, may flex depending on the pressure within the expiratory channel 104. In this embodiment, the membrane is inserted between the bars. Opposing ends of the membrane may contact an external side of the conduit and an internal side of the conduit. When the flap opens so as to separate from its contact with a rigid wall of the conduit 101 at a high pressure vent end HPVE or a low pressure vent end LPVE, the opening may serve as a vent 318. As explained in more detail herein, the HPVE end permits an air exhaust for a high pressure condition and the LPVE end permits an air intake for a low pressure condition. As shown in FIG. 22, some embodiments of the expiratory resistor conduit may be configured as an elbow, such as an elbow for a patient interface device or an elbow for between an air delivery conduit and a flow generator. However, it may also be implemented in other conduits such as the exchanger conduits discussed throughout this specification.

Such a flow resistor may also serve a purpose of reducing pressure swings in the patient interface (e.g., mask) when used with a pressure treatment device (e.g., CPAP therapy generator). The flexible membrane flap impedes the coupling of the system air path to atmosphere. The impedance changes according to the deflection of the flexible membrane. The deflection of the flexible membrane flap is a function of the pressure differential between the therapy pressure side of the membrane (e.g., in the expiratory channel 104) and the atmospheric side of the membrane. The preloaded tensioning of the flexible membrane flap prevents deflection from the wall of the conduit until the therapy pressure in the conduit rises to overcome the preload so as to open at the high pressure vent end HPVE. In such a case, the membrane at the high pressure vent end HPVE would flex outwardly from the conduit and permit an air exhaust from the conduit. The preloaded tension of the flexible membrane flap may also prevent deflection from the wall (e.g., at holder ridge 2184R) of the conduit until the pressure in the conduit drops enough to overcome the preload so as to open at the low pressure vent end LPVE. In this case, the membrane flap at the low pressure vent end LPVE would extend inwardly into a chamber of the conduit to open the vent 318 and permit air intake into the conduit. These operations can enable 'standard' venting up to a set pressure beyond which the vent opens to allow increased flow to atmosphere in such a way that the therapy pressure remains constant within the conduit for respiratory stenting. The operations can also allow the vent to prevent therapy pressure from becoming negative.

There may be several benefits from such a venting component. It may reduce pressure swings that may be associated with the use of narrow tubes. It may enable the use of narrower tubes. It may reduce inefficient venting (particularly during inhalation). It may reduce total airflow and/or flow generator power when compared to vents that remain constantly open. It may similarly reduce flow through a humidifier so as to thereby increase humidification time limits that are associated with fixed water reservoir size. It may also serve to protect against over pressure and/or asphyxia because it can serve as an anti-asphyxia device. These types of vent may be more suitable to continuous positive airway pressure than bi-level therapy as the operating pressure may be determined by the amount of pre-tension.

The expiratory resistor embodiment of FIGS. 23 and 24, which is similar to the embodiment of FIGS. 19 and 20, may readily permit expiratory stenting pressure to be maintained in an expiratory channel despite an absence of flow against the patient's airways from the flow generator 314 during expiration. A membrane 2390 flexible cover, which may be resilient flexible material, may be positioned over apertures of a vent 318. The cover membrane may serve as a part of separator for an inspiratory channel 102 and an expiratory channel 104. As illustrated in FIG. 23, during inspiration, the membrane 2390 is maintained in a cover position against the apertures of the vent 318 due to the pressure of the inspiratory channel and/or due to the shape memory of a resilient material of the membrane. Inspiratory flow IF, which may be generated by a flow generator 314, may proceed through inspiratory channel 102 and the inspiratory one-way valve 110-I to a patient interface 108 during inspiration. Closure of the inspiratory valve 110-I during expiration, as shown in FIG. 24, permits pressure to build at an expiratory channel 104 side of the membrane. When the pressure from expiration in the expiratory channel 104 side of the membrane overcomes the treatment pressure generated by a flow generator at the inspiratory channel side of the membrane, the flexible membrane 2390 will deflect or expand to permit expiratory flow EF out through the vent 318. Optionally, portions of the flexible membrane may include a material of an exchanger (not shown).

Figure 25A:
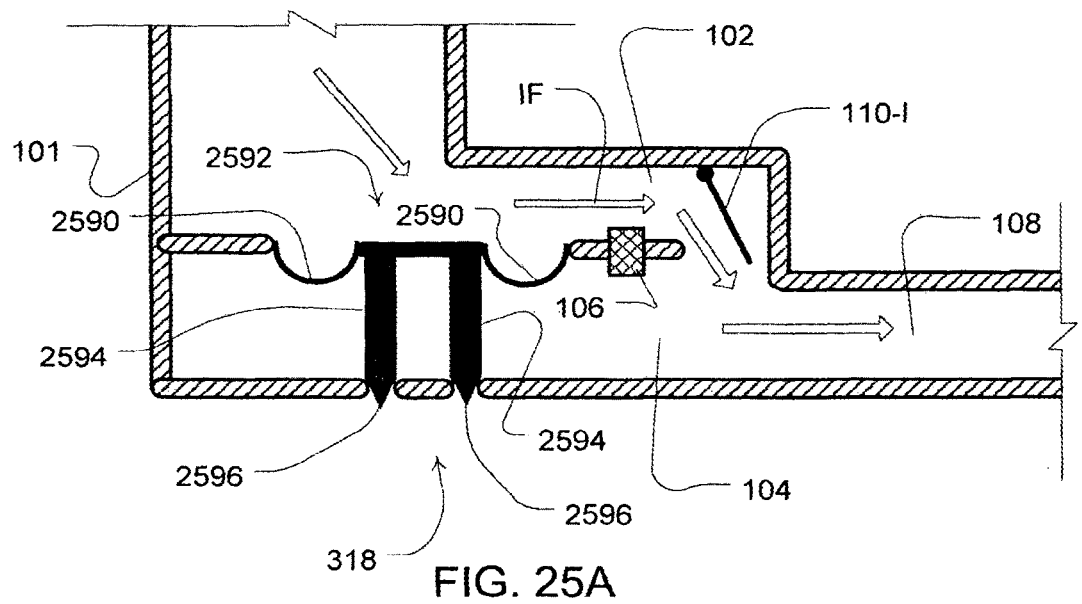
FIGS. 25A and 25B illustrate operation of another flexible expiratory flow resistor that may be implemented in some conduit embodiments of the present technology.
Figure 25B:
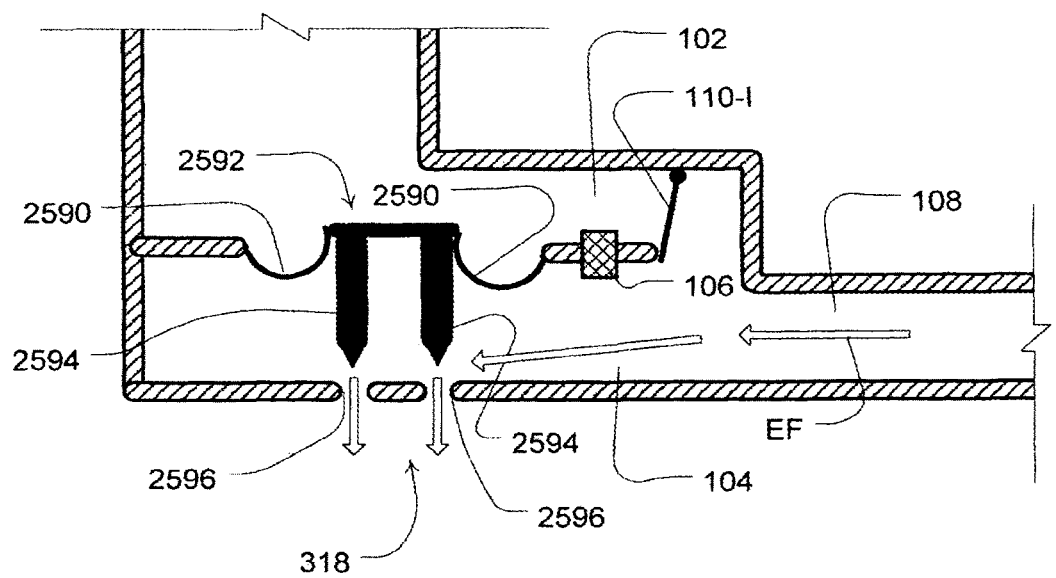

The embodiment of FIGS. 25A and 25B is similar to that of FIGS. 23 and 24. However, in the embodiment of FIGS. 25A and 25B, the flexible membrane 2590 includes an expiratory flow stopper 2592. The stopper 2592 may include one or more plugs 2594 that may be configured for closing vent apertures 2596 of vent 318. For example, plugs may be configured for selectable insertion within the vent apertures 2596. Optionally, such plugs may be tapered. As illustrated in FIG. 25A, the resiliency of the flexible membrane and/or the pressure from a flow generator at an inspiratory channel 102 side of the membrane or stopper may maintain the flow stopper 2592 in a closed or partially closed position during inspiration. During patient expiration, as illustrated in FIG. 25B, an increase in pressure in the expiratory channel 104 side of the membrane 2590 will shift or flex the membrane and the flow stopper when the increase in pressure overcomes the pressure (e.g., flow generated treatment pressure) at the inspiratory channel 102 side of the membrane 2590. This shift of the membrane and stopper will withdraw the plugs 2594 from within the vent apertures 2596 to permit venting of expiratory air. Since the expired flow must overcome any membrane resiliency and/or the treatment pressure at the inspiratory channel 102 side of the membrane, a stenting pressure may be maintained in the expiratory channel 104 as well as in the patient interface and patient respiratory system.

Additional Example Embodiments

Figure 52:
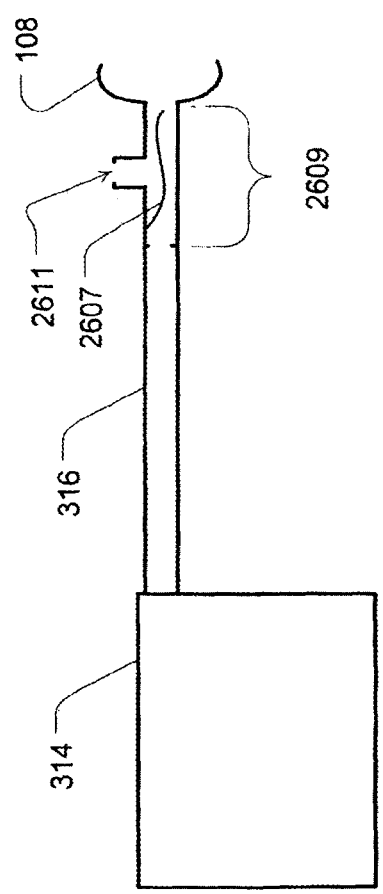
FIG. 52 is an example system configuration diagram showing a conduit with a flexible channel divider coupled with a flow generator and patient interface.

Further example embodiments for conduits of the present technology that can be implemented with an exchanger are illustrated in the cross-sectional views of FIGS. 26, 27, 28, 29, 30, 31, 32 and 33. In these examples, a flexible channel divider 2607, such as a membrane, may serve to regulate inspiratory flow in the conduit 2609 to dynamically create the inspiratory and expiratory flow channels and may provide dynamic expiratory venting. In some cases, the conduit 2609 may be coupled proximate to a patient interface (e.g., patient interface 108) at the opposite end of a supply conduit 316 from a flow generator 314 as illustrated in FIG. 52. Implementation of such a divider may permit a reduction of total flow through a mask, such as when compared to a patient interface using a continuous vent, and may thereby increase efficiency of humidifiers, oxygen sources and flow generators. The force required to breath against the divider may also permit an elevated expiratory stenting pressure that may be adjusted by choosing a suitable vent size and divider flexibility. This can also reduce the work of a flow generator during expiration. Similarly, the divider may reduce pressure swings in the conduit leading to a patient mask such that it may reduce the burden on a flow generator to compensate for the pressure swings. Optionally, the flexible divider may also be implemented with components or materials previously discussed such that the moveable divider may also serve as an exchanger. Generally, the mechanical properties of the flexible divider can be tuned by varying thickness or other dimensions and its material properties, such by changing its stiffness, density and damping characteristics.

Figure 26:
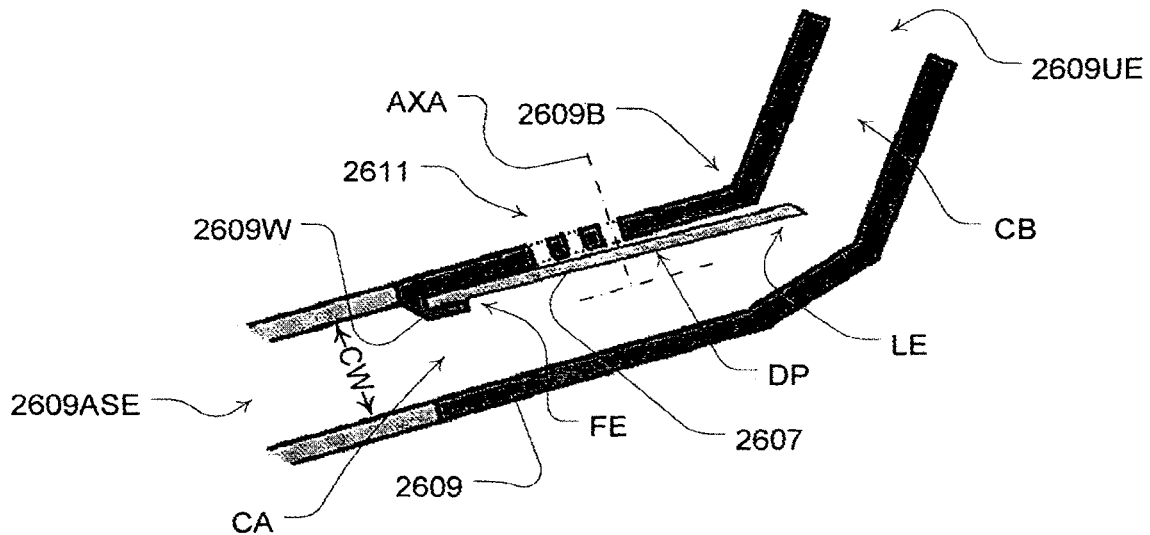
FIG. 26 is a cross-sectional view of a conduit having a flexible channel divider that may be configured as an exchanger in some embodiments of the present technology illustrated in a position when there is no flow generator pressure such that it may serve as an anti-asphyxia device.

For example, as illustrated in FIG. 26, the channel divider 2607 may be implemented within a conduit 2609. Such a flexible divider may have a fixed end FE and a deformable portion DP. The fixed end may be coupled with the conduit wall 2609W. The divider 2607 is also substantially proximate to a venting portion 2611, which may be formed by a plurality of apertures for expiratory venting, so as to permit the divider to serve as a cover of the venting portion. The pneumatic impedance of the venting apertures may be controlled in the design by their geometry, such as their length and cross-sectional area, as such the impedance of the apertures may provide additional pressure to the divider during expiration. This can assist with the activation of the divider at the beginning of expiration and prevent the divider from blocking the apertures during periods of small expiratory flow, such as the end of expiration.

Optionally, the conduit may include a conduit bend 2609B such that the wall of the conduit and the channel of the conduit deviate from a straight direction. In such an embodiment, the divider may extend along the wall from one portion of the conduit with a first channel CA that has a first angle into the bend portion of the conduit that has a second channel CB at a second angle. The extension of the divider across the bend from the first channel to the second channel creates a lip end LE on the flexible portion DP of the divider where the divider deviates from the conduit wall. As described in more detail herein with reference to FIGS. 28, 29 and 30 concerning the operation of the assembly, the lip end LE may assist in the dynamic activation of the channel divider. Generally, the lip end LE of the divider is more proximate to the patient or user end 2609UE of the conduit, such as where a mask may be coupled, and the fixed end FE of the divider is more proximate to the air or gas supply end 2609ASE of the conduit, such as where a flow generator output may be coupled.

Figure 30:
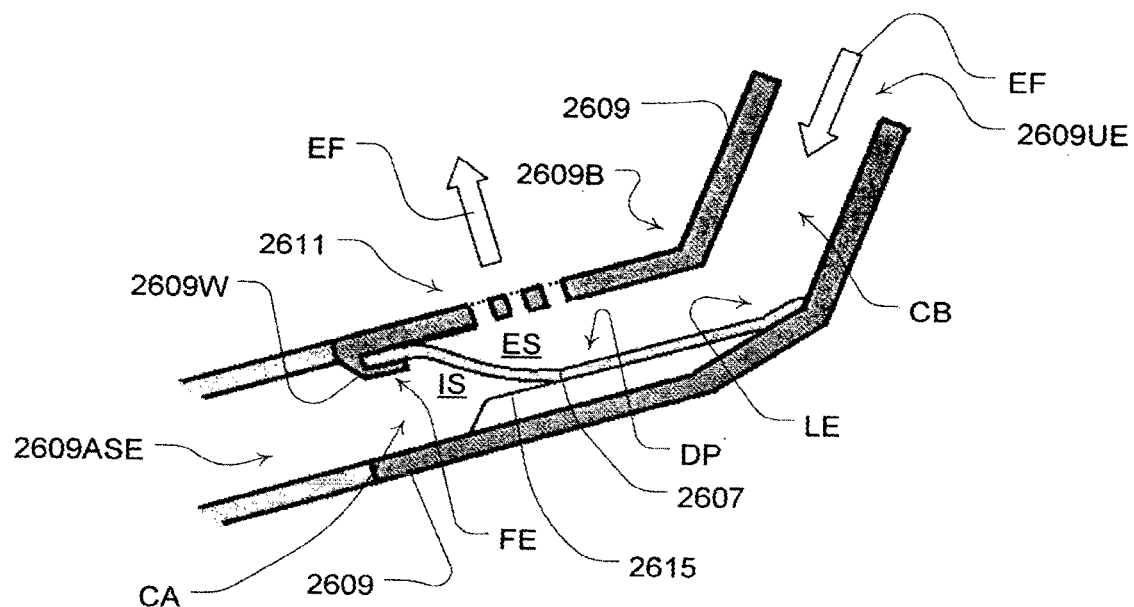

With respect to the dynamic creation of the inspiratory and expiratory channels, the divider may create an inspiratory channel between a first side of the conduit and a first side of the divider and an expiratory channel between the opposing side of the conduit and the opposing side of the divider when the divider traverses between the opposing sides of the conduit during use. The divider may do so by traversing across the conduit from one side to the opposing side. Typically, such a transition of the divider to the fully open expiratory position as shown in the example of FIG. 30 from the fully open inspiratory position shown in FIG. 28 (and the opposite transition) is very quick. Generally, the divider will be in these fully open positions during each respective phase of respiration. This reduces the velocity and turbulence of the air flow and results in lower noise, which can be particularly important for use during sleep.

The flexible divider may be configured such that during inspiration the forces acting on the divider force it into a position that obstructs, or impedes venting to atmosphere. The forces include the static and dynamic components of pressure acting on the divider surfaces and the force due to gravitational acceleration acting on the mass of the divider. The divider can be light to minimize the later forces and other dynamic acceleration effects. The flexible divider may also be configured such that during expiration the forces acting on it force it into a position that obstructs or impedes flow to the flow generator (preventing or reducing the possibility of rebreathing).

Since the divider may be flexible, the response of the divider may be controlled by setting different pressures with the flow generator. Moreover, the level of flow may be controlled or dictated by the user. For example, if the patient is not breathing on the system, the flow by the divider (e.g., from the flow generator) may be zero. The higher the patient's expiration pressure, the more open the expiratory channel becomes, which provides larger flow, less turbulence and less noise. Accordingly, the pressure may be controlled by the flow generator but the patient may dictate the flow.

Generally, the position of the divider may be determined by the equilibrium of forces acting on it. One of the main contributors to this equilibrium position is the therapy pressure times the surface area of the divider which is exposed to the therapy pressure. Another main contributor to the equilibrium is the pressure coming from the flow generator times the surface area of the divider exposed to that pressure. If we neglect all other forces, by Newtons Second Law, the mass times the acceleration of the divider will equal the difference between the two main forces. As such, the divider will accelerate toward the direction of the side of the lower pressure. As this happens, the expiratory impedance will change and this will result in the therapy pressure changing, such that a new equilibrium is reached. When the forces are equal the divider will be stationary. When the respiratory flow changes the equilibrium position of the divider will change and alter the expiratory resistance to equalise pressures on each side of the divider.

By reducing or ceasing venting flow during inspiration, which the divider is capable of achieving by intermittent closing of venting apertures as discussed herein, the total flow through the supply conduit may be reduced. Reducing vent flow during inspiration reduces the amount of flow that the flow generator needs to produce to maintain therapy pressure. Eliminating vent flow can reduce the amount of flow the flow generator needs to produce by more than 50%. This means for a constant speed flow generator, the pressure drop can be (significantly) less. The pneumatic efficiency of the flow generator system will be increased. Moreover, a pressure controlled flow generator will need to compensate less for the supply conduit (e.g., tube) loss. Reducing flow generator flow also makes the full system more energy efficient and quieter. This may also permit the conduit to be employed in systems that deliver support using narrow, high impedance supply conduits.

Moreover, in the absence of inspiratory venting, the inspiratory pressure drop or the need to compensate for an inspiratory drop to improve pressure swings may be reduced.

Reduced venting also may reduce the drying effect on the patient's airways since flow is only provided when the patient breathes. It may also permit more natural breathing at higher pressures.

Figure 59:
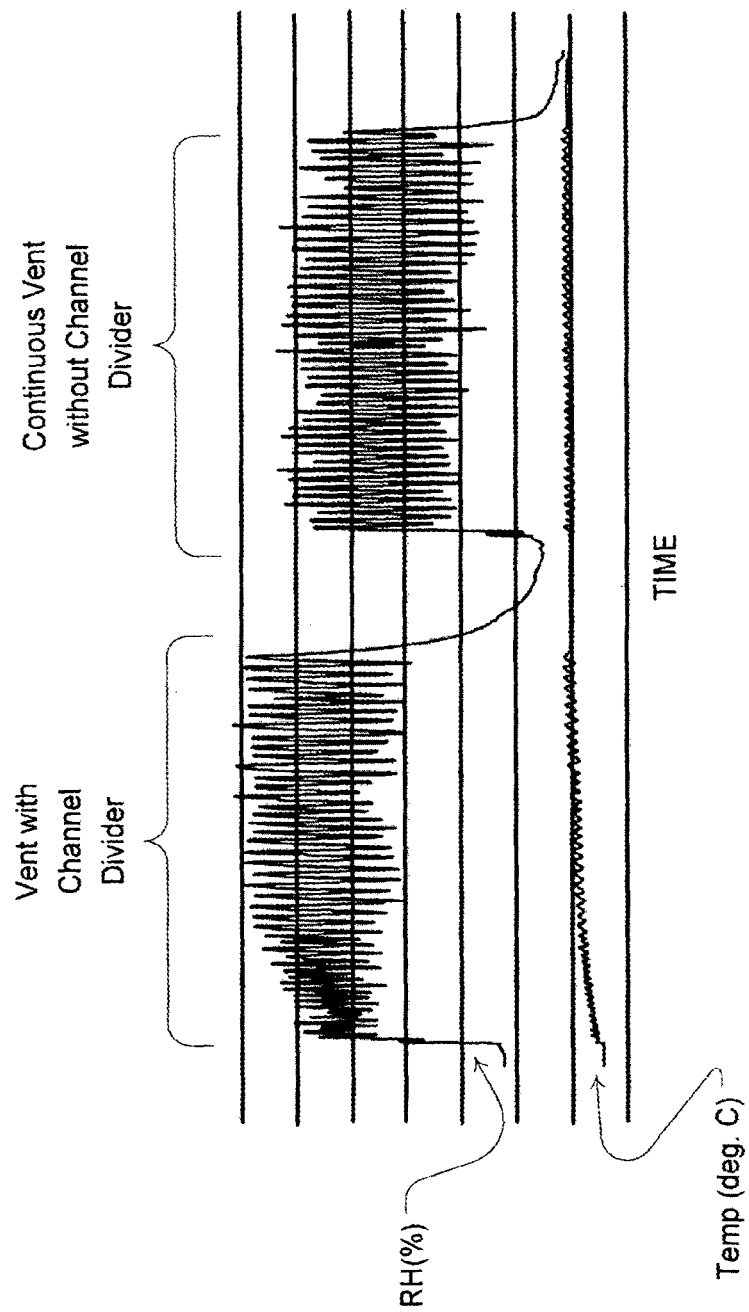
FIG. 59 is a signal graph with patient interface humidity and temperature data illustrating a comparison of a flexible channel divider such as the divider of the conduit of the example of FIG. 26 with a traditional continuous-type vented mask having no such divider.

The action of the divider and reduced total flow may also have the effect of increasing humidity in the patient interface. As illustrated in FIG. 59 showing humidity and temperature data, venting with the divider over time may promote a higher degree of humidity when compared to a traditional continuous vent type mask. On average, the divider could provide a level of humidity approximately 10% higher than the humidity provided using a standard continuous vented mask. As a result, it can also improve the effectiveness of any exchanger or HME material such as if implemented in the configuration of FIG. 47. Generally, the natural humidity in the system can be improved with the use of the divider.

The reduction in flow and the resulting retention of moisture can mean longer humidifier operation. This can reduce the need for refilling a humidifier with water, or permit a smaller capacity humidifier design when the divider is implemented with an active humidifier. Similarly, oxygen delivery can be more efficient. Reduced flow generally results in less turbulent noise both at the vent, and in the flow generator system. Reduction in flow related pressure losses can mean lower motor speeds, and result in less machine noise and longer machine life. A more efficient flow generator system can result in less power being required to operate the system. For a portable device, this could permit use of smaller battery or a battery with less capacity, or can permit longer battery operation.

The reduced flows with the conduit can permit a more natural feeling therapy. Continuous venting is often perceived by the patient in the form of noise and vibration. The continuous venting flow also has a drying effect on the airway, requiring use of a humidifier for some. The flexible divider vent can permit users to experience a more natural feeling therapy even when the pressure is increased, since the user determines the amount of flow in the system. This can result in reduced drying of the airways and reduce or remove the need for a humidifier system.

Figure 27:
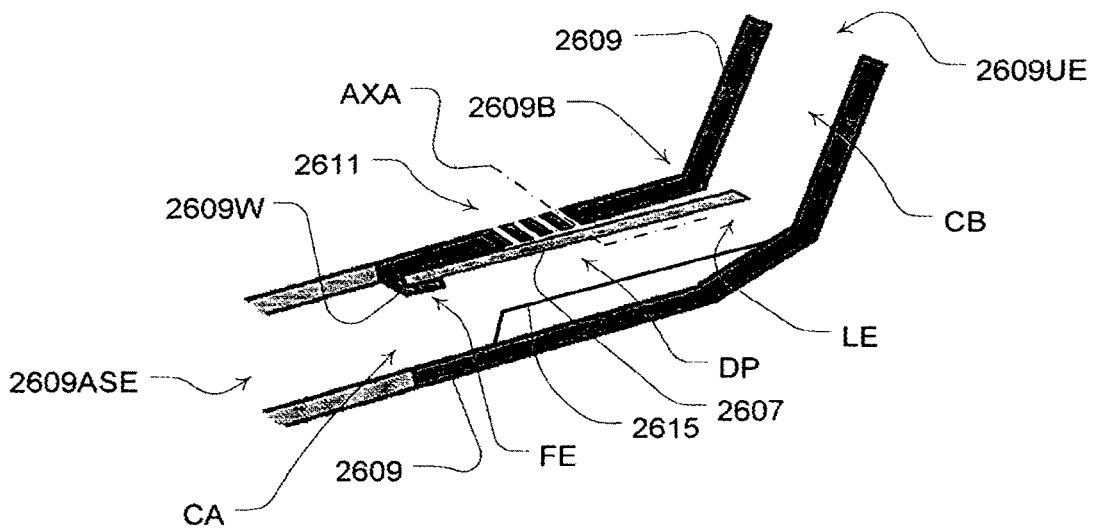
FIG. 27 is a cross-sectional view of a further example embodiment of the conduit of FIG. 26 including an oblique venting portions and ribbed divider support.

Accordingly, returning to FIG. 26, the venting portion 2611 may include a plurality of apertures. These apertures may be optionally bored through a wall of the conduit or be applied as a grate component to the conduit. The apertures may run perpendicular to the inner conduit surface as illustrated in FIG. 26. However, in some embodiments that may improve flow through the venting portion, the apertures may be at an oblique angle relative to the surface of the conduit. For example, as illustrated in FIG. 27, the apertures may deviate from perpendicular so as to angle the channel of each aperture toward the lip end of the divider. In some embodiments a diffuser may be applied over the venting portion.

Figure 32:
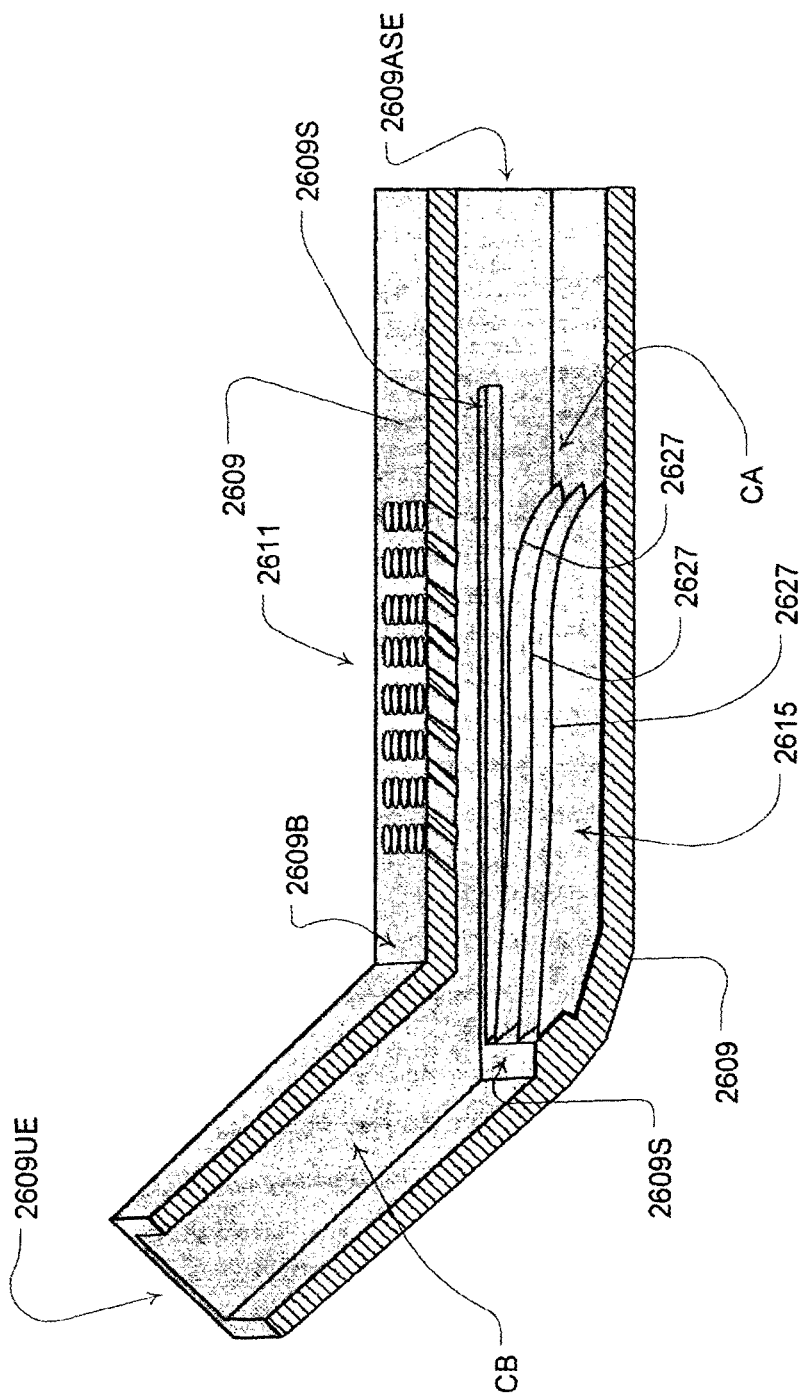
FIG. 32 is an illustration of the internal structure of an example conduit suitable for implementation with a flexible divider assembly of FIG. 27.
Figure 46:
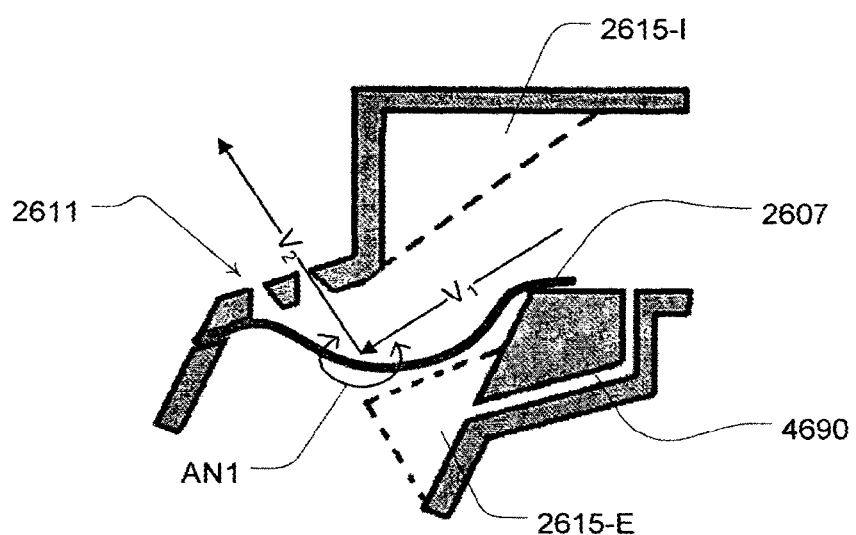
FIG. 46 is a cross sectional illustration of a conduit similar to the conduit of FIG. 27 that includes a bypass channel.

Example aperture angles may be considered with reference to imaginary axis lines AXA shown in FIGS. 26, 27 and 32. For example, as illustrated in FIG. 26, apertures of the venting portion 2611 may be formed generally perpendicular to the flow path or inner surface of the channel of the conduit 2609. In some cases, as illustrated in FIG. 27, the channels of the inner surface of the apertures of the venting portion 2611 may be formed at an obtuse angle with respect to the inner surface of the channel of the conduit and direction of expiratory patient flow. In such a case, the direction of expiratory airflow from the user end 2609UE through the conduit will not deviate too substantially between the direction of the channel of the conduit and the direction of the channel of the aperture. In such a case, patient expiratory turbulence through the venting portion may be minimized. However, in some cases, expiratory patient airflow turbulence may be increased with the implementation of apertures with channels that deviate at an acute angle from the inner surface or channel of the conduit with respect to the direction of expiratory flow as illustrated in FIG. 32. The expiratory airflow turbulence created with such acute angled apertures may help to affect a more responsive action (e.g., quicker) by the divider to expiratory flow at lower flows. As such, the divider may stay in an open position with respect to the venting portion longer as the rate of expiratory flow recedes (e.g., at or nearer to the end of expiration) or open faster with initial expiration. Thus, a smaller expiratory flow force may continue to deflect the divider. In addition, the acceleration required to turn the flow direction to the new angle requires a reaction force of the divider. This reaction force tends to open the path to the aperture, and thus reduces the impedance of the path, hence lowering the therapy pressure, and allowing the divider to remain in the open position longer. The amount of reaction force may be tuned by tuning the angle of deviation of the flow path. This may be understood by calculating the reaction force according to the equation $$F = dm/dt(v_2 - v_1)$$

Where F is the force vector (having magnitude and direction), dm/dt is the mass flow rate of the gas, $v_1$ is the flow velocity vector (having magnitude and direction) of the fluid approaching the divider as illustrated in FIG. 46. And $v_2$ is the flow velocity vector (having magnitude and direction) of the fluid leaving the divider as illustrated in FIG. 46. It can be seen from the equation that as the angle between $v_1$ and $v_2$ increases the reaction force also increases. Therefore, in some embodiments it may be desirable to divert the expiratory gas by a large angle (illustrated as angle AN1 in FIG. 46) in order to exert a suitable force on the divider.

Optionally, the conduit may also include a divider support 2615, such as one or more ridges, fins or ribs that may project or extend into the first channel CA, along the conduit wall that is on a side opposite to the side of the conduit where the membrane is fixed. The fins, ribs or ridges may be generally parallel and extend longitudinally along the flow path of the conduit. Such a membrane support may help to prevent the membrane from over flexing as discussed in more detail herein. An example of an internal structure of the conduit assembly including several rib or fin-type membrane supports 2627 is illustrated in FIG. 32. This embodiment also employs a divider shelf 2609S that may be formed along the conduit wall. The divider shelf provides a seat against which a peripheral edge of the divider may seal during expiration as discussed herein in reference to FIG. 30.

The length of the divider 2607 from its fixed end FE to the lip end LE may also be particularly chosen to prevent over flexing that in some instances might cause jamming of the divider in the channel. For example, in a typical embodiment the length will be greater than the channel or conduit width (shown as CW in FIG. 26) but may be substantially longer. For example, the range of such a length may be on the order of 1.25 to 8 times the channel or conduit width CW of the particular channel across which the divider will flex. In some cases, it may even be larger.

In some cases, the divider may be configured with a normal position such that it will, in the absence of flow or pressure forces associated with flow generator operation, resiliently remain slightly deviated away from the venting portion 2611 as shown in FIG. 26. This marginal deviation may permit flow through the venting portion such that it may serve as an anti-asphyxia device. Thus, in the absence of any pressure generated by the flow generator (e.g., a flow generator failure or turned off flow generator), the channel divider will return to this normal "deviated" position to permit a patient to breathe through the venting portion 2611 and the flow generator during inspiration. Such a deviation may, for example, be achieved by the resiliency and form of the material of the divider itself (e.g., a curved divider profile) and/or by the divider positioning with respect to the conduit structure such as at its fixed end FE. Nevertheless, with or without such a normalized deviation feature, and in the failure of operation of the flow generator, functional movement of the flexible divider may still occur in response to patient respiration. For example, patient expiratory flow can still force the divider to open to atmosphere allowing expired air to vent to atmosphere so as to prevent rebreathing, even if the flow generator is powered off.

Figure 28:
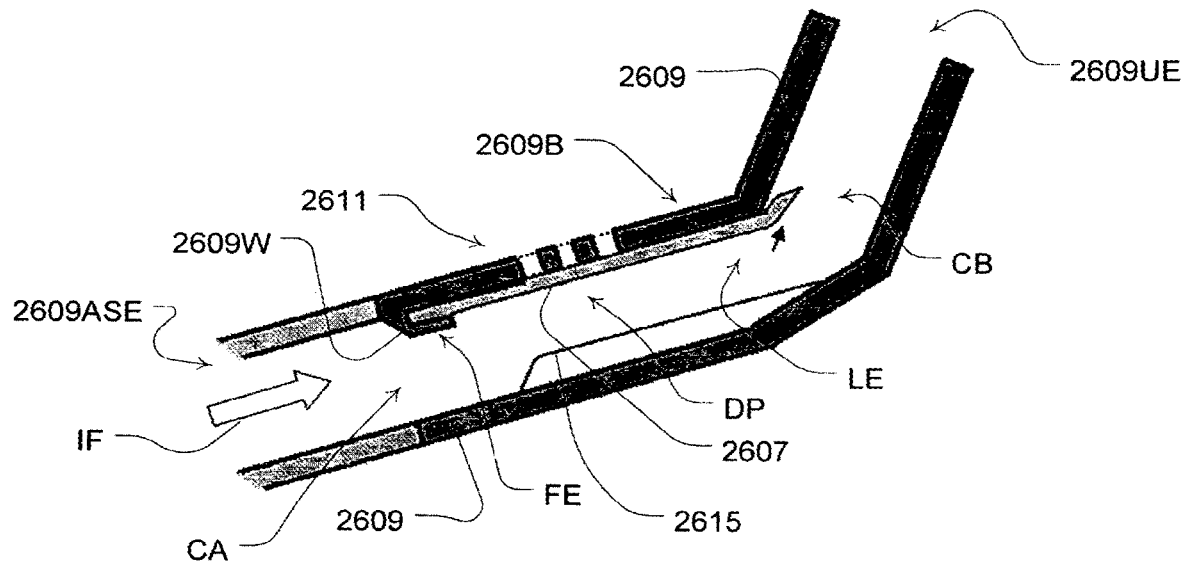
FIGS. 28, 29 and 30 illustrate operation of the embodiment of FIG. 27 during inspiration, start of expiration and expiration respectively.
Figure 29:
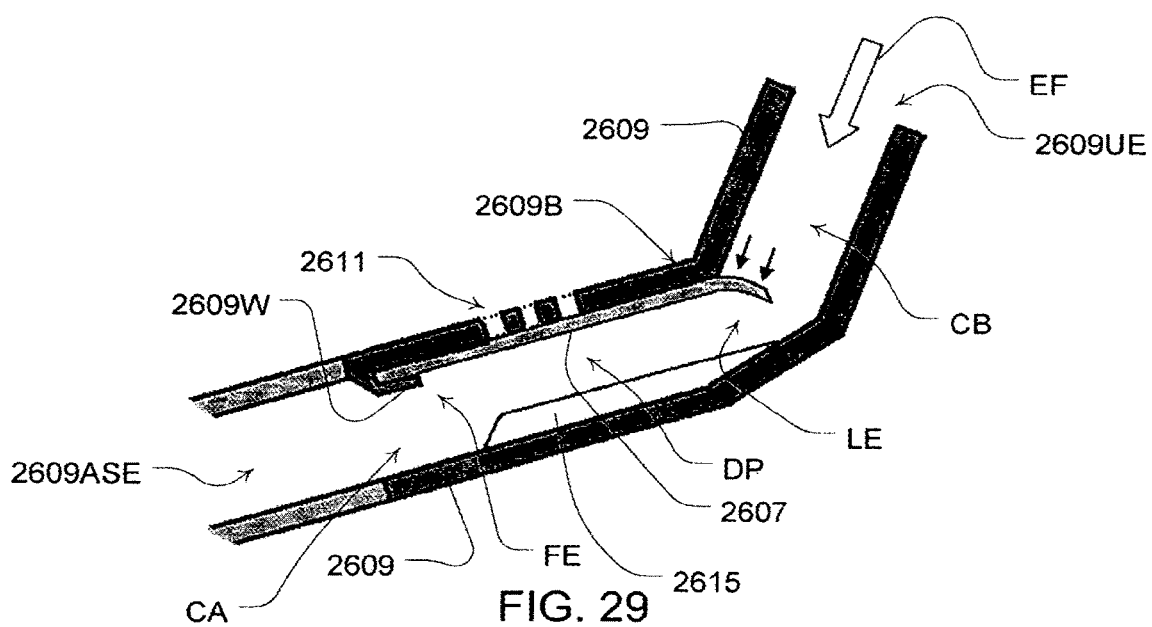

Operation of the flexible channel divider 2607 may be further considered in reference to FIGS. 28, 29 and 30 which illustrate inspiration, start of expiration and expiration respectively. As shown in FIG. 28, an inspiratory flow IF across the divider and the lip end LE of the divider applies a pressure force (shown as black arrow) against the divider to keep the divider in a position covering the venting portion 2611 and, if present, overcoming the previously mentioned deviation. Thus, the inspiratory flow IF would move through the first channel CA and the second channel CB of the conduit toward the user UE or mask end of the conduit. As illustrated in FIG. 29, at the beginning of expiration, an initial expiratory flow EF applies a pressure force (shown as black arrows) at the lip end LE of the divider so as to begin to raise the divider away from the wall of the conduit 2609. As illustrated in FIG. 30, as the expiration flow EF continues, having shifted the lip end LE, the expiratory flow plies a force to the remainder of the deformable portion of the divider that moves the divider away from the venting portion side of the conduit toward a position on the opposite support side of the conduit. This movement allows the expiratory flow EF to vent through the apertures of the venting portion 2611. It also blocks flow through the conduit from the air or gas supply end 2609ASE to the user end 2609UE when the divider seals with a portion of the conduit such as the divider shelf 2609S. The raised ridges of the divider support 2615 help to prevent the flexible divider from curling or overextending within the conduit during expiration, which could undesirably result in jamming the flexible divider within the conduit so as to prevent its return to cover the venting portion during inspiration.

The movement of the divider during expiration also dynamically separates the channel of the conduit so that the divider has an inspiratory side IS and an expiratory side ES. Thus, when the flexible divider is formed of a temperature conducting and/or humidity conducting material, the divider may serve as an exchanger as previously described. Moreover, the assembly may serve as an anti-asphyxia valve when connected to a respiratory treatment apparatus. In the event of a blocked conduit on the air or gas supply end 2609ASE, a patient's inspiration will deflect the divider from the venting portion 2611 to allow air intake through the venting portion.

Figure 31:
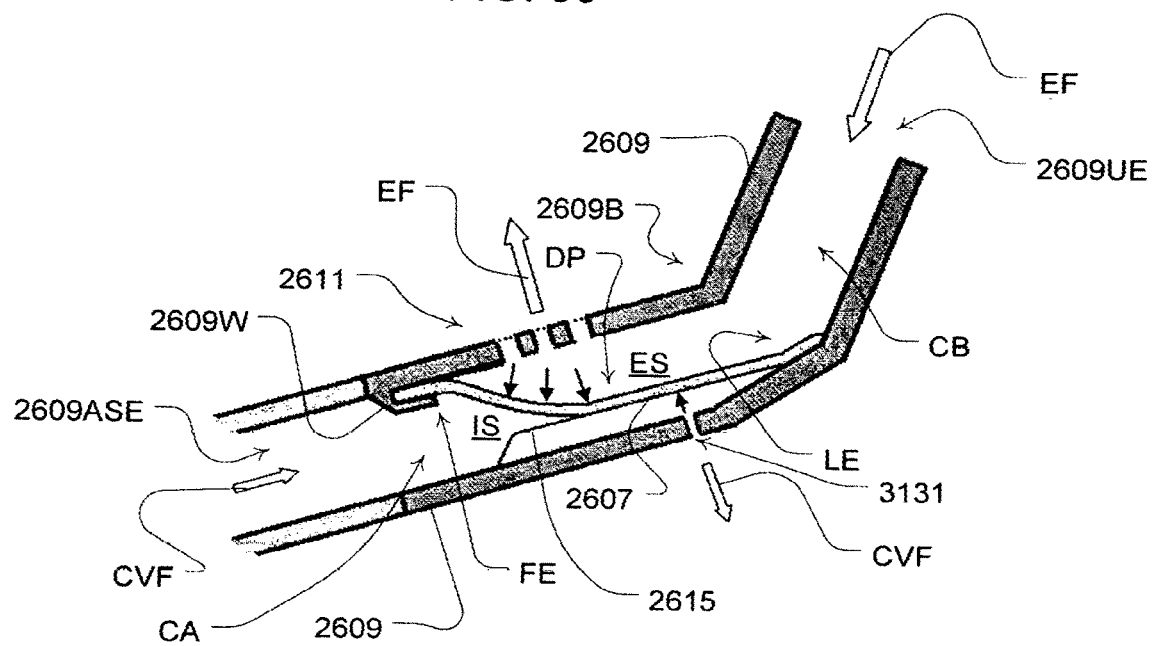
FIG. 31 is a cross sectional view of a continuous venting embodiment of the assembly of FIG. 27.

A further alternative embodiment of such an assembly is illustrated in FIG. 31. The conduit and divider embodiment of FIG. 31 includes a structure and operates similar to the embodiment of FIGS. 28, 29 and 30. However, this embodiment also includes a continuous vent 3131. The continuous vent will permit a continuous vent flow CVF from a supply source, such as a flow generator, during expiration as illustrated in FIG. 31, as well as during inspiration (not shown). In this regard, movement of the divider does not block the continuous vent 3131. During expiration, when the divider is moved to its position adjacent to the ribs or ridges of the divider support 2615. A continuous vent flow CVF from the air or gas supply end 2609ASE will flow around or between the ribs of the divider support to pass through one or more apertures of the continuous vent 3131.

Figure 33:
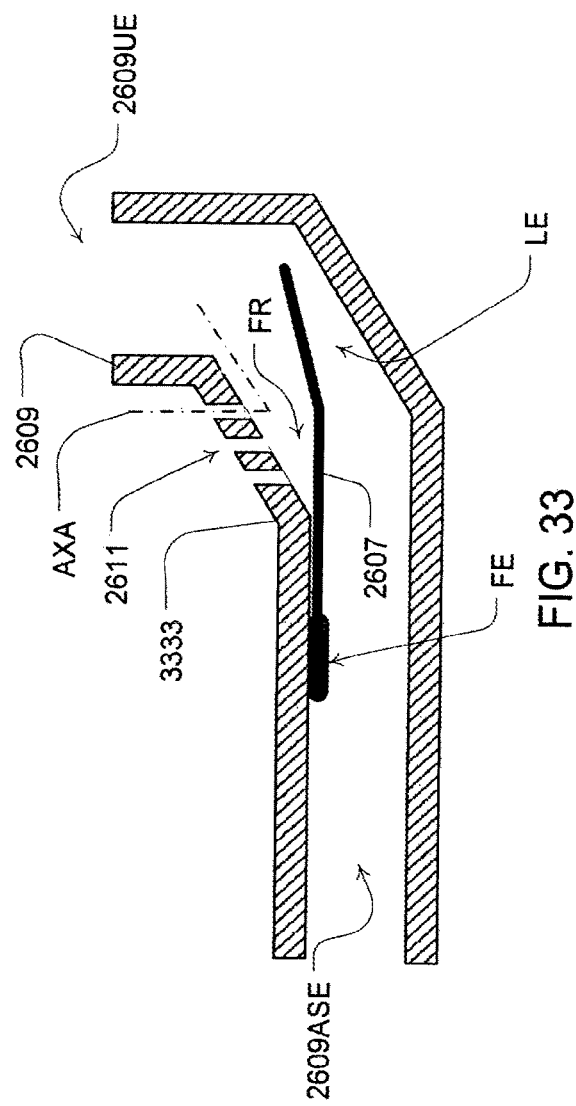
FIG. 33 is an illustration of a cross-sectional view of the internal structure of an example conduit having a channel bend and extended flexible divider.

In the example of FIG. 33, the conduit 2609 employs a bend 3333 in the channel, such as one formed by the wall of the conduit. The flexible region FR of the channel divider 2607 may be positioned proximate to the bend 3333 such that it may extend over the bend. The flexible region FR may be preloaded or otherwise chosen to have a particular spring constant. The spring constant may serve to bias the channel divider 2607 to a particular respiratory event. For example, the spring constant may be chosen to bias the divider to an expiratory position such that the venting portion 2611 remains normally open, such as in the absence or insufficient flow or pressurized air directed from the air or gas supply end 2609ASE. In such a case, the pressure and/or flow required to open the venting portion (e.g., moving the divider away from the venting portion) such as the pressure or flow of patient expiration may be reduced when there is a flow from the gas supply end 2609ASE of the conduit. The bend, and the positioning of the divider extending across the bend, may also permit operation of the divider so as to take advantage of directional flow (e.g., expiratory flow and the turbulence created thereby in relation to the structure of the bend) as well as pressure. Such a divider may have a faster operation, with respect to valves operating just in response to pressure or just in response to flow, and may permit it to remain open longer with less flow and low pressure. Moreover, by extending the divider out from the bend (e.g., the lip end LE), exposing a larger portion of the divider to the flow of the channel of the conduit such as when compared to the similar but smaller extension (e.g., the lip end LE) of the divider in FIG. 26, the larger extension can provide a divider with more responsiveness to channel flow (e.g., expiratory flow).

The example vents of FIGS. 26 to 32, as well as others of the application, may be suitable for implementation with ventilators, such as a ventilator that provides volume controlled ventilation (e.g., pressure support to meet a target measure of ventilation like a minute ventilation or tidal volume etc.). The vent size may be fixed and can be implemented to provide a positive end expiratory pressure (PEEP) component of therapy. For example, as the flow generator generates pressure against the side of the divider proximate to the gas supply end 2609ASE of the conduit, the reaction of the divider thereto and consequent pressure force required to overcome the divider to vent on the user side of the divider, can serve to provide the PEEP therapy component.

Figure 34:
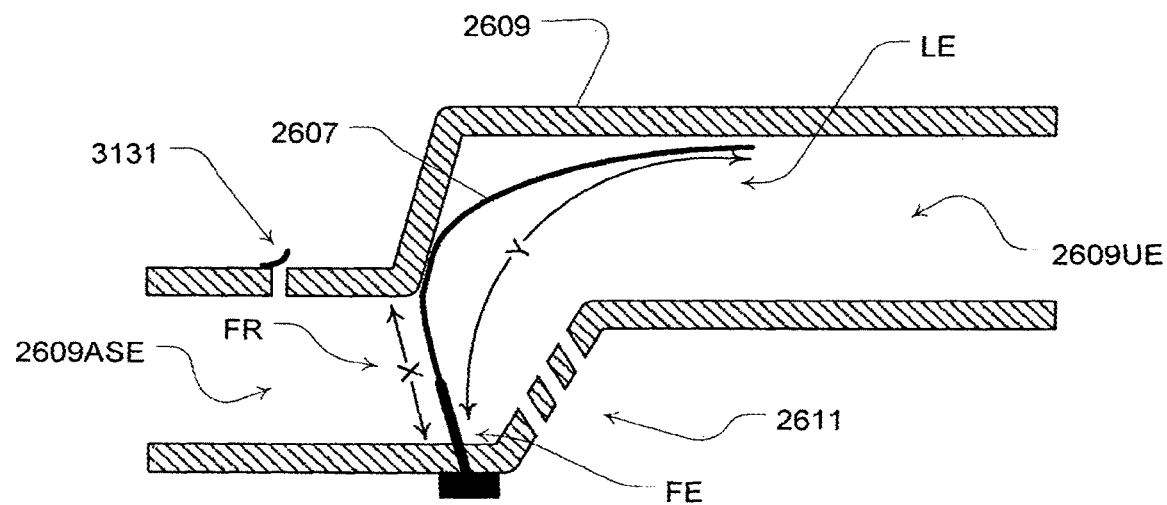
FIG. 34 is a cross-sectional illustration of the internal structure of a conduit in and expiratory position having a flexible divider with opposed surface areas of different size.
Figure 35:
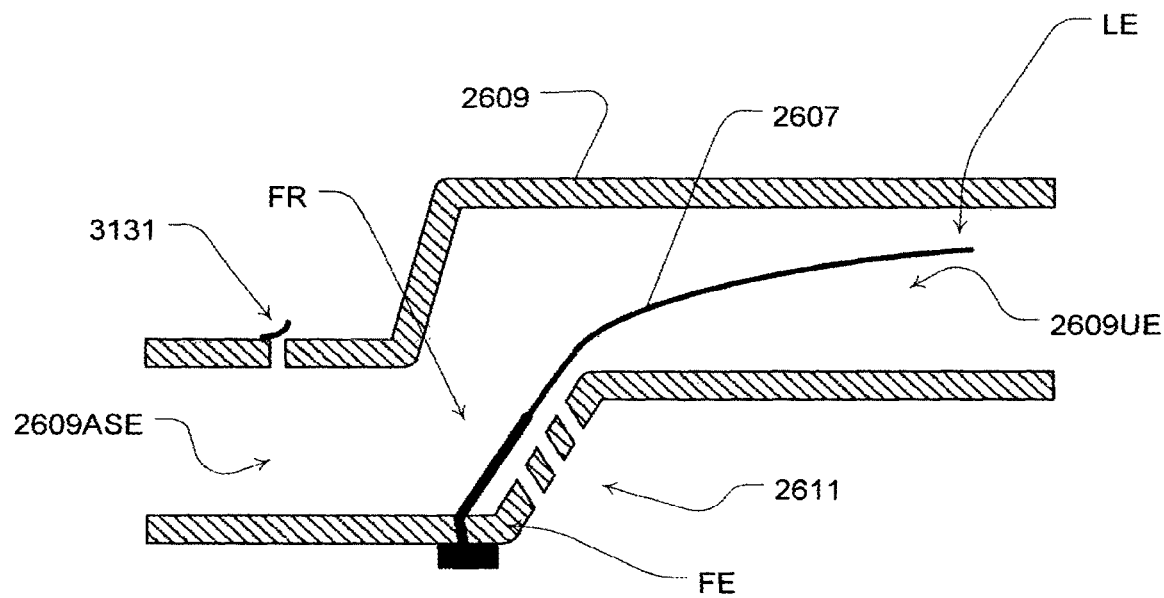
FIG. 35 illustrates the structure of the conduit example of FIG. 34 in an inspiratory position.

In some cases, the divider and channel may be configured to provide different flow activation contact areas on the two sides of the divider (e.g., the side exposed to direct flow from the gas supply end 2609ASE of the conduit when compared to side exposed to direct flow from the user end 2609UE of the conduit. An example of such a feature is illustrated in the conduit of FIGS. 34 and 25. In this example, the area of the side exposed to or activated by patient exhalation flow (shown at arrow Y) has a greater area that the area exposed to or activated by flow of the gas supply end (shown at arrow X) (i.e., X<Y). As a consequence, and based on the chosen areas, a flow generator may provide higher flows/pressures for patient treatment on the gas supply side while still permitting a response by the divider to the smaller pressure/flows of patient expiration at the user side so as to ensure opening of the divider to vent flow through the venting portion 2611 during expiration. Optionally, the vent of FIG. 34 may also employ a continuous vent 3131, which may optionally be pre-set to have different vent flows.

Figure 36:
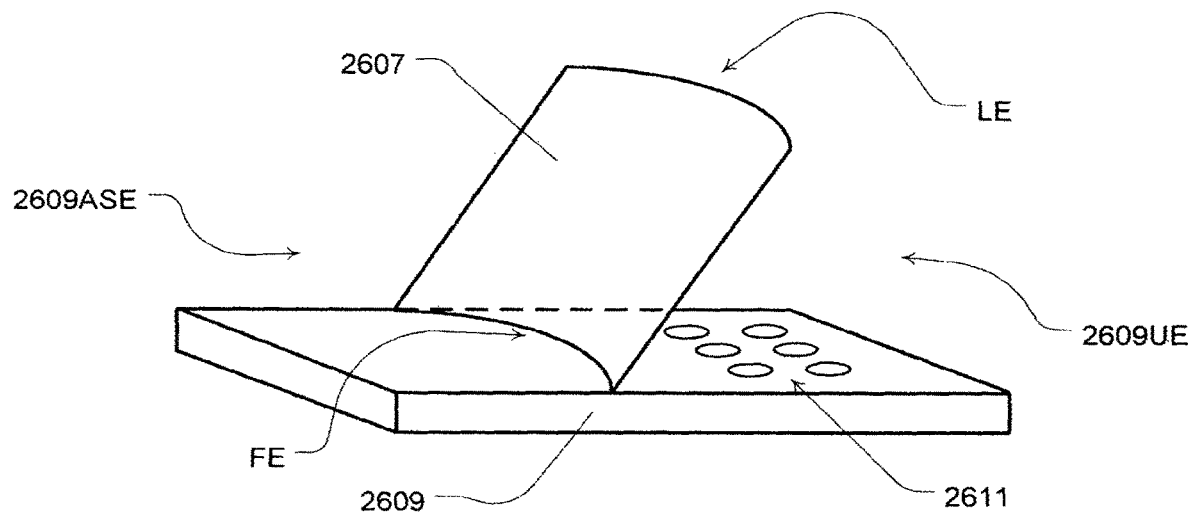
FIG. 36 is an illustration of a divider having a surface with a contoured structure.
Figure 37:
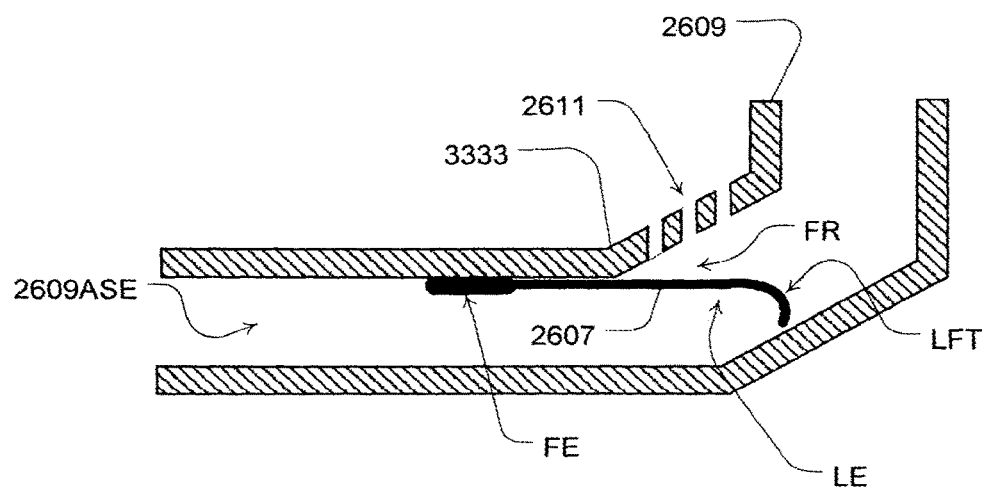
FIG. 37 is an illustration of a divider with a normal bend.

In some examples, the surface of the divider, although optionally at least in part flexible, may have a planar shape. However, in some examples the divider may conform to non-planar surface shapes and may optionally be rigid or deform therefrom under chosen flow and pressure characteristics. Such shapes may promote different flexibility and/or movement characteristics of the divider as desired. For example, as illustrated in FIG. 36, the surface of the gas supply end 2609ASE of the divider 2607 may have a concave surface. Optionally, a convex surface may be formed at its opposite side, facing the user end 2609UE of the conduit 2609. In some examples, such surfaces may be reversed. For example, the surface of the gas supply end 2609ASE of the divider 2607 may have a convex surface and a concave surface may be formed at its opposite side, facing the user end 2609UE of the conduit 2609. In some cases, the divider may be formed with a rigid or flexible bend, curve or lift LFT at its lip end extending into a channel of the conduit, such as the example illustrated in FIG. 37. Such a divider will normally maintain the shape of the lift. Such a lift may promote or ensure exposure of the divider to certain flows of the conduit, such as an expiratory flow from the user end 2609UE.

Figure 38:
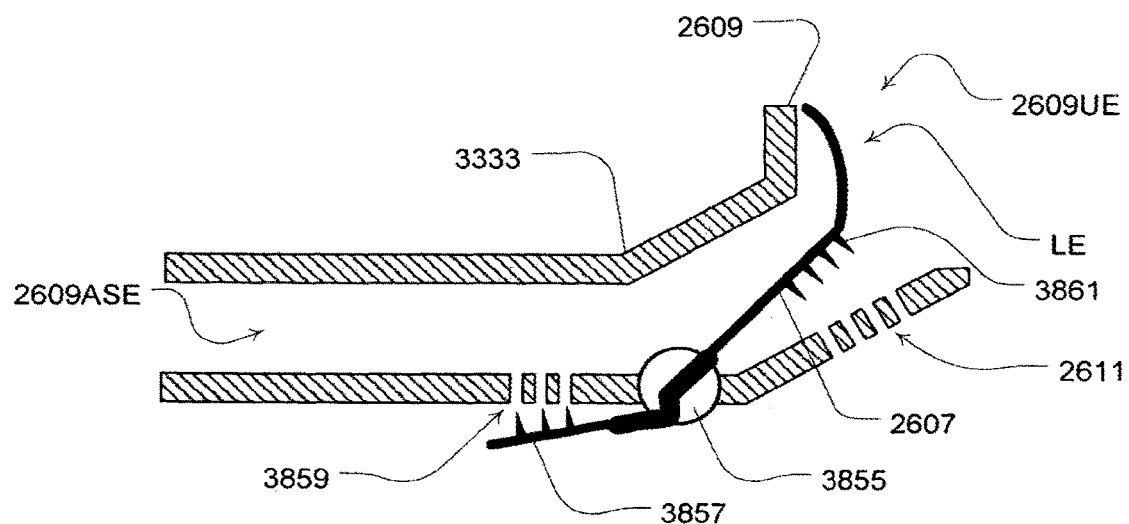
FIG. 38 is an illustration of a channel divider linked to a vent cover in an expiratory position.

In the example of FIG. 38, the divider 2607 is coupled to a pivot 3855. The movement of the divider 2607, such as in response to patient expiration, may further drive a vent cover 3857, which may be configured externally to the conduit, of a secondary vent 3859. Such a linked movement of the vent cover 3857 may open the secondary vent 3859 to release pressure/flow of the conduit so as to permit escape of air or gas generated at the gas supply end 2609ASE of the conduit. Thus, when the divider is in its expiratory position such that the venting portion 2611 is generally open during patient expiration, the secondary vent may open contemporaneously. This case is illustrated in FIG. 38. Conversely, when patient expiration ceases (or inspiration begins), the divider will move to cover the venting portion 2611 such as a result of flow generated at the gas supply end 2609ASE of the conduit. When this occurs, the linked vent cover 3857 will similarly close against the secondary vent 3859 such that the flow of the conduit from the gas supply end will proceed to the user end. This case is illustrated in FIG. 39.

Figure 39:
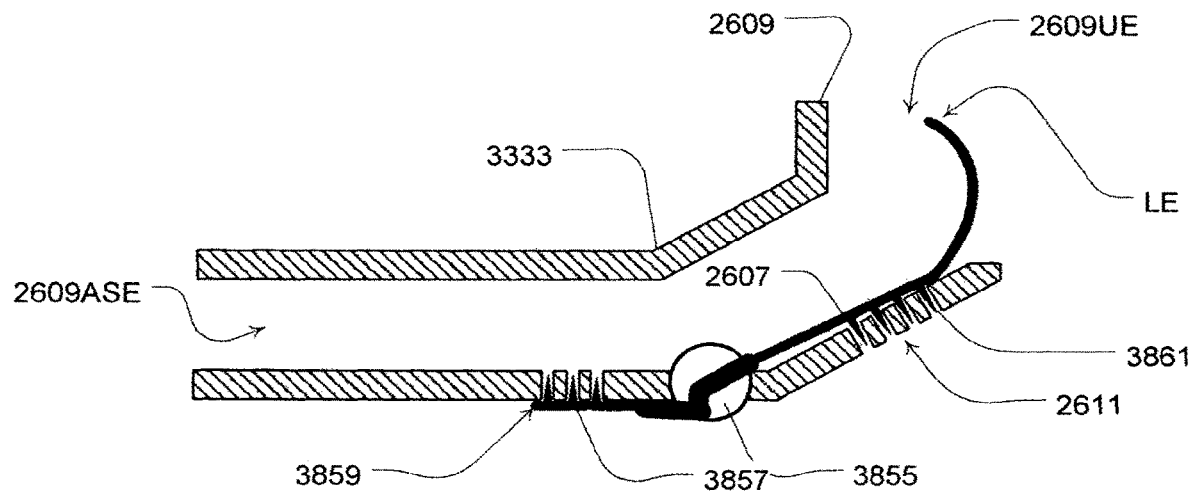
FIG. 39 is an illustration of the example divider of FIG. 38 in an inspiratory position.

As also illustrated in FIGS. 38 and 39, the divider 2607 may be implemented with one or more divider protuberant(s) 3861. Each divider protuberant 3861 may be configured to plug or seal one or more apertures of the venting portion 2611. Thus, when the divider moves toward the venting portions, apertures of the venting portion may be filled or sealed by one or more protuberants of the divider as shown in FIG. 39. Optionally, the vent cover may have similar protuberant structures for sealing the secondary vent as illustrated in FIG. 39. The shape of the apertures filled by each protuberant may typically have a shape that corresponds to the shape of the protuberant. For example, in the case of a conic protuberant, the aperture may have a conic inner cavity.

Figure 40:
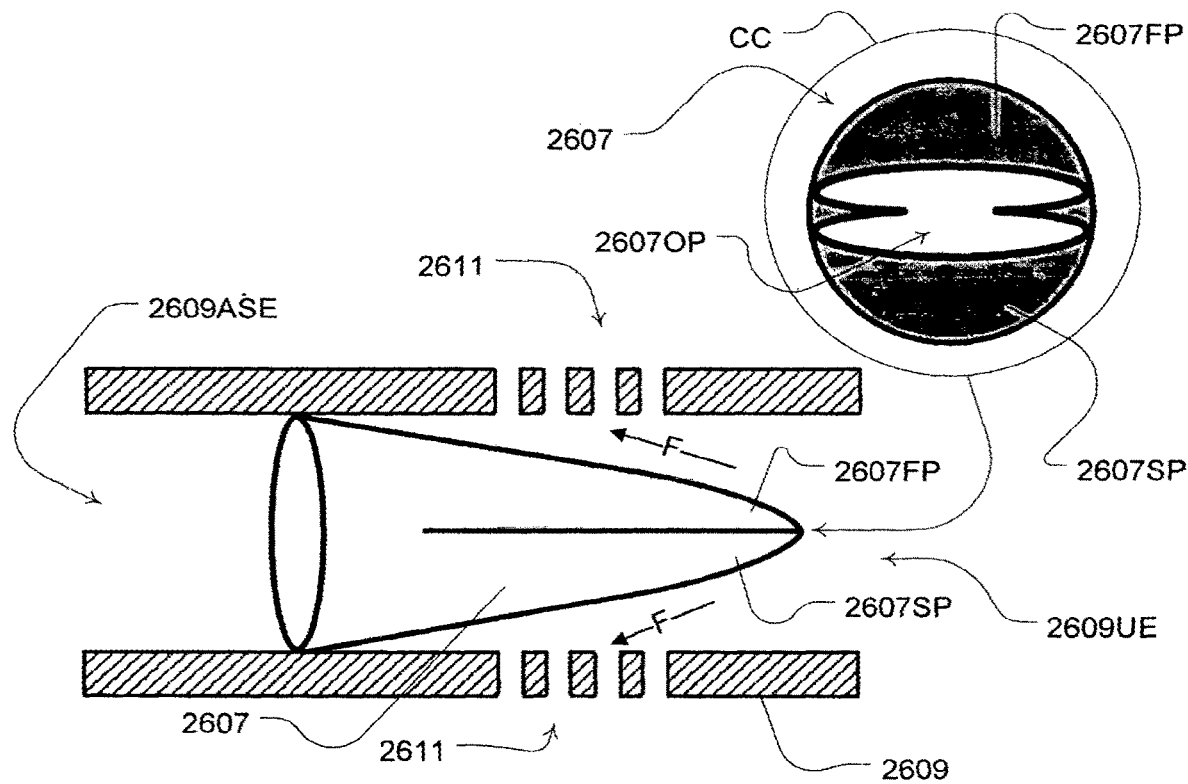
FIG. 40 is a cross sectional illustration of a conduit with a duckbill version of a divider of the present technology in an expiratory position.
Figure 41:
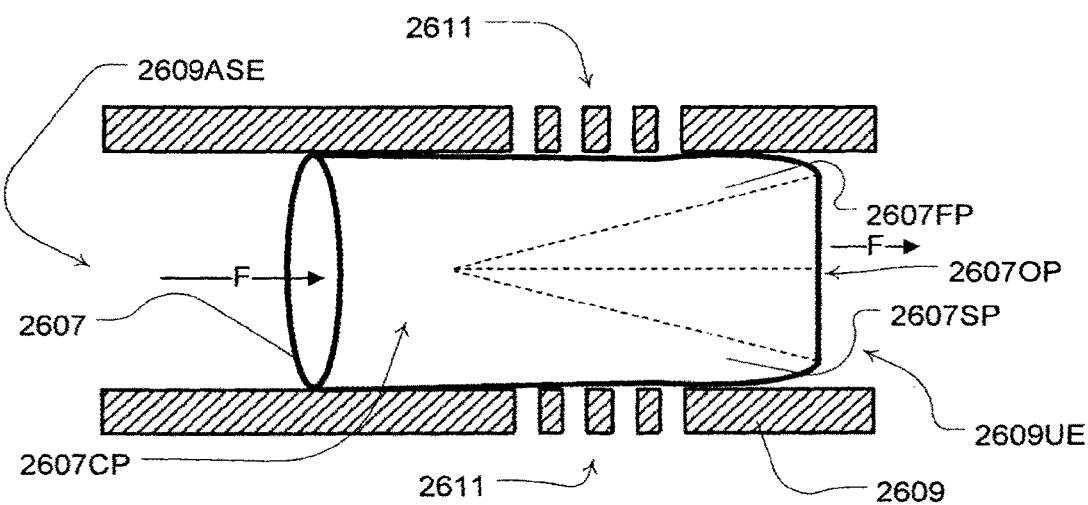
FIG. 41 is a cross sectional illustration of the conduit of FIG. 40 in an expiratory position.

FIGS. 40 and 41 illustrate implementation of a divider 2607 formed in a cylindrical arrangement such as with a duckbill opening 26070P. A front view of the duckbill opening 26070P end of the divider is further illustrated in the callout bubble CC. The divider operates by opening and closing at the duckbill opening 26070P to either permit or preclude a flow of gas from the gas supply end 2609ASE of the conduit to the user end 2609UE of the conduit through the divider. A greater breathable gas pressure or flow from the gas supply end 2609ASE compared to the user end 2609UE, such as from a flow generator of a respiratory treatment apparatus during patient inspiration, forces the duckbill opening to an open position. When the duckbill opening 26070P is open, as illustrated partially in the callout bubble CC of FIG. 40 and fully in FIG. 41, flow proceeds in a direction of flow arrows F through a cylindrical portion 2607CP inside of the divider. In its fully open position, portions of the cylindrical surface of the divider move to cover apertures of the venting portions 2611 of the conduit. The apertures of the venting portions may reside along the internal peripheral surface of the conduit 2609. Such a divider may have a normally closed position, for example when formed of a resilient material, such that a first portion 2607FP and second portion 2607SP move together to fold the divider and close the duckbill opening 26070P in the absence of a greater pressure force at the gas supply end 2609ASE of the conduit. In this folded position, the venting portion 2611 is uncovered by the divider. As a result, air may escape through the venting portion 2611 such as during patient expiration when the pressure at the user end 2609UE is greater than the pressure at the gas supply end 2609ASE.

Figure 42:
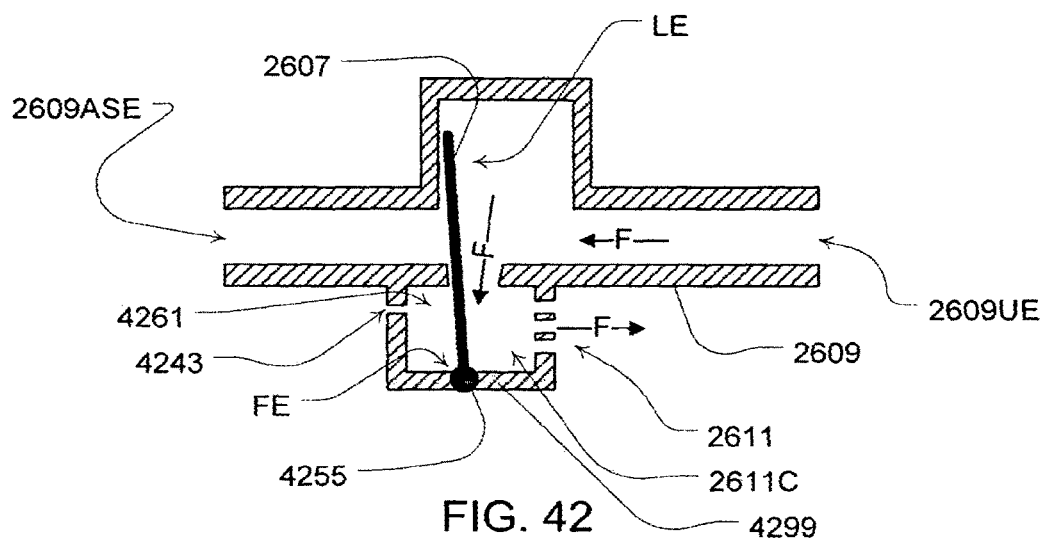
FIG. 42 is a cross sectional illustration of a divider with a venting chamber with the divider in an expiratory position.
Figure 43:
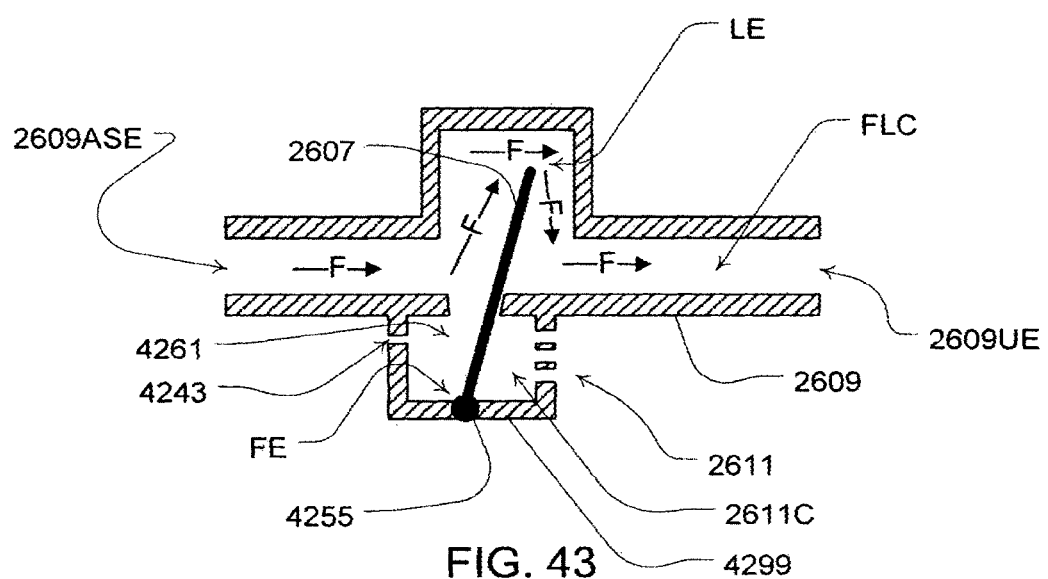
FIG. 43 shows the divider of FIG. 42 in an inspiratory position.

In the example conduit of FIGS. 42 and 43, a divider is implemented with a discrete chamber 4299 with an expiratory venting chamber portion 2611C that leads to the venting portion 2611 and a release chamber portion 4261 that leads to a pressure equalization aperture 4243. The divider separates the expiratory venting chamber portion 2611C from the release chamber portion 4261. In the example, the divider's fixed end FE resides in the discrete chamber such as at a pivot 4255 and the lip end may extend out of the chamber and into, and across, a channel of the conduit. Motion of the divider selectively opens and closes the chamber to either the expiratory venting chamber portion 2611C or the release chamber portion 4261 from the conduit. This divider movement also selective opens and closes the flow channel of the conduit between the gas supply end 2609ASE and the user end 2609UE. For example, during patient expiration, as illustrated in FIG. 42, the divider pivots to open access to the expiratory venting chamber portion 2611C from the user end of the conduit so that expiratory flow may vent into the discrete chamber from the flow channel FLC of the conduit 2609. Once in the expiratory venting chamber portion 2611C, the flow F can pass out the apertures of the venting portion 2611. During patient inspiration, as illustrated in FIG. 43, the divider 2607 moves to close access to the expiratory venting chamber portion 2611C and thereby open flow channel access to the release chamber portion 4261. This movement also contemporaneously opens access of the flow channel of the conduit from the gas supply end 2609ASE of the conduit to the user end 2609UE of the conduit. The flow of the conduit from the gas supply end then may proceed along the divider around the lip end LE toward the user end. The pressure equalization aperture 4243 may be a fine hole or holes permitting the release chamber portion 4261 to equalize with atmosphere. Such a pressure equalization can promote return of the divider to its expiratory position (shown in FIG. 42) during patient expiration when the pressure in the release chamber portion 4261 is lower than the pressure on the opposing side of the divider due to patient expiration. However, the pressure equalization aperture 4243 does not significantly reduce the pressure or flow of the channel between the gas supply end 2609ASE and the user end 2609UE.

Figure 44:
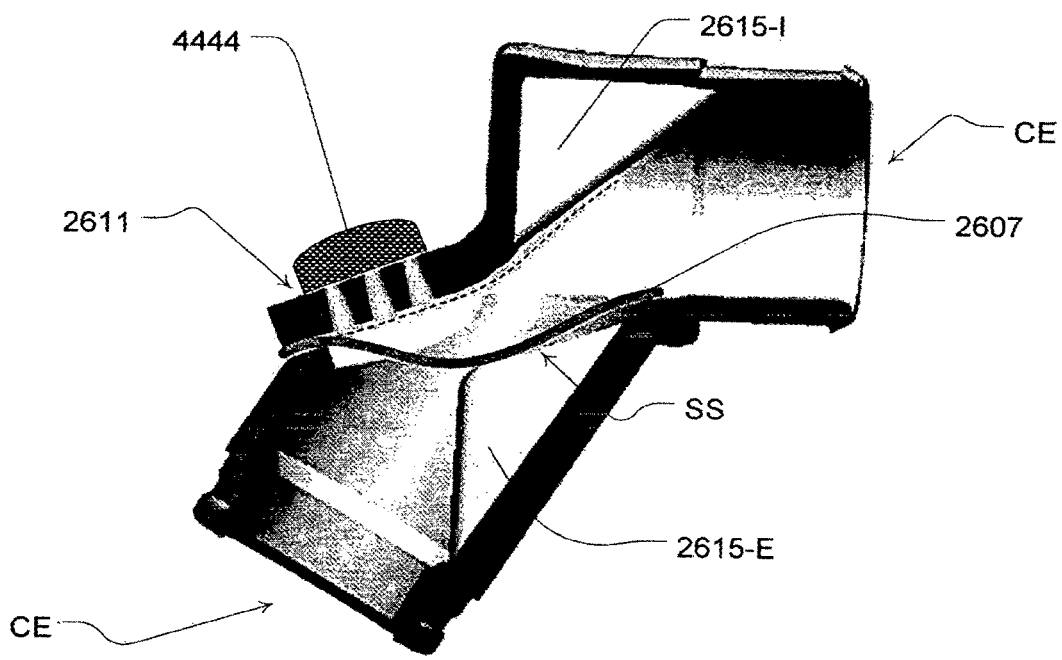
FIGS. 44 and 45 illustrate cross sectional views of an example coupler with features similar to the conduit and flexible divider of FIG. 27.
Figure 45:
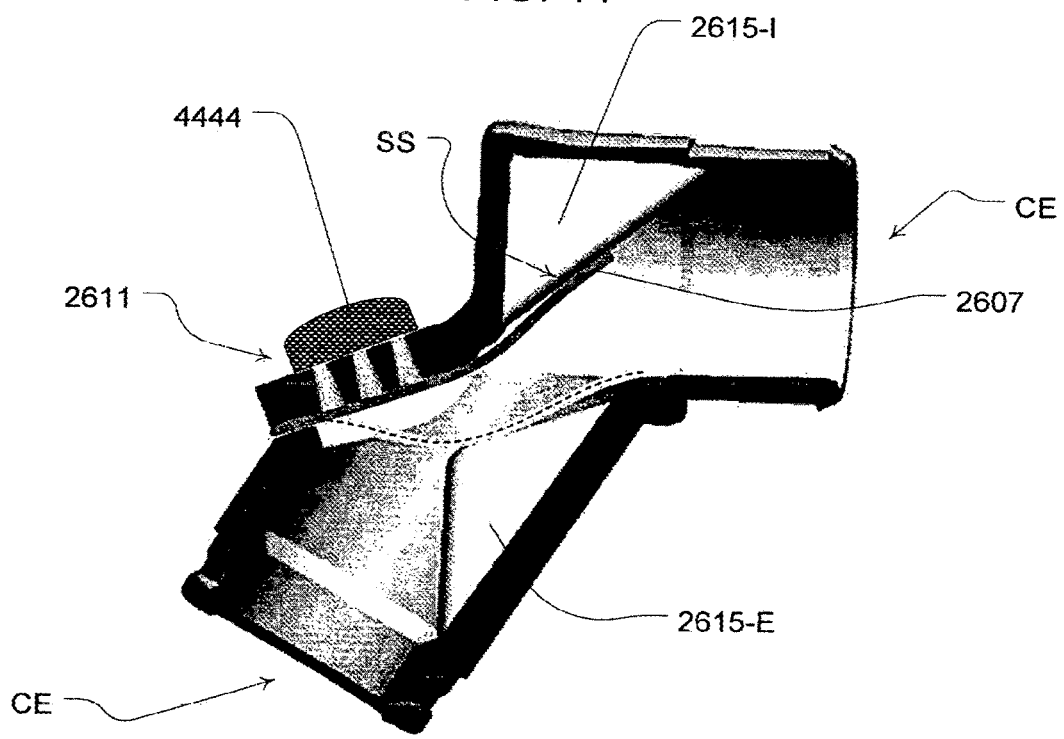

In the example illustrated in FIGS. 44 and 45, which is similar in design and operation to the examples of FIGS. 26 to 31, the flexible channel divider 2607 is configured within a conduit formed as a coupler with coupler ends CE. The coupler may be connected with other conduits or patient interface, such as a mask component. In this example, the conduit is equipped with inspiratory and expiratory divider supports 2615 which prevent excessive travel of the divider or otherwise limit the travel of the divider to desired locations as the divider moves between the opposing supports. The inspiratory divider supports 2615-I are located on an opposing side of the conduit from the side with the expiratory divider supports 2615-E. As shown in FIG. 44, the inspiratory divider supports, such as one or more ribs, support the divider during inspiration. Similarly, as shown in FIG. 45, the expiratory divider supports, such as one or more parallel ribs, support the divider during expiration. Passages between the ribs of the divider supports (not shown in FIGS. 44 and 45) permit gas flow to contact a greater area of a supported side SS of the channel divider when supported by the divider supports so as to permit more readily lifting of the divider away from the supports. As also illustrated in FIGS. 44 and 45, the conduits described herein may also be equipped with an expiratory diffuser 4444 at the venting portion 2611 such as a foam material diffuser. The expiratory diffuser may help to reduce noise associated with the venting of expiratory gas at the venting portion 2611. In some cases, the expiratory diffuser provides a low turbulence and low noise escape pathway. It may also increase impedance of the expiratory path. Such an increase may serve to increase the pressure on the flexible divider during expiration and improve the divider's response.

In some cases, the conduits described herein, such as the conduits employing a channel divider may be equipped with a bypass channel 4690. The bypass channel 4690 may help to permit a small flow of expiratory gas to bypass the divider. For example, the bypass channel may connect the channel of the conduit on either side of the divider and may run through a wall of the conduit in the sense of being integrated with the wall of the conduit. However, in some cases, small connection ports (not shown) each connecting an interior with the exterior of the conduit wall on both sides of the divider may be coupled together with an additional conduit. Such a bypass of gas may then be sensed by a sensor such as when a sensor is positioned up stream of the channel divider. Such a sensor may be more proximate to or within a flow generator to which the conduit is coupled. Such an upstream sensor may then be employed for detecting the patient's respiratory cycle (e.g., inspiration and expiration) and/or pressure in the mask during inspiration and expiration. Alternatively, sensors may be positioned on the patient side of the channel divider such as for detecting a user's respiratory cycle from flow and/or pressure sensors. Example methods for measuring such pressure and flow characteristics are described in more detail herein. Generally, with such a configuration, the bypass flow path can assist with estimating and monitoring expiratory mask pressure and patient flow even when the channel divider is diverting expiratory flow to the venting portion. In this regard, during inspiration the bypass path may have a negligible effect because it can be a very high impedance path compared to the main channel. However, during expiration, the bypass path allows a small amount of flow back towards flow generator sensor(s). This amount of flow can be small enough to be insignificant to the patient's therapy, but can still enable monitoring of patient expiratory parameters from sensor(s) in the flow generator, such as pressure and/or flow.

Figure 47:
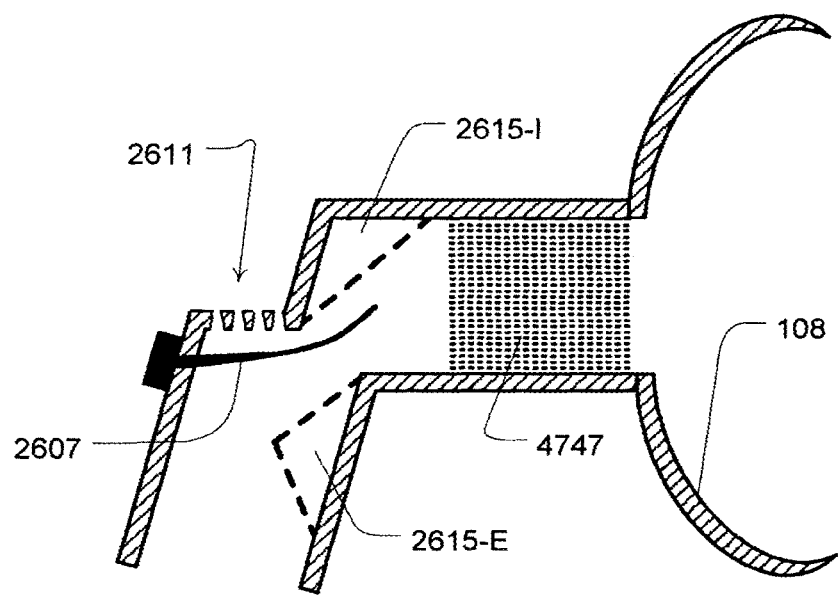
FIG. 47 is a cross sectional illustration of a conduit similar to the conduit of FIG. 46 in series with a passive humidification material.

As previously described herein, the example channel dividers may optionally be configured so as to serve as an exchanger. However, the efficiency of any exchange between the inspiratory and expiratory gas sides of the divider may be increased or implemented by additional exchanger materials, such as upstream and/or downstream of the divider. For example, a filter-like material or foam may be employed in series with the divider of the examples discussed herein. One such example is illustrated in FIG. 47. Such a heat moisture exchange material 4747 is disposed in a common channel of the conduit through which both inspiratory and expiratory gas pass (a bi-directional channel), such as downstream of the divider and more proximate to the patient interface end. Within such a material, both inspiratory and expiratory gases will pass such that there is no distinct inspiratory and expiratory side. Suitable heat moisture exchange materials may include polytetrafluoroethylene (PTFE). The material may be made of a spongy material, a corrugated paper, a bundle of hollow fibres and/or multiple layers of PTFE, any of which may be further treated with a hygroscopic material.

Figure 48:
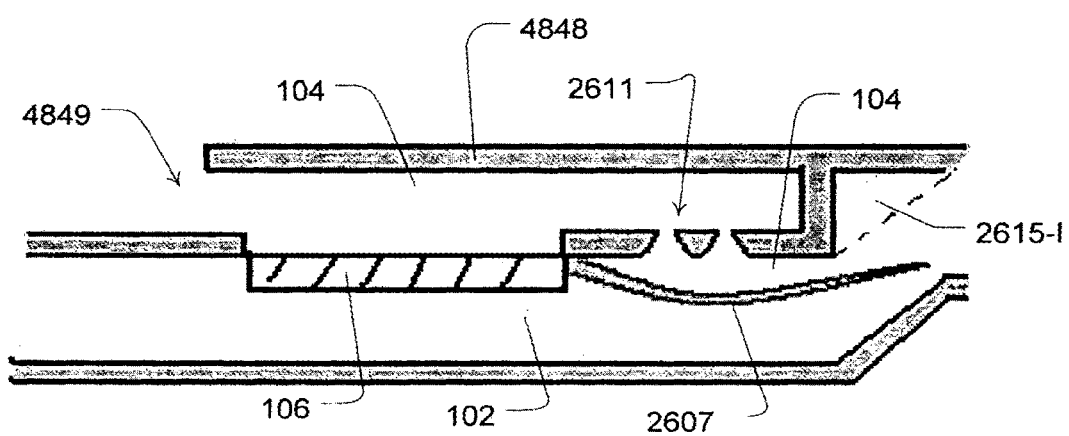
FIG. 48 is a cross sectional illustration of a conduit similar to the conduit of FIG. 46 in series with a further channel divider exchangers of the present technology.

In the example of FIG. 48, an additional exchanger 106 is added upstream of the divider in the conduit, more proximate to a flow generator. To further facilitate the distinct inspiratory channel 102 and expiratory channel 104, the conduit 2609 may include an expiratory extension chamber 4848, into which apertures of the venting portion 2611 vent expiratory gas. An extension opening 4849 may then permit a release of the expiratory gas to atmosphere.

In some cases, the conduit may be implemented with an adjustable continuous vent or a patient interface with such a vent to permit a patient to control setting of the level of humidity in the patient interface. Such a venting feature may typically be downstream of the divider, closer to the user such that when open the adjustable continuous vent will permit venting during expiration and inspiration. The amount of such venting may then be set by a user so as to permit the patient to choose her own level of temperature and humidity comfort. The more the patient increases the continuous vent flow (e.g., by enlarging its opening(s)) it can decrease the humidity affect associated with the action of the divider. For example, some patients may not like feeling too much humidity in the patient interface. In one such example, a dial or sliding adjustment may be implemented that allows the patient to set the level of continuous venting. Such a dial or sliding adjustment may increase or decrease the openings of the continuous vent. In another example, vent apertures of the continuous vent may include vent plugs that may be manually removed (or added) as desired to adjust the level of additional venting via the unplugged apertures of the continuous vent.

Venting Characteristics

In some systems that implement components described herein, it may be desirable to control a therapy pressure. For example, in some implementations, approximate control of the therapy pressure may be achieved by a controller that runs a blower at a constant angular speed. In other implementations control of the therapy pressure may be achieved by a controller that implements a pressure control loop and a characterisation of the gas delivery system.

Figure 49:
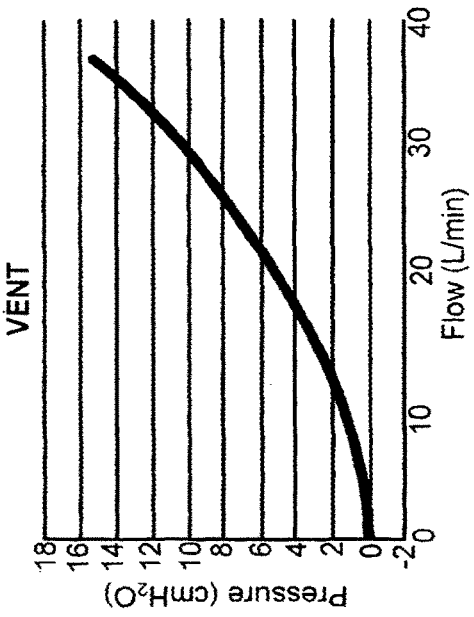
FIGS. 49A, 49B and 49C are graphs that illustrate various flow characteristics of components of a common respiratory treatment system represented by the circuit diagram of FIG. 49.
Figure 49C:
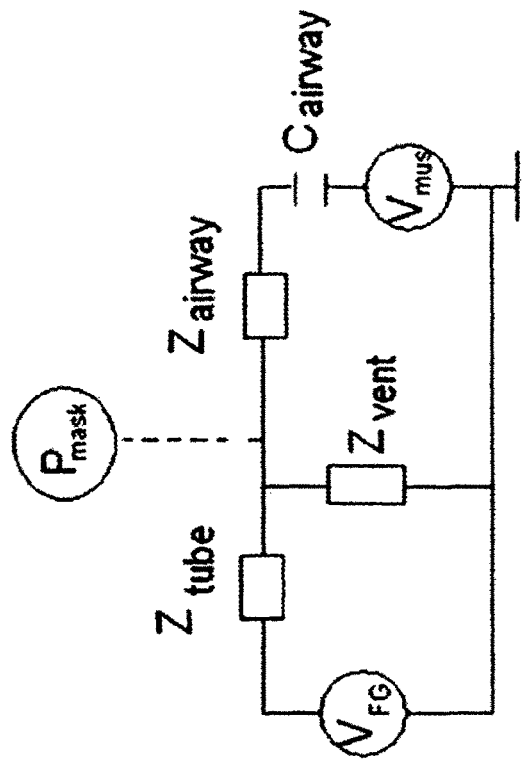
Figure 49A:
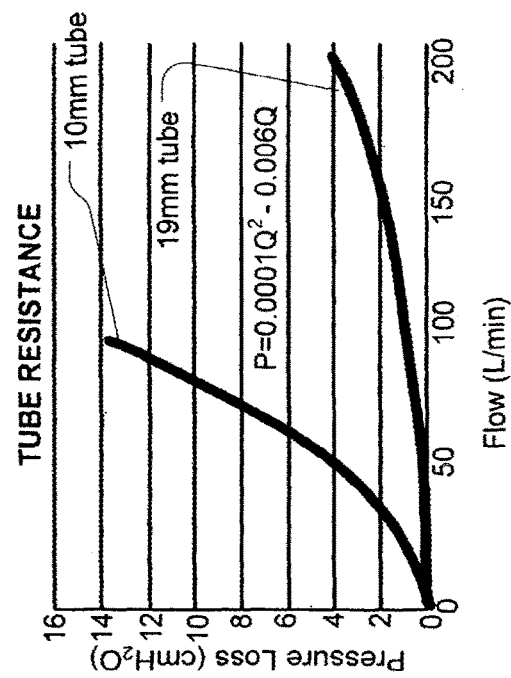
Figure 49B:
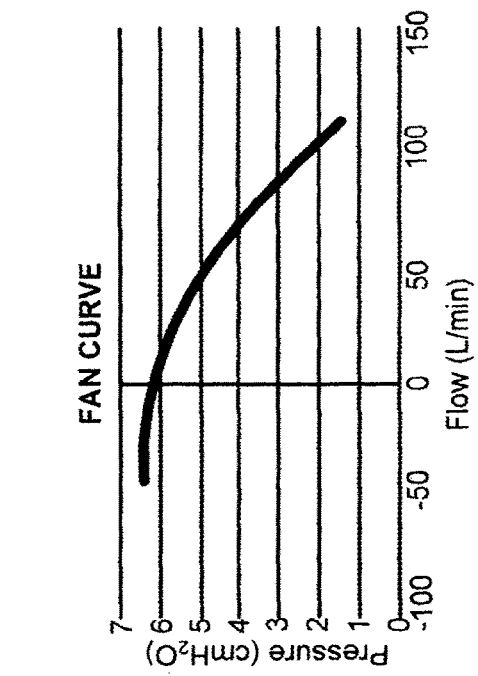
Figure 50:
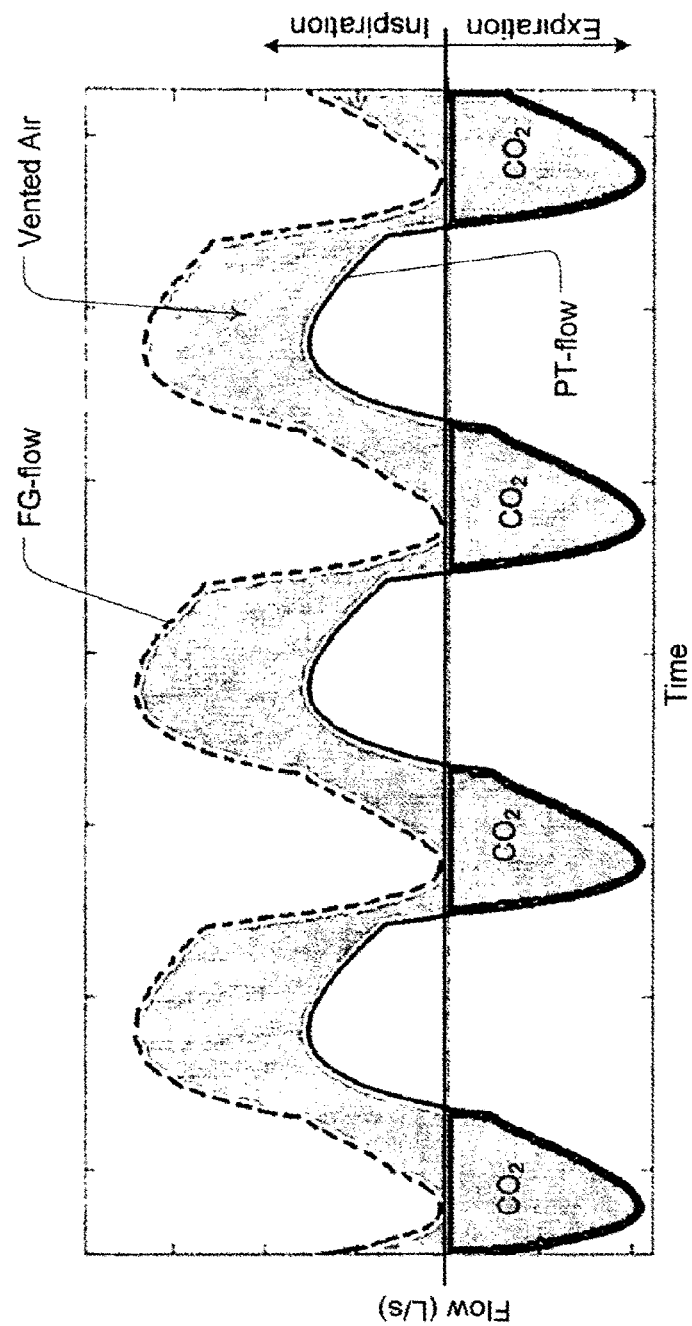
FIG. 50 is a graph illustrating venting with a traditional continuous venting orifice.

Consider the simplified electric circuit analogy of such a system as in FIG. 49 showing typical components of the system as impedance components (Z) (supply conduits, vent and patient airways) and capacitive components (C) (e.g., patient airways) and voltage components (V) (e.g., flow generator "FG" and patient respiratory muscles "mus"). Pressure and flow characteristics of such components may be considered with reference to FIGS. 49A, 49B and 49C. FIG. 49A illustrates example supply conduit resistance for various supply tube sizes (i.e., 10 mm supply tube and 19 mm supply tube). For example, the smaller supply tube experiences greater pressure loss at flows levels compared to larger supply tube at the same flow level. FIG. 49B shows pressure and flow characteristics with reference to a fan curve of a flow generator formed by a motorized impeller. Characteristics of a continuous-type orifice vent are illustrated in the graph of FIG. 49C showing a relationship between pressure and flow. In such a system, the purpose of continuous venting is to allow for the removal of the carbon dioxide from the system, to prevent it from being inspired. But as seen from FIG. 50, the volume of air vented will greatly exceed the volume of expired air, which is the source of the carbon dioxide. FIG. 50 shows the vented air volume with reference to signals corresponding to flow generator flow (FG-flow) and patient flow (PT-flow). As illustrated, the volume of vented air during expiration corresponds with carbon dioxide ($CO_2$).

In some of the examples of the present technology, venting may be minimized during inspiration and all or substantially all of the expired air is vented during expiration. Moreover, the flow generator does not need to produce any more flow than necessary such as when the flow path from the flow generator to the patient is closed during expiration. And importantly, the flow the patient is exposed to is not significantly greater than patient flow. This can have positive implications for patient perception of the therapy, and its effect on drying the patient airways. Flow (Q) and pressure (P) may be considered by the following equations:

During inspiration:

$Q_{FG} = Q_{Patient} + Q_{LEAK}$

Or if there is no leak $Q_{FG} = Q_{Patient}$

During Expiration $Q_{FG} = 0$ $P_{FG} = P_{end\ of\ supply\ tube}$ (Approximately=$P_{therapy}$, for low patient flows)

Where $Q_{FG}$ is flow generator flow; $Q_{Patient}$ is patient flow; $Q_{LEAK}$ is leak flow; $P_{FG}$ is the pressure at the flow generator and $P_{end\ of\ supply\ tube}$ is the pressure at the end of the supply conduit.

Figure 53:
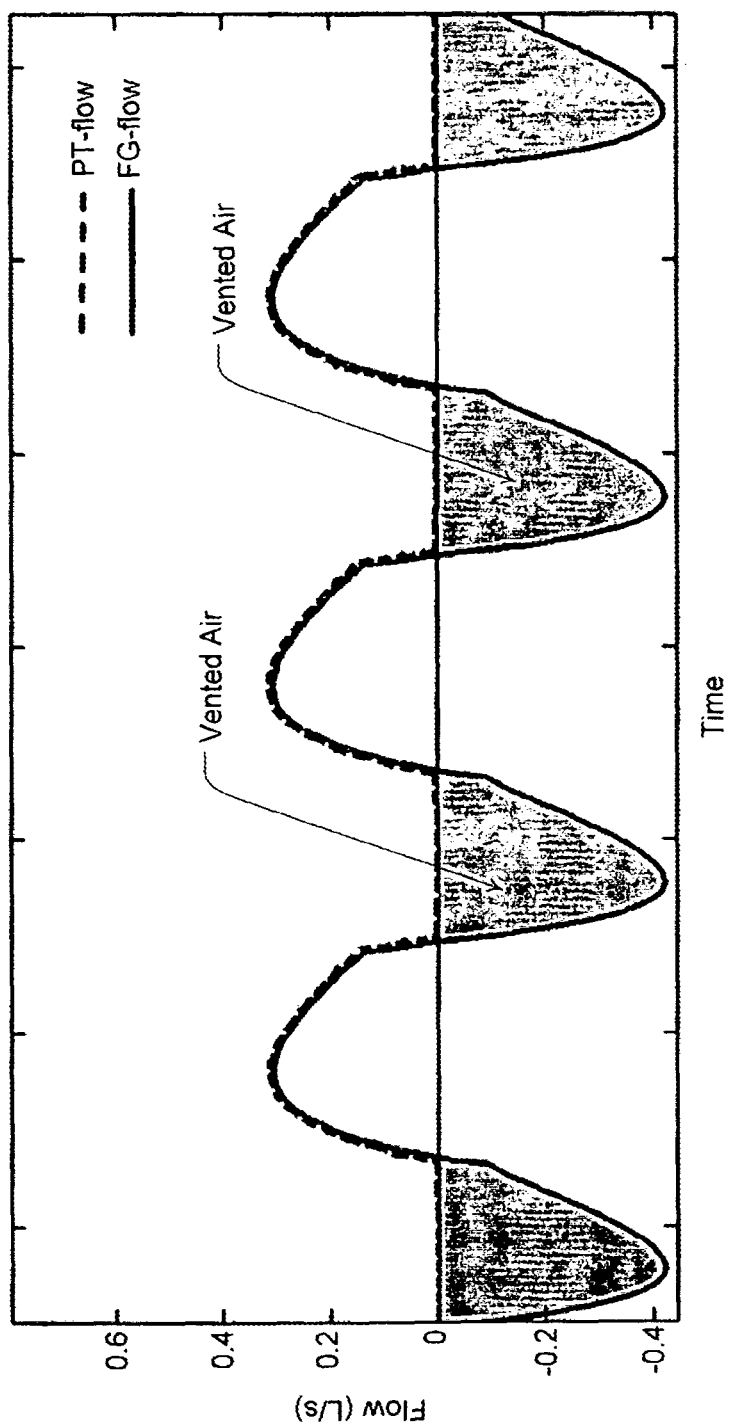
FIG. 53 is a graph illustrating venting with some implementations of the present technology.
Figure 54:
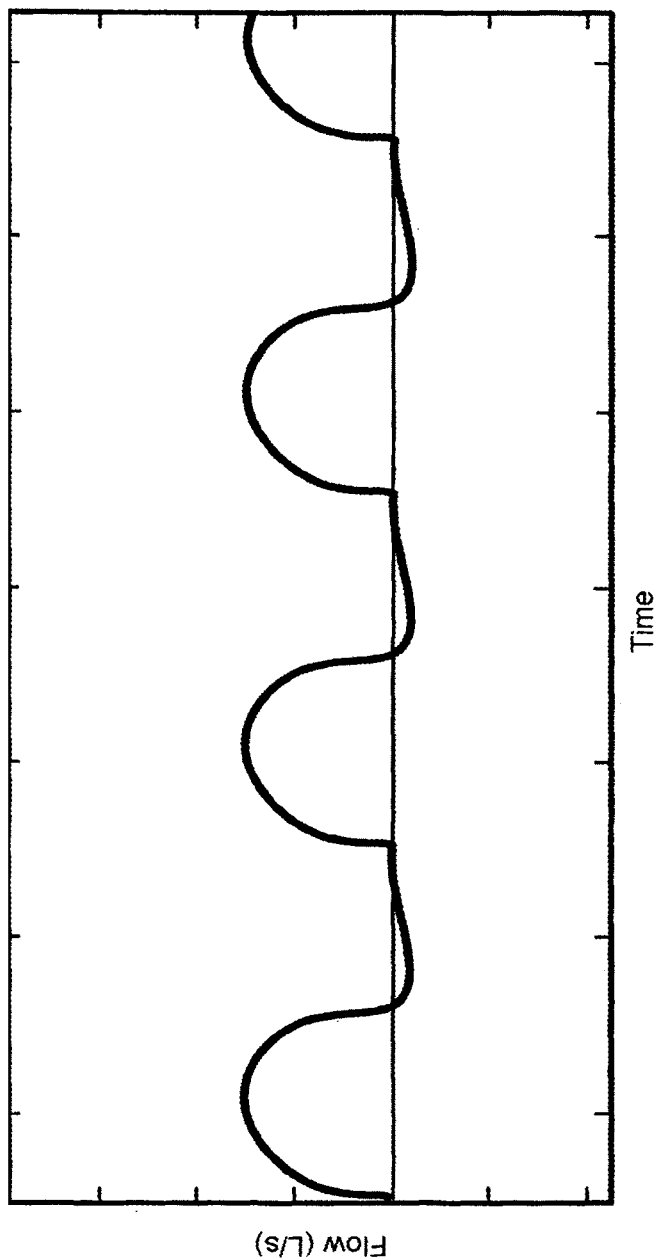
FIG. 54 is a graph illustrating flow vs. time with respect to the conduit with a bypass channel such as the example of FIG. 46.

This is further illustrated in the graph of FIG. 53, which may be compared with the graph of FIG. 50. In FIG. 53, the venting of air occurs during expiration and the flow generator flow corresponds with patient inspiratory flow.

Having low, or no venting on inspiration may provide other advantages such as low acoustic noise, as well as low signal noise in the pressure and flow signal, because at lower velocity there is less turbulence in the air. The low noise signals may make detection of other phenomena more accurate, such as detection of cardiogenic flow. There may also be advantages in the use of forced oscillation techniques, such as for detecting open and closed airways, and the measurement of respiratory mechanics, such as airway resistance and compliance.

Figure 56:
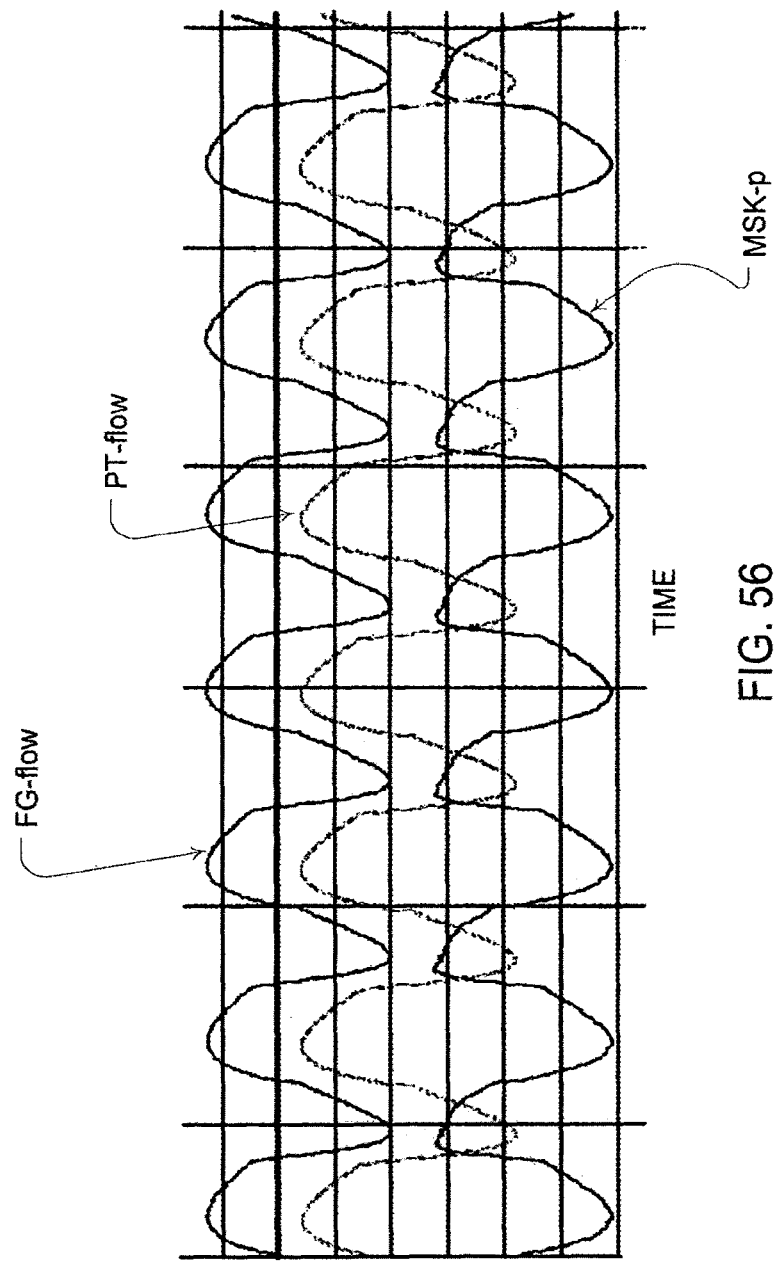
FIG. 56 is a signal graph with flow and pressure data illustrating use of a traditional continuous-type vented mask.
Figure 57:
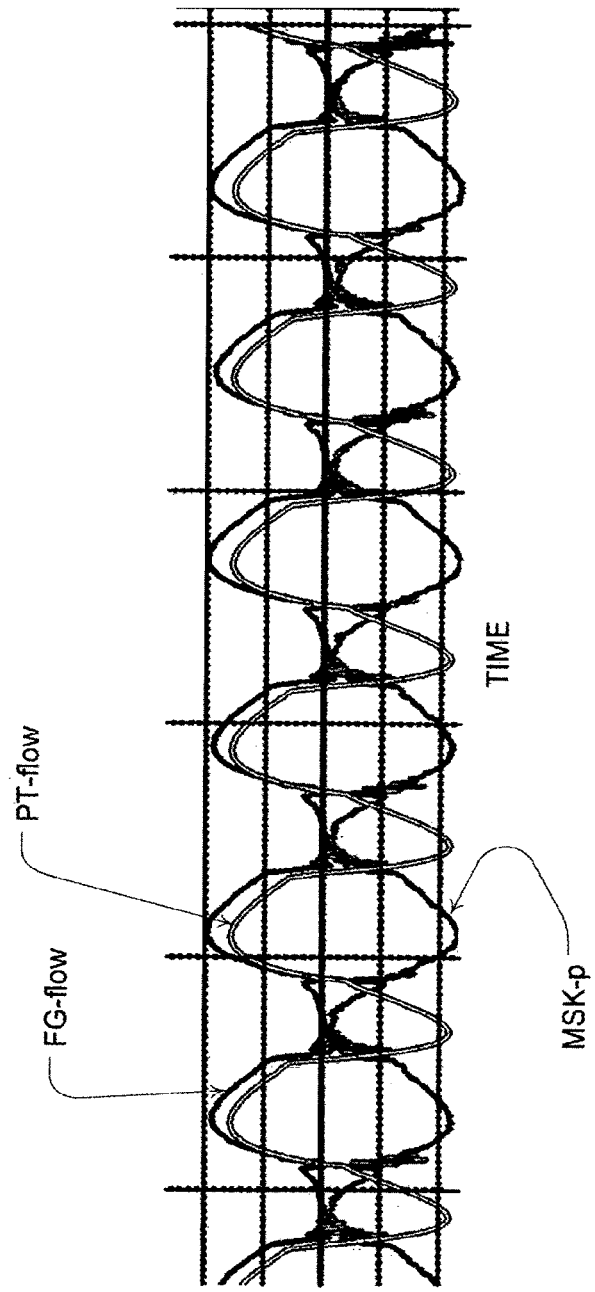
FIGS. 57 and 58 are signal graphs with flow and pressure data illustrating use of a flexible channel divider such as the divider of the conduit of the example of FIG. 26.
Figure 58:
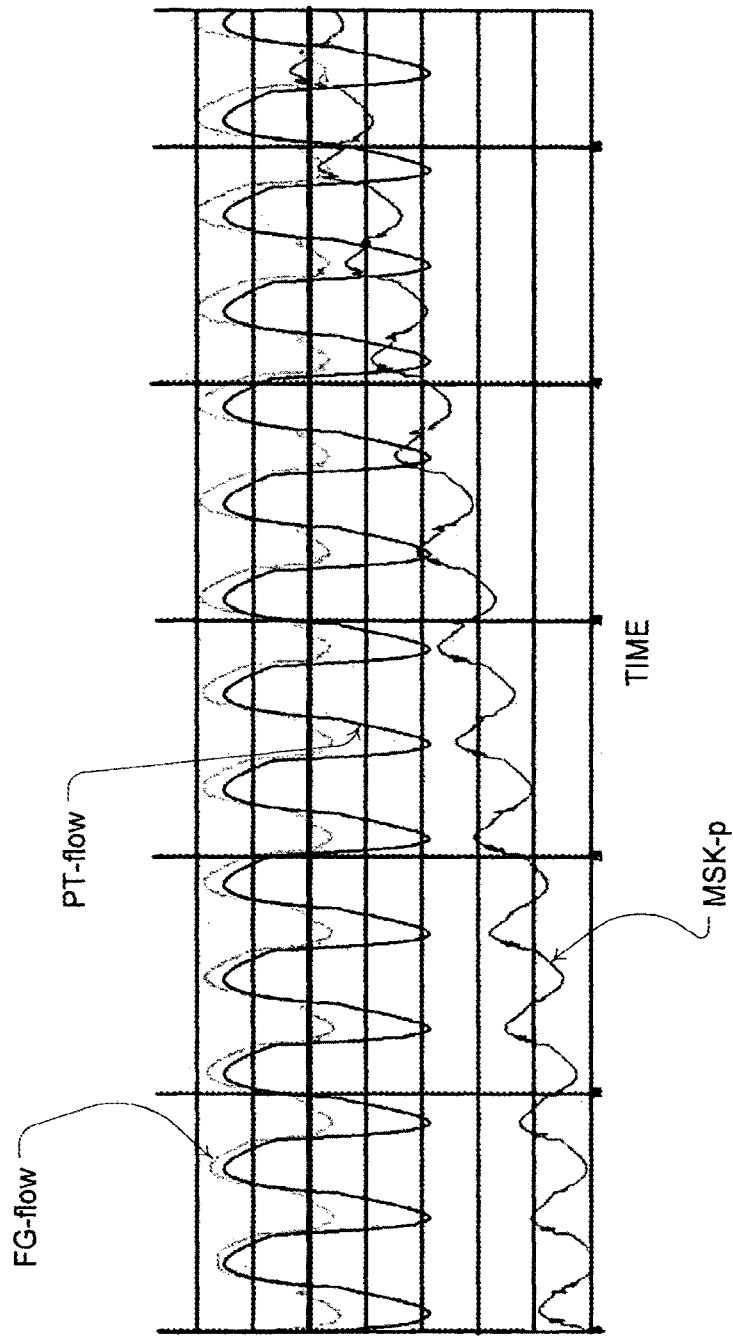

FIGS. 57 and 58 further illustrate simulated performance of an example device having a channel divider such as the embodiment of FIG. 26, 32 or 44. The graph of FIG. 56 illustrates performance of a traditional continuous vented mask. The graphs of FIGS. 56, 57 and 58 show the patient flow (PT-flow), the flow generator flow (FG-flow) and the therapy pressure in a mask, that is, delivered pressure to patient (MSK-p) on a common time axis. The pressure is in a $cmH_2O$ scale up the graph and the flow is a L/sec scale up the graph. FIG. 57 illustrates a test of the channel divider device showing that most of the pressure/flow provided by the flow generator is provided to the patient with very little pressure/flow loss. There are also low pressure swings between the inspiration and expiration phases. The graph of FIG. 56 shows the same test with a standard continuous-type vented mask without the divider flap. The graph shows that there is a much larger pressure/flow loss between the pressure/flow provided by the flow generator and the pressure provided to the patient. There are also much larger pressure swings. Lastly, this graph of FIG. 58 illustrates that the level of flow stays generally constant such that it is unaffected by pressure during a ramping of treatment pressure to the patient controlled by the flow generator.

Expiratory Characteristic Sensing

Figure 55:
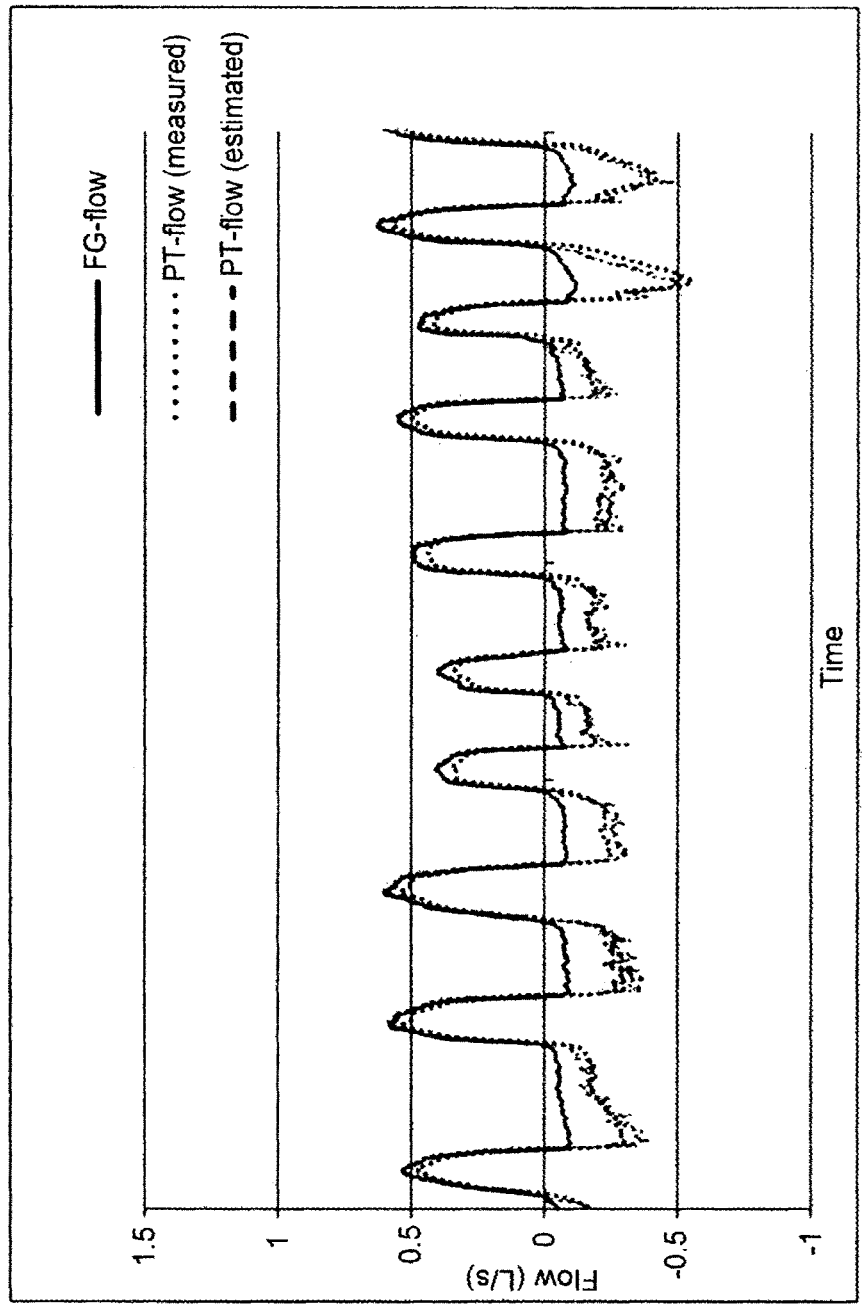
FIG. 55 is a signal graph illustrating patient flow estimation in a system employing a conduit with a bypass channel such as the example of FIG. 46.

In the case of implementation of a bypass channel as discussed with reference to FIG. 46, a controller, such as one with a processor coupled with a sensor, may be configured to estimate patient flow or mask pressure. Example functions for such estimates are described herein. As illustrated in the graph of FIG. 55, a flow sensor may sense flow during inspiration normally but during expiration only a small flow quantity (i.e., less than a typical expiration quantity) through the small bypass channel.

For such a bypass flow path, the relationship between pressure and turbulent flow may be modelled as a second order polynomial.

$$P_{therapy} = K_1 * Q_{FG}^2 + K_2 * Q_{FG} + P_{end\ of\ supply\ tube} \quad (Eq1)$$

Where:

$P_{therapy} - P_{end\ of\ supply\ tube}$ is the pressure difference across the bypass flow path;

$Q_{FG}$ is the flow through the bypass flow path, which is equal to the bypass flow during patient expiration.

$K_1$ and $K_2$ are constants depending on the physical properties of the bypass path, such as geometry and surface finish.

Wherein $P_{therapy}$ is the therapy pressure such as the pressure in the mask; and $P_{end\ of\ supply\ tube}$ is the pressure at the end of the supply tube.

Thereby, during expiration, the mask or therapy pressure may be estimated by the controller from this relationship and the pressure and flow in the flow generator. During inspiration, a traditional sensing of pressure may be implemented by the controller. In this sense, the controller may be configured with one methodology for determining pressure at the mask during inspiration and a different methodology for determining pressure in the mask during expiration.

Furthermore, the relationship between the patient expiratory flow out of the expiratory vent and the therapy pressure may be modelled as second order polynomial for a particular end of tube pressure:

$$P_{therapy} = K_3 \cdot Q^2 + K_4 \cdot Q + P_{end\ of\ supply\ tube} \quad (EQ2)$$

Where $K_3$ and $K_4$ are constant for a particular range of end of tube pressures and patient flow.

To assist with providing either a comfortable or controllable therapy it may be desirable to arrange the system such that for patient expiration a large range of expiratory flows relates to a relatively small range in differential pressures (between therapy and atmosphere) for a particular end of supply tube pressure. This requires relatively small values of $K_3$ and $K_4$. This can be achieved by having a large enough aperture and by controlling the dynamic pressure the flow exerts on the flexible divider.

Equation (EQ2) may also take different forms, such as if $K_3$ and $K_4$ are made very small the equation may be approximated as:

$$P_{therapy} = P_{end\ of\ supply\ tube} \quad (EQ3)$$

The relationship may be better modelled as a function (f) other than a polynomial, or a higher order polynomial, for example, a non-monotonic relationship such that at lower patient flow rate a higher component of static therapy pressure is applied to straining the flexible divider, and at higher flow rates the dynamic component of the gas pressure, and the component of the pressure associated with accelerating the gas/fluid by changing its direction may form a larger proportion of the pressure required to strain the divider such that the static pressure component should be less. Practically, this allows less mask pressure at higher patient flows for particular ranges of therapy pressures and patient flows.

$$P_{therapy} = f(P_{end\ of\ supply\ tube}, Q_{patient}) \quad (EQ4)$$

Similarly, the pressure loss with flow relationship in the connecting tubes may be characterised as $$P_{end\ of\ supply\ tube} = K_5 * Q_2 + K_6 * Q + P_{FG} \quad (EQ5)$$

Thus, from measurements of the pressure and flow in the flow generator it is possible to estimate the pressure at the end of the supply tube (e.g., with pressure drop characteristics of the supply tube), and then using any of the equations above it is possible for a processor to derive estimates for the therapy pressure and patient flow, such as during expiration. For example, the estimated patient flow is illustrated in the graph of FIG. 55. In such a case, a controller or processor may be programmed with data and instructions for implementing the functions or equations. Thus, a flow generator apparatus may include integrated chips, a memory and/or other control instruction, data or information storage medium. Programmed instructions encompassing such methodologies may be coded on integrated chips in the memory of the device or apparatus to form an application specific integrated chip (ASIC). Such instructions may also or alternatively be loaded as software or firmware using an appropriate data storage medium.

With an estimate of patient flow and therapy pressure (as described) it is possible to control therapy pressure, and to perform all of the algorithms that utilize or analyse such information, such as CPAP, autoset CPAP, bi-level therapy, apnoea/hypopnoea detection, measurement of patient compliance, estimate of tidal volume, targeting a tidal volume with pressure support, expiratory pressure relief, detection of respiratory rate, etc.

While such dividers are generally capable of passive or pneumatic operation as discussed herein based on changes in flow and pressure primarily attributable to patient respiration and/or flow generator pressure adjustments, other controlled operation configurations may be implemented. For example, the dividers may be actively controlled by motorized components, electro-magnetic control components etc. For example, the divider may be formed with plastic or metal materials and may be magnetic so as to be selectively responsive to one or more controlled magnetic fields, such as from an electro-magnet or field coils controlled by a controller of the apparatus with which the conduit is utilized (e.g., a respiratory treatment apparatus controller). In some cases, the divider may be configured to change shape (e.g., shrink and grow) based on a selective application of electrical potential so as to control the divider to open and close a venting portion. The conduit with the dividers described herein may be implemented to be part of or closely implemented with a patient interface (e.g., a respiratory mask). However, the conduit may also be implemented farther away such as being more proximate to, or even in, the gas supply components or flow generator rather than to the mask. In some cases, a leak vent may be added to the conduit to provide a continuous leak (e.g., a 5 ml flow leak) such that the divider does not open and close the leak vent.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. Thus, any one or more of the features of any example described herein may be applied to any of the other examples described herein. It will further be understood that any reference herein to subject matter known in the field does not, unless the contrary indication appears, constitute an admission that such subject matter is commonly known by those skilled in the art to which the present technology relates.

The invention claimed is:

1. An exchanger conduit to condition a breathable gas for a patient interface that delivers a respiratory treatment comprising:
   an exchanger; and
   a conduit for housing the exchanger, wherein the conduit has a first end and a second end and a length extending between the first end and the second end,
   wherein the exchanger forms with the conduit a first gas path and a second gas path, wherein the first gas path is configured to conduct an inspiratory gas and the second gas path is configured to conduct an expiratory gas,
   wherein the exchanger is configured to transfer a component of the gas of the second gas path to the gas of the first gas path, and
   wherein the exchanger comprises a folded surface that divides the first gas path and the second gas path, and wherein the folded surface comprises a plurality of folds, wherein each fold of the plurality of folds includes a crease that extends that runs generally parallel to the length of the conduit.

2. The exchanger conduit of claim 1 wherein the exchanger comprises a temperature conducting material whereby the component of the gas transferred from the gas of the second gas path to the gas of the first gas path is temperature.

3. The exchanger conduit of claim 1 wherein the exchanger comprises a moisture conducting material whereby the component of the gas transferred from the gas of the second gas path to the gas of the first gas path is moisture.

4. The exchanger conduit of claim 1 wherein the exchanger comprises a hydrophilic material.

5. The exchanger conduit of claim 1 wherein the exchanger comprises a carbon dioxide rejecting material.

6. The exchanger conduit of claim 1 wherein the exchanger comprises a cellulose material.

7. The exchanger conduit of claim 1 wherein the first gas path and the second gas path each comprise a plurality of flow pathways, the exchanger dividing the flow pathways with a plurality of generally parallel wall surfaces, wherein each wall surface separates a pathway of the first gas path and a pathway of the second gas path.

8. The exchanger conduit of claim 1 wherein the exchanger comprises a plurality of heat conducting fins.

9. The exchanger conduit of claim 1 wherein the exchanger comprises a plurality of capillary apertures.

10. The exchanger conduit of claim 1 wherein the first gas path further comprises an input aperture with a coupler for an oxygen source.

11. The exchanger conduit of claim 1 wherein the conduit further comprises a fluid supply aperture, the fluid supply aperture including a fluid channel to supply a fluid to a material of the exchanger.

12. The exchanger conduit of claim 1 further comprising a flexible chamber configured to prevent flow of an expiratory gas in the first gas path.

13. The exchanger conduit of claim 1 further comprising a flexible chamber configured to prevent flow of an inspiratory gas in the second gas path.

14. The exchanger conduit of claim 1 further comprising a venting portion.

15. The exchanger conduit of claim 1 wherein the first gas path comprises an input end and an output end, the output end being adapted for interfacing with a patient respiratory system.

16. The exchanger conduit of claim 15 wherein the exchanger conduit further comprises a valve, the valve configured at the first gas path to permit gas flow through the first gas path from the input end to the output end but not from the output end to the input end.

17. The exchanger conduit of claim 16 wherein the output end comprises a respiratory mask.

18. The exchanger conduit of claim 16 wherein the output end comprises a coupler for a respiratory mask.

19. The exchanger conduit of claim 16 wherein the input end comprises a coupler for an output conduit of a respiratory treatment apparatus.

20. The exchanger conduit of claim 1 wherein the second gas path comprises an input end and an output end, the input end being adapted for interfacing with a patient respiratory system and the output end being adapted for interfacing with an expiratory vent to atmosphere.

21. The exchanger conduit of claim 20 wherein the second gas path includes a valve to permit expiratory gas to vent to atmosphere through the expiratory vent and prevent a flow of air into the second gas path from atmosphere through the vent.

22. The exchanger conduit of claim 20 wherein the expiratory vent comprises a flexible barrier, the flexible barrier preloaded with a tension to be operable to selectively open the expiratory vent to maintain pressure in the second gas path below a pressure threshold that is greater than atmospheric pressure.

23. The exchanger conduit of claim 22 wherein the expiratory vent comprises a pair of tensioning bars, through which the flexible barrier is tensioned.

24. The exchanger conduit of claim 1 wherein the exchanger comprises an adjustment mechanism to selectively increase or decrease an efficiency of the transfer of the component of the gas of the second gas path to the gas of the first gas path.

25. The exchanger conduit of claim 24 wherein the adjustment mechanism increases or decreases a flow contact surface area of the exchanger.

26. The exchanger conduit of claim 25 further comprising a processor and a sensor, wherein the processor is configured to control the adjustment mechanism to adjust the efficiency of the exchanger in response to a signal from the sensor.

27. The exchanger conduit of claim 26 wherein the sensor comprises a temperature sensor.

28. The exchanger conduit of claim 26 wherein the sensor comprises a humidity sensor.

29. The exchanger conduit of claim 1 wherein the exchanger is insertable between a top conduit part and a bottom conduit part.

30. The exchanger conduit of claim 29 where the top conduit part and exchanger form the first gas path and wherein the bottom conduit part and the exchanger form the second gas path.

31. A patient interface including the exchanger conduit of claim 1.

32. A flow generator to supply a respiratory therapy to a patient, including the exchanger conduit of claim 1.

* * * * *